US006951742B1

(12) United States Patent
Duan

(10) Patent No.: US 6,951,742 B1
(45) Date of Patent: Oct. 4, 2005

(54) METHODS AND VECTORS FOR GENERATING ANTIBODIES IN AVIAN SPECIES AND USES THEREFOR

(75) Inventor: Lingxun Duan, North Wales, PA (US)

(73) Assignee: GenWay Biotech, Inc., San Diego, CA (US)

( * ) Notice: Subject to any disclaimer, the term of this patent is extended or adjusted under 35 U.S.C. 154(b) by 0 days.

(21) Appl. No.: 09/573,442

(22) Filed: May 16, 2000

Related U.S. Application Data

(63) Continuation-in-part of application No. PCT/US99/26843, filed on Nov. 12, 1999.
(60) Provisional application No. 60/108,487, filed on Nov. 16, 1998.

(51) Int. Cl.[7] .................... C12N 15/09; C12N 15/64; C07K 16/00; C07H 21/04; G01N 33/48
(52) U.S. Cl. .................... 435/69.3; 435/6; 435/91.4; 435/320.1; 530/389.1; 536/23.5; 702/19
(58) Field of Search .................... 204/450; 435/320.1, 435/69.1, 69.3, 91.4, 6, 7.1; 536/231, 23.5; 530/387.1, 389.1; 702/19

(56) References Cited

U.S. PATENT DOCUMENTS

| 4,518,690 A | 5/1985 | Guntaka |
| 4,957,865 A | 9/1990 | Samarut et al. |
| 5,302,509 A | 4/1994 | Cheeseman |
| 5,324,639 A | 6/1994 | Brierley et al. |
| 5,518,913 A | 5/1996 | Massie et al. |
| 5,703,055 A | 12/1997 | Felgner et al. |
| 5,714,353 A | 2/1998 | Pathak et al. |

FOREIGN PATENT DOCUMENTS

| WO | WO 91/06678 | 5/1991 |
| WO | WO 93/21340 | 10/1993 |
| WO | WO 94/24268 | 10/1994 |
| WO | WO 95/35505 | 12/1995 |
| WO | WO 98/22510 | 5/1998 |
| WO | WO 99/02188 | 1/1999 |
| WO | WO 99/21977 | 5/1999 |
| WO | WO 99/39210 | 5/1999 |
| WO | WO 99/40434 | 8/1999 |
| WO | WO 00/09730 | 2/2000 |

OTHER PUBLICATIONS

Persidis An ambitious drug development platform attempts to link gene sequence to expressed phenotype under various physiological states vol. 16 Apr. 1998.*
Unwin et al. Urological malignancies and the proteomicgenomic interface 1999 20,3629–3637.*
Chambers Proteomics:a new approach to the study of disease 2000 192:280–288.*
Adams et al., Science (1991) 252:1651–1656.
Ahluwalia, et al., Biosens. Bioelectron. (1992) 7(3):207–214.

Akiyama et al., "Tissue–Specific Expression of Mouse Tyrosinase Gene in Cultured Chicken Cells," Experimental Cell Research (1994) 214(1):154–162.
Altchul et al., Nature Genetics (1994) 6:119–129.
Bassuk et al., Eur. J. Biochem. (1993) 218(1):117–127.
Bayer et al., Trends Biotechnol. (1994) 12:379–386.
Been & Cech, Cell (1986) 47:206–216.
Bhatia et al., Anal. Biochem. (1989) 178(2):408–413.
Blackstock et al., "Proteomics: Quantitative and Physical Mapping of Cellular Proteins," Trends in Biotechnology (1999) 17(3):121–127.
Blaney and Martin, Curr. Opin. Chem. Biol. (1997) 1(1):54–9.
Bodescot & Brison, BioTechniques (1997) 22(6):1119–1125.
Boersma et al., "Adjuvant Properties of Stable Water–in–Oil Emulsions: Evaluation of the Experience with Specol." Research in Immunology (1992) 143:503–512.
Bonaldo et al., Genome Research (1996) 6:791–806.
Buckler et al., Proc. Natl. Acad. Sci. (1991) 88:4005–4009.
Burke et al., Scienc, (1987) 236:806–812.
Bussey, Yeast (1997) 13(16):1501–1503.
Chattergoon et al., FASEB (1997) 11:753–763.
Chenchik et al., Bio/Techniques (1996) 21:526–534.
Chong et al., "Utilizing the C–terminal cleavage activity of a protein splicing element to purify recombinant proteins in a single chromatographic step." (1998) Nucl. Acids Res. 26:5109–5115.
Christoffersen, Nature Biotechnology (1997) 15:484–484.
Condreay et al., J. Virolog, (1990) 64:3249–3258.
Diatchenko et al., Proc. Natl. Acad. Sci. (1996) 93:6025–6030.
Drmanac et al., Science (1993) 260:1649–1652.
Duan et al., Gene Therapy (1997) 4:533–543.
Duan et al., Proc. Natl. Acad. Sci. (1994) 91:5075–5079.
Feinberg & Vogelstein, Analyt. Biochem. (1983) 132:6–13.
Fickett & Hatzigeorgious, Genome Research (1997) 7:861–878.

(Continued)

Primary Examiner—Marjorie Moran
Assistant Examiner—Lori A. Clow
(74) Attorney, Agent, or Firm—Morrison & Foerster LLP

(57) ABSTRACT

The present invention relates to processes for producing polyclonal and monoclonal antibodies to an antigen in an avian species, preferably in a chicken, using polynucleotide vaccination. The present invention also relates to processes for determining the proteomics profile of a set of pre-selected DNA sequences isolated from a bio-sample, preferably the proteomics profile of a human cDNA library. The present invention additionally relates to processes for identifying physiologically distinguishable markers associated with a physiologically abnormal bio-sample. The present invention further relates to antibody arrays, integrated databases for identification of genes and proteins, multi-functional gene expression vectors, and methods of producing and using such antibody arrays, integrated databases and multi-functional gene expression vectors.

34 Claims, 16 Drawing Sheets

OTHER PUBLICATIONS

Freij–Larsson, et al., *Biomaterials* (1996)17(22):2199–2207.
Fynan et al., *Proc. Natl. Acad. Sci.* (1993) 90:11478–11482.
Gastel & Sutter, *BioTechniques* (1996) 20:870–875.
Geutskens, S.B. et al. *Gene Therapy* (2000) 7:1410–1416.
Gilkes et al., "Precise excision of the cellulose binding domains from two *Cellulomonas fimi* cellulases by a homologous protease and the effect on catalysis", *J. Biol. Chem.* (1988) 263:10401–10407.
Gilkes et al., "Domains in microbial beta–1, 4–glycanases: sequence conservation, function, and enzyme families" *Microbiol. Rev.* (1991) 55:303–315.
Goldstein et al., *J. Bacteriol.* (1993)175:5762–5768.
Gonzalez & Sylvester, *Genome Research* (1997) 7:65–70.
Hache et al., *J. Biol. Chem.* (1983) 258(7):4556–4564.
Harland & Misher, *Development* (1988) 102:837–852.
Hicks et al., *Nature Genetics* (1997) 16(4):338–344.
Huang et al., *Virology* (1988) 163:462–470.
Humphery–Smith et al., *Electrophoresis* (1997) 18:1217–1242.
James, *Biochem. Biophys. Res. Comm.* (1997) 231:1–6.
Jonsson et al., *Biochem. J.* (1985) 227(2):373–378.
Kodihalli et al., *J. Virol.*,(1997) 71(5):3391–3396.
Kostichka et al., *Bio/Technology* (1992) 10:78–81.
Landy, *Current Opinion in Genetics & Development* (1993) 3:699–707.
Lantis et al., *Surgical Endoscopy* (1998) 12(2):170–176.
Lösoh, U., et al., "The chicken egg, an antibody source", *Journal of Veterinary Medicine* (1986)B33:609–619.
Lovett et al., *Proc. Natl. Acad. Sci.* (1991) 88:9628–9632.
Mathies & Huang, *Nature* (1992) 359:167–169.
Martin–Gallardo et al., *Nature Genet.* (1992) 1:34–39.
Martinon F. et al., "Induction of virum–specific cytotoxic T lymphocytes in vivo by liposome–entrapped mRNA", *Eur. J. Immuno.,* (1993) 23:1719–22.
McLaren et al., "The Use of Caprylic Acid for the Extraction of the Immunoglobulin Fraction from Egg Yolks of Chickens Immunised with Ovine Alpha–Lactalbumin," *Journal of Immunological Methods* (1994) 177(1–2):175–174.
Mendoza et al., "High–Throughput Microarray–Based Enzyme–Linked Immunosorbent Assay (ELISA)," *BioTechniques* (1999) 27:778–788.
Meyer, D., et al., "Purification of Recombinant Protein by Fusion with Thermally–Responsive Polypeptides", *Nature Biotechnology* (1999) 17:1112–1115.
Milner et al. *Nature Biotechnology* (1997) 15:537–541.
Naldini et al., *Science* (1996) 272:263–268.
Nemoto, Y. *Japanese Journal of Clinical Medicine* (1998) 56(1):224–232.
Neto et al., *Gene* (1997) 186:135–142.
Nishinaka et al., *J. Immunological Methods* (1991) 139:217–222.
Nishinaka et al., "Two Chicken B Cell Lines Resistant to Ouabain for the Production of Chicken Monoclonal Antibodies," *Journal of Veterinary Medical Science* (1996) 58(11):1053–1056.
Ochsenbein A. et al. *Proc Natl Acad Sci USA* (1999) 96:2233–2238.
Okubo et al., *Nature Genet.* (1992) 2:173–179.
Oliver et al., *Nature* (1992) 357:38–46.
Ong, E., et al., *Bio/Technol.* (1989) 7:604–607.
Pacchioni et al., *BioTechniques* (1996) 21:644–649.
Parks et al., *J. Virol.* (1986) 60:376–384.
Pathak et al., "Broad Spectrum of in vivo Forward Mutations, Hypermutations and Mutational Hotspots in a Retroviral Shuttle Vector after a Single Replication Cycle: Substitutions, Frameshifts and Hypermutations", *Proc. Natl. Acad. Sci. USA* (1990) 87: 6019–6023.
Pease et al., *PNAS* (1994) 91(11):5022–5026.
Pelletier & Sonnenberg, *Nature* (1988) 334:320–325.
Persidis, *Nature Biotechnology* (1998) 16:100–101.
Persidis, *Nature Biotechnology* (1998) 16:393–394.
Pink et al., "Avian embryos in immunology", in *Immunological Methods* (1985) vol. III, pp. 385–402, Ed. I. Lefkovits & B. Pernis, Academic Press, London.
Plunkett et al., *Nucl. Acids Res.* (1993) 21:3391–3398.
Polson et al., *Immunol. Commun.* (1980) 9:475–493.
Poustka et al., *Cold Spring Harbor Symp. Quant. Biol.* (1986) 51:131–139.
Pouissant et al., *BioTechniques* (1990) 8:148–149.
Sanford, et al., *Technique* (1991) 3:3–16.
Schade et al., "Avian egg yolk antibodies: The egg laying capacity of hens following immunization with antigens of different kinds, origin, and the efficiency of egg yolk antibodies in comparison to mammalian antibodies," *Alternativen zu Tierexperimenten* (1994) 11: 75–84 (abstract).
Schade et al., "The Production of Avian (Egg Yolk) Antibodies: IgY," *ATLA* (1999) 24:925–934.
Schade et al., *ATLA* (1991) 19:403–419.
Schielen et al., *Journal of Immunological Methods* (1995) 188:33–41.
Schultz and Schultz, *Biotechnol. Prog.* (1996) 12(6):729–43.
Shoseyov, O. and Doi, R.H., *Proc. Nat. Acad. Sci. USA.* (1990) 87:2192–2195.
Shoseyov, et al., *Proc. Nat. Acad. Sci. USA.* (1992) 89;3483–3487.
Simmons et al., *J. Immunol.* (1992) 148:267–271.
Soussi et al., *Nucleic Acids Research* (1988) 16:11383.
Southern et al., *Genomics* (1991) 13:1008–10017.
Stewart, *Molecular Medicine Today* (1997) 3(3):93.
Studier et al., *Methods in Enzymol.* (1990) 185:60–89.
Sulston et al., *Nature* (1992) 356:37–41.
Svendsen et al., *Laboratory Animal Science* (1995) 45(1):89–93.
Tietze and Lieb, *Curr. Opin. Chem. Biol.* (1998) 2(3):363–71.
Tomme et al., *Protein Engineering* (1994) 7:117–123.
Van Regenmortel, M.H.V., "Eggs as Protein and Antybody Factories", in *Proceedings of the European Symposium on the Quality of Poultry Meat* (1993), pp. 257–263, INRA, Tours, France.
Vollmer et al. *J Immunol Methods* (1996) 199:47–54.
Wanke et al., "Freundsches Komplettes Adjuvans Beim Huhn: Effiziente Immunostimulation Bei Gravierender Lokaler Inflammatorischer Reaktion," *Journal of Veterinary Medicine* (1996) 43:243–253.
Warr et al., "IgY: Clues to the Origins of Modern Antibodies," *Immunology Today* (1995) 16: 392–398.
Wasinger et al., *Electrophoresis* (1995) 16:1090–1094.
Williams, et al., *Proc. Natl. Acad. Sci.* (1991) 88:2726–2730.
Wilson et al., *Genomics* (1992) 13:1198–1208.
Wu et al., *Cell* (1990) 63:687–695.
Wu et al., *Rapid Commun. Mass Spectrom.* (1993) 7:142–146.
Zhang et al., *J. Virology* (1995) 69:3929–3932.
Zhang & Madden, *Genome Research* (1997) 7:649–656.

* cited by examiner

Name of plasmid: pS&DV
Size of Vector: 3291 bp
Constructed by: Lingxun Duan. GenWay BioTech Inc polilinker region DNA sequence:

ATG g AGATCTTAATTAA GAATTC GCGGCCGC TACCAGGTAAGTG
(SEQ ID NO:22)

*Name of plasmid: pS&DV-S*
*Size of Vector: 3381 bp*
*Constructed by: Lingxun Duan. GenWay BioTech Inc*

S-D: chicken IgY Vh1 secreted domain:
MSPLVSSLLLLAALPRLMAA---inserted protein domain
(SEQ ID NO:24)

polilinker region DNA sequence:

ATGAGCCCACTCGTCTCCTCCCTCCTGCTCCTGGCCGCCCTGCCAGGGCTGATG
GCG GCC *TTAATTAA* GAATTC GCGGCCGC TACCAGGTAAGTG
(SEQ ID NO:23)

Lane 1: IgY purified through PEG precipitation

Lane 2: IgY purified through DEAE-Cellulose

METHODS AND VECTORS FOR GENERATING ANTIBODIES IN AVIAN SPECIES AND USES THEREFOR

This is a continuation-in-part of PCT/US99/26843, filed Nov. 12, 1999, now pending, which claims the benefit of priority under 35 U.S.C. § 119(e) to U.S. Provisional Application Ser. No. 60/108,487, filed Nov. 16, 1998. The disclosures of the above-referenced priority applications are incorporated by reference in its entirety.

TECHNICAL FIELD

The present invention relates to processes for producing polyclonal and monoclonal antibodies to an antigen in an avian species, preferably in a chicken, using polynucleotide vaccination. The present invention also relates to processes for determining the proteomics profile of a set of pre-selected DNA sequences isolated from a bio-sample, preferably the proteomics profile of a human cDNA library. The present invention additionally relates to processes for identifying physiologically distinguishable markers associated with a physiologically abnormal bio-sample. The present invention further relates to antibody arrays, integrated databases for identification of genes and proteins, multi-functional gene expression vectors, and methods of producing and using such antibody arrays, integrated databases and multi-functional gene expression vectors.

BACKGROUND ART

Genetic immunization represents a novel approach to vaccine immune therapeutic development. In comparison with the conventional vaccination, genetic vaccination has the advantages of relatively short development time, case of large-scale production, low development, manufacturing and distribution costs, and better safety for the vaccine producers, administers and receipts.

Genetic vaccination can be divided into DNA vaccination and mRNA vaccination. Recent studies have revealed the following important features of plasmid DNA immunization (Chattergoon et al., FASEB, 1997, 11:753–763). First, different tissues, based on the delivery method (in particular, the muscle and skin), can be transfected in viva by plasmid DNA and serve as productive antigen factories. Second, protective cellular and humoral responses can be induced through a variety of delivery methods in some model systems. Third, only small quantities of plasmid DNA are necessary for antigenic stimulation. The success of plasmid DNA immunization in inducing immune responses to several target antigens through several immunization sites and via several unique delivery techniques solidified the concept of DNA vaccines. This technology has since been applied to many disease models including influenza B, hepatitis B virus, malaria, tuberculosis, SIV and HIV type 1 and various cancers (Id.).

Polyclonal antibodies have traditionally been produced in mammals such as mice, rabbits, sheep, goats, and pigs. The antibodies are obtained from the serum after an immunization period. This technique is invasive, time consuming and costly, involving restraint of and blood sample collection from the animals. In contrast, polyclonal antibody production in chickens, especially with the egg yolk as the antibody source, is a non-invasive technique. The concentration of immunoglobulin in egg yolk may be similar to that of serum (Altchul et al., Nature Genetics, 1994, 6:119–129). In addition, poultry have a lower phylogenetic status than mammals (European Community Directive 86/609 Article 7), and it is therefore desirable to use birds instead of mammals.

It can be difficult to raise antibodies of high specificity against well conserved mammalian proteins. Because of the large evolutionary distance from mammals, chickens can often be used as antibody producers (Burke et al., Science, 1987, 236:806–812). Another advantage of chickens as antibody producers is that the chicken antibodies are often useful in assays of the analogue to the antigen present in other species (Bonaldo et al., Genome Research, 1996, 6:791–806; Buckler et al., Proc. Natl. Acad. Sci., 1991, 88:4005–4009).

Use of chickens for production of antibodies on a large scale is associated with obvious advantages. The cost of keeping chickens is similar to or lower than that of rabbits, by tradition the most popular species for polyclonal antibody production. Thus there is an economic advantage in such a replacement, in addition to the lower number of animals needed. When eggs are used as the antibody source, productivity is much higher than that in mammals. Chickens are obtainable in inbred strains, thus minimizing the genetic variation in antibody response, a problem commonly seen in rabbit antibody production (Bussey, Yeast, 1997, 13(16):1501–1503). No technical assistance is necessary for collection and marking of eggs.

Fynan et al., Proc. Natl. Acad. Sci., 1993, 90:11478–11482, described DNA vaccination of mice and chicken using purified DNA expressing an influenza hemagglutinin glycoprotein. Fynan et al. found that 67–95% of the test mice and 25–63% of test chickens were protected against a lethal influenza challenge. Protections occurred in both mice and chicken that did not have detectable levels of anti-influenza antibodies before challenge. Before challenge, the DNA vaccination and booster inoculations raised non-detectable or very low level of anti-influenza antibodies in mice. No data concerning antibody response in chicken after the DNA vaccination were described.

Kodihalli et al., J. Virol., 1997, 71(5):3391–3396, show that gene gun delivery of DNA encoding an H5 HA protein confers complete immune protection to chickens challenged with lethal H5 viruses. However, within the first 3 weeks post-immunization, no detectable antibodies were found in any of the vaccine groups. In addition, no antibodies to any of the three H5 virus antigens were found following booster immunization of the DNA vaccine group before challenge.

WO 94/24268 discloses recombinant vectors comprising a recombinant avian adenovirus incorporating, and capable of expression of at least one heterologous nucleotide sequence, which is preferably one which encodes an antigenic determinant of infectious bursal disease virus. WO 94/24268 also discloses methods of production of recombinant vectors, methods of preparation of vaccines based on the vectors, administration strategies and methods of protecting poultry from disease. In the methods disclosed therein, chicks were immunized with functional viruses containing the recombinant avian adenovirus. The antibodies thus generated could only be detected by ELISA. WO 94/24268 does not disclose or teach any steps for recovering the antibodies from the immunized chicks, especially steps for recovering such antibodies from egg yolk or B cells from the immunized chicks.

WO 99/02188 discloses egg yolks and egg yolk fractions containing avian antibodies against *Clostridium difficile*, and methods of providing passive immunization for the prevention or treatment of pseudomembranous colitis or diarrhea by means of enteral administration of anti-*Clostridium difficile* yolk antibodies harvested from the eggs of hyperimmunized avian hens. The *Clostridium difficile* antigens used to generate the immune response in hens are somatic antigens, i.e., whole cell antigens, or toxoids of toxins A or B or combinations thereof. WO 99/02188 does not disclose or teach immunization of hens with nucleic acids.

According to databases based on expressed sequence tags (ESTs), the human genome consists of about 60,000–100,000 genes, scattered among 3–4 billion nucleotides of chromosome-based DNA code, the sequencing of which could be completed as early as 2005 (James, *Biochem. Biophys. Res. Comm.*, 1997, 231:1–6). However, DNA sequence information provides only a static snapshot of all the possible ways a cell might use its genes. Therefore, this enormous amount of static DNA sequence information needs to be correlated with dynamic information about gene products and their interactions in order to provide meaningful insight for fundamental biological processes and applications of such insight into various fields.

The word proteome was first introduced in July 1995 and was defined as the "total protein complement of a genome" (Wasinger et al., *Electrophoresis*, 1995, 16:1090–1094). Proteomics aims to supplement gene sequence data with information on what proteins are being made where, in what amounts, and under what conditions (Persidis, *Nature Biotechnology*, 1998, 16:393–394). It aims to show how protein cascades inside cells change as a result of specific diseases, thereby identifying novel potential drug targets. It then aims to validate particular drug leads against those targets by providing information on how those leads affect the proteome cascades (Persidis, *Nature Biotechnology*, 1998, 16:100–101). Therefore, in addition to providing answers to fundamental questions about the molecular basis of a cell's state at any point in time, proteomics promises to accelerate novel drug discovery through automated analysis of clinically relevant molecular phenomena.

In view of the fast development in the genomic research, proteomic research is lagging behind. For example, the proteomic characteristics, including the existence, quantity, cellular location and tissue or developmental expression specificity, of the majority of the proteins putatively encoded by the presently known human DNA sequences have not been characterized. Although the currently available large-format 2DE is capable of producing gels containing up to 10,000 distinct protein and peptide spots, over 95% of the spots separated by such 2-DE gel cannot be sequenced because they are beyond the limits of current high-sensitivity Edman sequencing technology (Persidis, *Nature Biotechnology*, 1998, 16:393–394).

Specific antibodies, if available, are powerful tools for proteomic research. Antibodies are conventionally generated by protein or peptide vaccination of mammals such as mice, rabbits, rats or sheep. However, such vaccination is time consuming and costly. Therefore, due to the vast number of the known DNA sequences to be characterized, it is virtually impossible to use the conventional protein or peptide vaccination technology to generate antibodies for large-scale proteomic research.

Given the great interest in the proteomic research and the usefulness of antibodies in the proteomic research, there is a great need for a fast and economically feasible method for generating antibodies to be used in large-scale proteomic research. The present application addresses this and other needs in the art.

Citation of the references hereinabove shall not be construed as an admission that such references are prior art to the present invention.

DISCLOSURE OF THE INVENTION

The invention described herein encompasses a process for producing antibodies to an antigen in an avian species, which comprises: 1) delivering to said avian species a DNA sequence encoding said antigen operatively linked to a promoter, said promoter being capable of directing expression of said antigen in said avian species, or a mRNA sequence encoding said antigen, in a amount sufficient to induce detectable production of said antibodies to said antigen; and 2) recovering said antibodies from said avian species. Preferably, the avian species being vaccinated is a chicken or quail and the antibodies are recovered from egg yolk of the chicken or quail.

The present invention also encompasses a process for producing a monoclonal antibody to an antigen in an avian species, which comprises: 1) delivering to said avian species a DNA sequence encoding said antigen operatively linked to a promoter, said promoter being capable of directing expression of said antigen in said avian species, or a mRNA sequence encoding said antigen, in a amount sufficient to induce detectable production of said antibodies to said antigen; 2) removing at least a portion of antibody-producing cells from said avian species; 3) immortalizing said removed antibody-producing cells; 4) propagating said immortalized antibody-producing cells; and 5) harvesting said monoclonal antibody produced by said immortalized antibody-producing cells. Preferably, the avian species used herein is chicken. More preferably, the chicken antibody-producing cells are immortalized by fusing with cells of a chicken B lymphoblastoid cell line or by oncogene transformation.

The present invention additionally encompasses a vector for expressing genes in avian and bacterial cells, which comprises the plasmid depicted in FIGS. 3A & 3C; and a vector for immortalizing chicken antibody-producing cells, which comprises the plasmid depicted in FIG. 12.

The present invention further encompasses a process for assessing the proteomics profile of a set of pre-selected DNA sequences isolated from a bio-sample, which comprises: 1) cloning each of said DNA sequences into a dual-expression vector that is capable of expressing said DNA sequences in avian cells, non-avian cells or in vitro expression systems; 2) delivering said DNA sequence in said dual-expression vector formed in step 1), or mRNA or protein encoded by said DNA sequence, or a mixture thereof, to an avian species in an amount sufficient to induce detectable production of antibodies to an antigen encoded by said DNA sequence, and recovering said antibodies from said avian species; 3) delivering said DNA sequence, or mRNA encoded by said DNA sequence, or a mixture thereof, which is delivered to said avian species in step 2), to said non-avian cells, and recovering proteins or peptides encoded by said DNA sequence from said non-avian cells, or expressing and recovering proteins or peptides encoded by said DNA sequence in said in vitro expression systems; 4) conducting immunoreactions between said antibodies recovered in step 2) with said proteins or peptides recovered from step 3) to characterize the immunospecificity of said antibodies; and 5) conducting immunoreactions between said antibodies recovered in step 2) with said bio-samples to determine the proteomics profile of said set of pre-selected DNA sequences.

The present invention further encompasses an array of antibodies attached on a solid surface. Preferably, the antibodies used in the array specifically bind substantially to proteins or peptides encoded by a set of pre-selected DNA sequences isolated from a bio-sample.

The present invention further encompasses a method for assessing proteomics profile of a biosample, which method comprises: 1) dividing a plurality of antibodies into an unlabelled portion and a labeled portion; 2) attaching the unlabelled antibodies on a solid surface to form an array of unlabelled antibodies on said solid surface; 3) contacting said array of unlabelled antibodies formed in step 2) with a biosample to retain antigens contained in said biosample that specifically bind to said unlabelled antibodies; 4) detecting said retained antigens by contacting said retained antigens with said labeled antibodies, thereby proteomics profile of said biosample is assessed.

The present invention further encompasses an integrated database for identification of genes and proteins, which integrated database comprises a genomic sequence subdatabase, a cDNA sequence subdatabase, a dual expression vector subdatabase which provides information for a plurality of vectors that are capable of directing expression in an avian species and in a non-avian species or an in vitro expression system, a protein sequence subdatabase, an antibody subdatabase and means for linking information in one subdatabase to information in other subdatabases, wherein said genomic DNA sequences, cDNA sequences, dual expression vectors, proteins or peptides and avian antibodies correspond to each other according to the central dogma and antigen-antibody binding specificity. Preferably, the dual expression vector directs expression in an avian species and in a non-avian species such as a bacterium, a yeast or a mammal. Also preferably, the antibody subdatabase provides information for a plurality of IgY antibodies produced in the avian species.

The present invention further encompasses a method for generating an integrated library for identification of genes and proteins, which method comprises: 1) selecting and marking a plurality of DNA sequences from a genomic library; 2) selecting and marking a plurality of cDNA sequences from a cDNA library that correspond to said selected and marked plurality of genomic DNA sequences; 3) cloning said plurality of selected and marked cDNA sequences into a dual expression vector that is capable of directing expression of said plurality of selected and marked cDNA sequences in an avian species and in a non-avian species or an in vitro expression system; 4) producing a plurality of proteins or peptides encoded by said plurality of selected and marked cDNA sequences by delivering and expressing said dual vector containing said plurality of selected and marked cDNA sequences into said non-avian species or said in vitro expression system; and 5) generating antibodies from an avian species using said dual vector formed in step 3) via nucleic acid vaccination or using proteins or peptides formed in step 4) via protein or peptide vaccination, thereby forming an integrated library comprising a plurality of genomic DNA sequences, a plurality of cDNA sequences, a plurality of dual expression vectors containing said plurality of cDNA sequences, a plurality of proteins or peptides encoded by said genomic DNA or cDNA sequences, and a plurality of avian antibodies that specifically bind to proteins or peptides encoded by said genomic DNA or cDNA sequences, and wherein said genomic DNA sequences, cDNA sequences, dual expression vectors, proteins or peptides and avian antibodies correspond to each other according to the central dogma and antigen-antibody binding specificity. Preferably, the method further comprises a step of conducting immunoreactions between said antibodies generated in step 5) with said proteins or peptides generated in step 4) to characterize the immunospecificity of said antibodies. Also preferably, the method further comprises a step of conducting immunoreactions between said characterized antibodies with a biosample from which genomic library is isolated to determine the proteomics profile of the selected and marked plurality of genomic DNA sequences.

The present invention further encompasses a method for generating an integrated database for identification of genes and proteins, which method comprises: 1) delivering bioimformatic information of the plurality of genomic DNA sequences, the plurality of cDNA sequences, the plurality of dual expression vectors, the plurality of proteins or peptides, and the plurality of avian antibodies obtained using the above-described methods into the corresponding genomic DNA, cDNA, dual expression vector, protein or peptide, and the avian antibody subdatabases; and 2) providing means for connecting the bioimformatic information from one subdatabase to any or all of the other subdatabases. Preferably, the method further comprises a step of delivering bioimformatic information of the immunospecificity of the avian antibodies obtained using the methods described in the following Section C into the integrated database. Also preferably, the method further comprises a step of delivering bioimformatic information of the proteomics profile of the selected and marked plurality of genomic DNA sequences, which can be obtained according to the methods described in the following Section C, into the integrated database.

The above described processes, methods, antibody arrays and integrated libraries or databases for identification of genes and proteins can be used for identifying physiologically distinguishable markers associated with a physiologically abnormal biosample, or for identifying substances that modulate proteomics profile of a biosample.

MODES OF CARRYING OUT THE INVENTION

Figure 1:
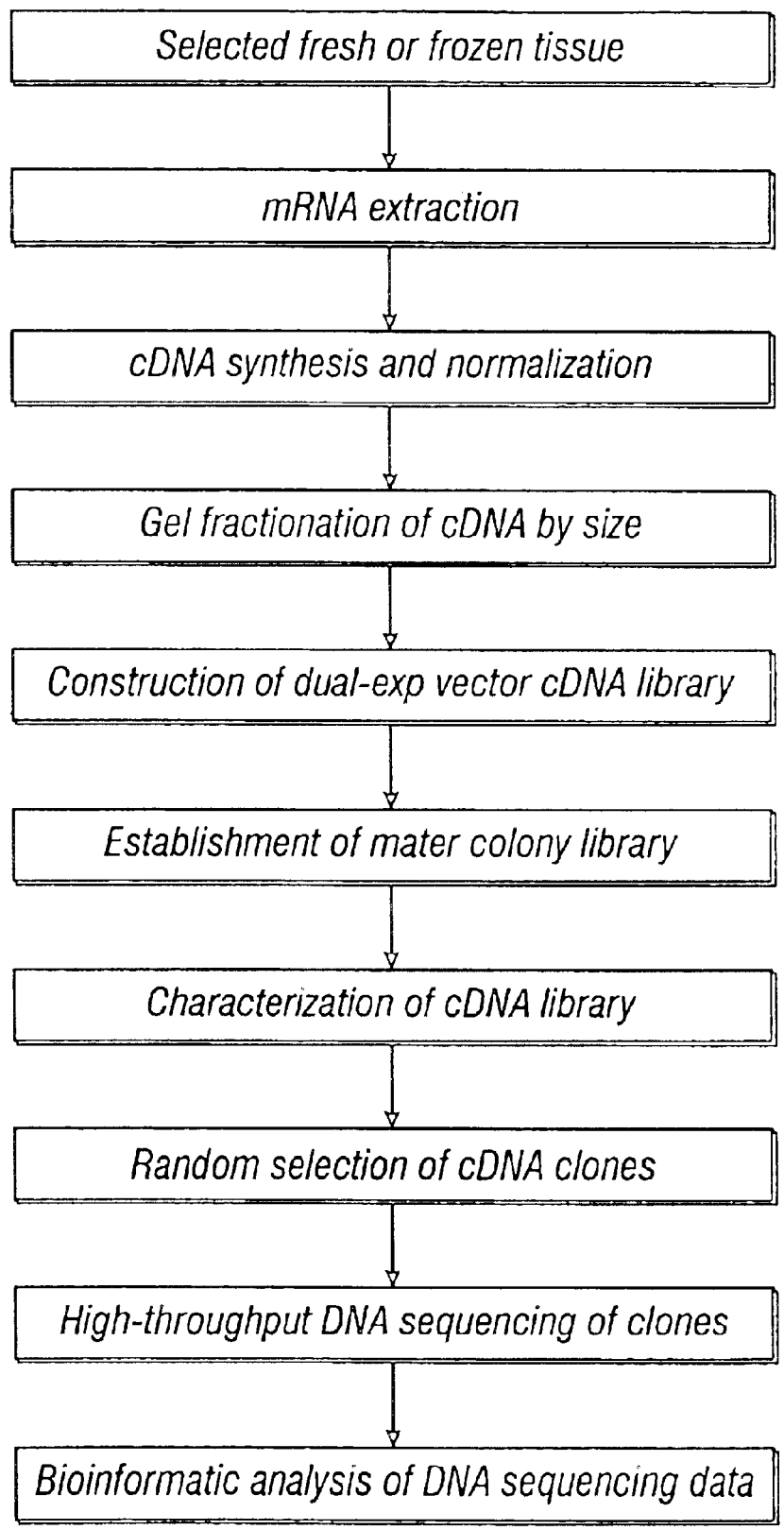
FIG. 1 depicts a method for selecting DNA clone of interest.
Figure 2:
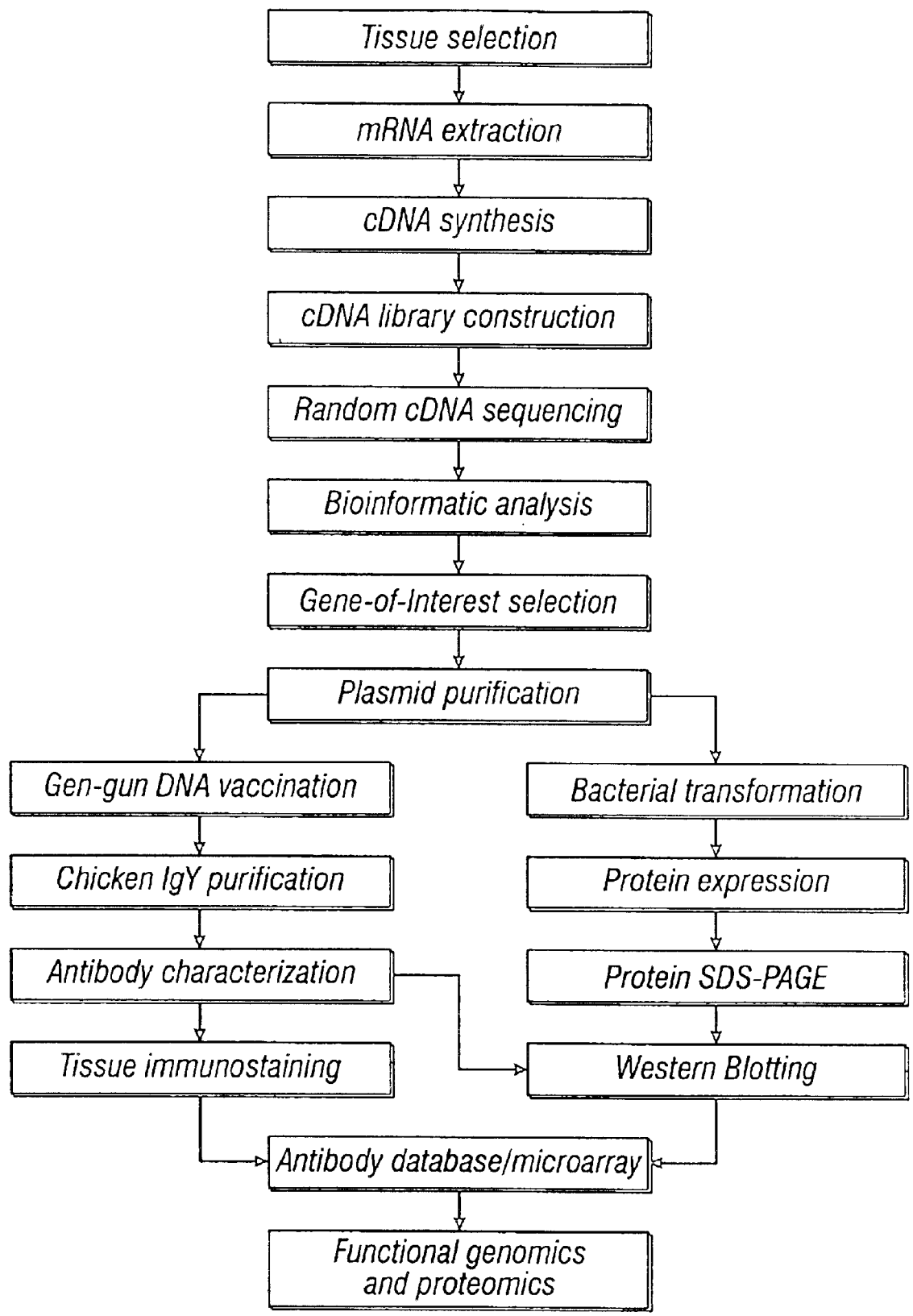
FIG. 2 depicts a diagram of the antibody assisted method for identification of gene and protein (AMIGAP).

In addition to their therapeutic importance in medicine, monoclonal and polyclonal antibodies are of great value in biological research such as gene functional analysis, where they serve as essential components in a variety of diagnostic systems used for the qualitative and quantitative determination of a wide range of specific gene coded protein expression. It is not surprising, therefore, that the growing interest in alternative methods has focused not only on the quality control of antibodies, but also on the methods used for the production of antibodies on the industrial large-scale for the high-throughput screening of gene function.

Antibody production normally requires the use of laboratory animals (mostly rabbits, but also mice, rats and guinea pigs) or larger mammals, such as horses, sheep, and goats. The procedure involves two steps, each of which not only causes distress to the animals involved but also is very expensive and labor intensive: a) the immunization itself; and b) bleeding, which is a prerequisite for antibody preparation.

The use of avian species such as chickens or quail for antibody production, as opposed to mammals, represents both a refinement and a reduction in animal use. It is a refinement in that the second painful step, i.e., the collection of blood, can be replaced by antibody extraction from egg yolk. It entails a reduction in the number of animals used because chickens produce larger amounts of antibodies than laboratory rodents. In fact, it has been known that the immunization of a chicken induces the production of similar concentrations of specific antibodies in both egg yolk and serum.

The use of antibodies produced from an avian species, e.g., chicken, can be advantageous in certain circumstances. First, the immune response in an antibody-producing animal tends to increase as its phylogenetic difference with the animal used as the antigen source increases. Thus, chicken antibodies recognize more epitopes on a mammalian protein than the corresponding rabbit antibody does, making it advantageous to use IgY in immunological assays of mammalian proteins. This is especially true when the antigen is a highly conserved protein, such as a hormone. Moreover, if a secondary antibody of mammalian origin is used, the phylogenetic difference will result in a further amplification, since three to five times more of the secondary antibody will bind to chicken IgY than occurs with rabbit IgG. Accordingly, there is a growing need for secondary antibodies to IgY, labeled with different markers (enzymes, fluorescent markers), to be made available commercially, such as the monoclonal antibodies to chicken IgY which are available from Connex (Munich, Germany) and ID-DLO (Lelystad, The Netherlands). Another advantage of chicken IgY over mammalian antibodies is that it does not activate the complement system; the latter has been shown to reduce antigen binding and cause false negative results. Chicken IgY does not react with anti-mammalian antibodies in human serum, such as rheumatoid factors and human anti-IgG. In immunological assays, the interference caused by these antibodies can be problematic, particularly as the sensitivity of the assay increases. Thus, if chicken IgY is used, interference by anti-mammalian IgG antibodies can be eliminated. Chicken IgY does not bind to human or bacterial Fc-receptors, such as Staphylococcal protein-A or Streptococcal protein-G. Thus, IgY can be used for microbiological assays without the risk of interference by Fc-receptors.

Despite the previous failures of generating antibodies by DNA vaccination in chicken, present applicant has discovered surprisingly that polynucleotide vaccination can be used to generate desired antibodies in an avian species. Accordingly, the present invention encompasses processes for producing desired antibodies in an avian species using polynucleotide vaccination, processes for determining the proteomics profile of a set of pre-selected DNA sequences isolated from a bio-sample and processes for identifying physiologically distinguishable markers associated with a physiologically abnormal bio-sample using the antibodies generated by the polynucleotide vaccination of an avian species. Antibody arrays and integrated databases for identification of genes and proteins, and their uses in proteomics studies and other fields are further provided.

Unless defined otherwise, all technical and scientific terms used herein have the same meaning as is commonly understood by one of ordinary skill in the art to which this invention belongs. All patents, applications, published applications and other publications and sequences from GenBank and other data bases referred to herein in any section of this application are incorporated by reference in their entirety.

For clarity of disclosure, and not by way of limitation, the detailed description of the invention is divided into the subsections which follow.

A. Processes for Producing Antibodies in an Avian Species by Polynucleotide Vaccination The present invention provides a process for producing antibodies to an antigen in an avian species, which comprises: 1) delivering to said avian species a DNA sequence encoding said antigen operatively linked to a promoter, said promoter being capable of directing expression of said antigen in said avian species, or a mRNA sequence encoding said antigen, in a amount sufficient to induce detectable production of said antibodies to said antigen; and 2) recovering said antibodies from said avian species.

In a preferred embodiment, the avian species to be vaccinated is selected from the group consisting of a chicken (*Gallus*), a quail (*Coturnix*), a turkey (*Meleagris gallopavo*), a duck, a goose and a Japanese quail (*Coturnix japonica*). More preferably, the avian species to be vaccinated is a chicken or a quail.

Examples of other names of chicken include, but are not limited to, *Gallus* (*G. domesticus*), chick and hen. Such synonyms are encompassed by the present invention. For consistency, and not for limiting the scope of the presently claimed invention, only the name "chicken" is used herein.

For purposes described herein, keeping chickens in cages under laboratory conditions is advantageous, in that the chickens can be readily located and their health can be easily monitored. By keeping a brown and a white hen together in one cage, the eggs can be identified unequivocally.

Antibodies can be produced by using chickens bred for commercial egg production as well as by using chickens which have been bred free from specific pathogens (SPF chickens). It is preferable to use chickens used for breeding purposes than those used for egg production, because the health status of breeding animals is often better controlled.

SPF chickens can be obtained from some commercial suppliers in Europe (for example, F. E. Lohmann, Cuxhaven, Germany) and in the United States (for example, Spafas Inc., Preston, Conn.). Adult SPF chickens are relatively difficult to obtain, and therefore usually have to be raised in the laboratory. Eggs from genetically defined flocks can be obtained from several sources (Pink, J. R. L., Jotereau, F., Houssant, E. & Weber, W. T. (1985), *Avian embryos in immunology. In Immunological Methods, Volume III* (ed. I. Lefkovits & B. Pernis), pp. 385–402. London: Academic Press.). Commercial laying chickens are not only cheaper to purchase, but they can also be obtained just before they come into production, thereby further reducing the costs associated with antibody production. The advantage of using SPF over egg laying chickens is that the former generally give higher antibody titers.

Another important consideration is the egg laying capacity of the chicken, and the possible factors which may affect this. One such factor could be immunization using Freund's complete adjuvant (FCA), or the antigen itself. According to some reports, FCA does not influence egg production as much as the antigen itself, as has been shown, for example, for substances from Ascaris suum (.Schade, R., Bürger, W., Schöneberg, T., Schniering, A., Schwarzkopf, C., Hlinak, A. & Kobilke, H. (1994). Avian egg yolk antibodies. The egg laying capacity of hens following immunization with antigens of different kinds, origin, and the efficiency of egg yolk antibodies in comparison to mammalian antibodies. Alternativen zu Tierexperimenten 11: 75–84); the results of this study indicated that the egg laying capacity is influenced primarily by events other than immunization.

The DNA or mRNA sequence can be delivered to the interstitial space of tissues of the animal body, including those of muscle, skin, brain, lung, liver, spleen, bone marrow, thymus, heart lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers or organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation of the lymph fluid of the lymphatic channels.

The DNA or mRNA sequence can be conveniently delivered by injection into the tissues comprising these cells. They are preferably delivered to and expressed in persistent, non-dividing cells which are differentiated, although delivery and expression can be achieved in non-differentiated or less completely differentiated cells, such as, for example, stem cells of blood or skin fibroblasts.

In a specific embodiment, the DNA or mRNA sequence is delivered directly to a tissue of the avian species. Preferably, the DNA or mRNA sequence is delivered directly to muscle, skin or mucous membrane. Delivery to the interstitial space of muscle tissue is preferred because muscle cells are particularly competent in their ability to take up and express polynucleotides.

The DNA or mRNA sequence can be delivered directly to a tissue of the avian species by injection, by gene gun technology or by lipid mediated delivery technology. The injection can be conducted via a needle or other injection devices. The gene gun technology is disclosed in U.S. Pat. No. 5,302,509 and the lipid mediated delivery technology is disclosed in U.S. Pat. No. 5,703,055, the contents of which are incorporated herein by reference.

In still another specific embodiment, the DNA or mRNA sequence is delivered to a cell of the avian species and said cell containing the DNA or mRNA sequence is delivered to a suitable tissue of the avian species. Preferably, the DNA or mRNA sequence is delivered to a blood cell of an avian species. More preferably, the DNA or mRNA sequence is delivered to a spleen B cell of an avian species.

The DNA or mRNA sequence can be delivered to the cells of an avian species by a number of methods (see generally Koprowski & Weiner, DNA vaccination/genetic vaccination, 1998. Springer-verlag Berlin Heidelberg) including $Ca_3(PO_4)_2$-DNA transfection (Sambrook et al., *Molecular Cloning*, 2nd Edition, Plainview, N.Y. Cold Spring Harbor Press, 1989), DEAE dextran-DNA transfection (Sambrook et al., *Molecular Cloning*, 2nd Edition, Plainview, N.Y. Cold Spring Harbor Press, 1989), electroporation (e.g., protocols from Bio-Rad), transfection using "LIPOFECTIN"™ reagent (1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water) (e.g., protocols from BRL-Life Science), gene gun technology (U.S. Pat. No. 5,302,509), or viral gene delivery system (Kaplitt et al., Viral Vectors, Academic Press, Inc., 1995).

The gold-particle based gene gun delivery is the preferred method for delivering the DNA or mRNA sequences (U.S. Pat. No. 5,302,509). In a specific embodiment, Bio-Rad helios gene gun system is used in the DNA vaccination procedure. (BIO-RAD Inc. New England). The helios gene gun is a convenient, hand-hold device that provides rapid and direct gene transfer in vivo. The device employs an adjustable, helium pulse to sweep DNA coated gold microcarriers from the inner wall of a small plastic cartridge directly into the target cells. The tubing prepstation and tubing cutter provide a simple way to prepare 50 cartridge "bullets" at a time.

In still another specific embodiment, a DNA sequence encoding the antigen operatively linked to a promoter, which is capable of directing expression of the antigen in the avian species, is delivered. Preferably, the DNA sequence to be delivered is a plasmid.

The promoter to be used can be an endogenous promoter of the avian species such as chicken actin promoter. Alternatively, the promoter can be an exogenous promoter, such as a viral promoter, which is capable of directing expression of the antigen in avian species. Preferably, the viral promoter is RSV LTR, MPSV LTR, SV40 IEP, CMV IEP, metallothionein promoter (U.S. Pat. No. 5,703,055) or spleen necrosis virus LTR (SNV LTR) (U.S. Pat. No. 5,703,055).

In yet another specific embodiment, the DNA sequence used to vaccinate the avian species further comprises a sequence that directs secretion of the encoded antigen in the avian species. Preferably, the secretion-directing sequence is a leader sequence. More preferably, the leader sequence is an endogenous leader sequence of the avian species such as the leader sequence of VH1 of chicken IgY (Kabat et al., Sequences of Proteins of Immunological Interests, 1983, U.S. Department of Health and Human Services, Washington, D.C.), chicken *Secreted Protein, Acidic. Rich in Cysteine* (SPARC) (GenBank Accession No. L24906; Bassuk et al., *Eur. J. Biochem.*, 1993, 218(1):117–127), chicken serum albumin (GenBank Accession No. V00381 and J00806; Hache et al., *J. Biol. Chem.*, 1983, 258(7):4556–4564) and chicken tissue-type plasminogen activator (tPA) (GenBank Accession No. U31988). Although endogenous avian leader sequence is preferred, other types of leader sequences can be used in the present invention. In addition to the leader sequence, cell-membrane-directing sequence of any known membrane proteins can used. Examples of such cell-membrane-directing sequence include, but are not limited to, that of IL-1, CD4 and MHC.

In yet another specific embodiment, a mRNA sequence encoding the antigen is delivered.

The polynucleotide material to be delivered according to the present invention can take any number of forms, and the present invention is not limited to any particular polynucleotide coding for any particular polypeptide. In preferred embodiments, the DNA sequence or the mRNA sequence encoding the antigen is not contained and delivered in a viral vector, such as a viral vector derived from an adenovirus. Also preferably, substantially naked DNA sequence or mRNA sequence are used as immunogens.

With the availability of automated nucleic acid synthesis equipment, both DNA and RNA can be synthesized directly when the nucleotide sequence is known by a combination of PCR cloning and fermentation. Moreover, when the sequence of the desired polypeptide is known, a suitable coding sequence for the polynucleotide can be inferred.

As disclosed in U.S. Pat. No. 5,703,055, when the polynucleotide to be used is mRNA, it can be readily prepared from the corresponding DNA in vitro. For example, conventional techniques utilize phage RNA polymerase SP6, T3, or T7 to prepare mRNA from DNA templates in the presence of the individual ribonucleoside triphosphate. An appropriate phage promoter, such as a T7 origin of replication site can be placed in the template DNA immediately upstream of the gene to be transcribed. Systems utilizing T7 in this manner are well known, and are described in the literature, e.g., in Current Protocols in Molecular Biology, §3.8 (vol. 1 1988).

One particularly preferred method for obtaining the mRNA used in the present invention is the use of pXGB plasmid or any similar plasmid that can be readily constructed by those of ordinary skill in the art and can be used with a virtually unlimited number of cDNAs in practicing the present invention (U.S. Pat. No. 5,703,055). Such plasmids may advantageously comprise a promoter for a desired RNA polymerase, followed by a 5' untranslated region, a 3' untranslated region, and a template for a poly A tract. There should be a unique restriction site between these 5' and 3' regions to facilitate the insertion of any desired cDNA into the plasmid. Then, after cloning the plasmid containing the desired gene, the plasmid is linearized by cutting in the polyadenylation region and is transcribed in vitro to form mRNA transcripts. These transcripts are preferably provided with a 5' cap. Alternatively, a 5' untranslated sequence such as EMC can be used which does not require a 5' cap.

While the foregoing represents a preferred method for preparing the mRNA, it will be apparent to those of skill in the art that many alternative methods also exist. For example, the mRNA can be prepared in commercially-available nucleotide synthesis apparatus. Alternatively, mRNA in circular form can be prepared. Exonuclease-resistant RNAs such as circular mRNA, chemically blocked mRNA, and mRNA with a 5' cap are preferred, because of their greater half-life in vivo.

In particular, one preferred mRNA is a self-circularizing mRNA having the gene of interest preceded by the 5' untranslated region of polio virus (U.S. Pat. No. 5,703,055). It has been demonstrated that circular mRNA has an extremely long half-life (Harland & Misher, *Development*, 1988, 102:837–852; Pelletier & Sonnenberg, *Nature*, 1988, 334:320–325. This material may be prepared from a DNA template that is self-splicing and generates circular "lariat" mRNAs, using the method of Been & Cech, *Cell*, 1986, 47:206–216. The contents of these articles are hereby incorporated herein by reference.

Also as disclosed in U.S. Pat. No. 5,703,055, the present invention includes the use of mRNA that is chemically blocked at the 5' and/or 3' end to prevent access by RNase. (This enzyme is an exonuclease and therefore does not cleave RNA in the middle of the chain.) Such chemical blockage can substantially lengthen the half life of the RNA in vivo. Two agents which may be used to modify RNA are available from Clonetech Laboratories, Inc. Palo Alto, Calif.: C2 AminoModifier (Catalog #5204-1) and Amino-7-dUTP (Catalog #K1022-1). These materials add reactive groups to the RNA. After introduction of either of these agents onto an RNA molecule of interest, an appropriate reactive substituent can be linked to the RNA according to the manufacturer's instructions. By adding a group with sufficient bulk, access to the chemically modified RNA by RNase can be prevented.

In yet another specific embodiment, a chicken is vaccinated and the antibodies are recovered from egg yolk of the chicken. Preferably, the antibodies are purified from the egg yolk by ammonium sulfate precipitation, by polyethylene glycol 6000 precipitation or by caprylic acid precipitation.

The main type of immunoglobulin (Ig) isolated from egg yolk of an avian species, e.g., chicken, is generally referred to as "IgY"; other Ig classes are present, but only in negligible amounts. Structurally, IgY is identical to the major Ig found in serum, but it is different from mammalian IgG (see Schade et al., *ATLA*, 19: 403–419) for detailed comparison between avian IgY and mammalian IgG).

Historically, the low molecular weight (MW) Ig found in avian serum was known as IgG, by analogy with its mammalian counterpart. It has become clear, however, that this is inappropriate due to the fundamental structural differences between IgG and IgY. In fact, no IgG-like antibody with a heavy y chain of 50,000 Da has been found in the chicken (.Warr, G. M., Magor, K. E. & Higgens, D. A. (1995). *IgY: clues to the origins of modern antibodies. Immunology Today* 16: 392–398.). The term IgY was originally coined to refer to the larger MW Ig found in egg yolk, but it is now accepted that IgY is the major antibody in both the blood and yolk.

The heavy (y) chain of IgG consists of four domains: the variable domain (VH) and three constant domains (Cy1, Cy2 and Cy3). The Cy1 domain is separated from Cy2 by a hinge region, which gives considerable flexibility to the Fab fragments. In contrast, the heavy chain of IgY (v) has a MW of 65,000 Da, does not have a hinge region, and possesses four constant domains (Cv1–Cv4) in addition to the variable domain. Sequence comparisons between IgG and IgY have shown that the Cy2 and Cy3 domains of IgG are closely related to the Cv3 and Cv4 domains, respectively, of IgY, while the equivalent of the Cv2 domain is absent in the g chain, having been replaced by the hinge region (Warr, G. M., Magor, KE. & Higgens, D. A. (1995). *IgY: clues to the origins of modern antibodies. Immunology Today* 16: 392–398.).

Methods for recovering antibodies from chicken egg yolk are well known in the art. Several methods can be used for the extraction of IgY from egg yolk, and commercial extraction kits are available (van Regenmortel, M. H. V. (1993). *Eggs as protein and antibody factories. In Proceedings of the European Symposium on the Quality of Poultry Meat*, pp. 257–263. Tours, France: INRA). One of the most frequently used procedures involves protein precipitation with ammonium sulfate, dextran sulfate or polyethyleneglycol (PEG); separation by ion exchange chromatography is also used. There is, in fact, a surplus of effective extraction methods (Lösch, U., Schranner, I., Wanke, R. & Jürgens, L. (1986). *The chicken egg, an antibody source. Journal of Veterinary Medicine* B33: 609–619.), which could be problematic in that potential users of IgY technology may have no rational basis for choosing one method rather than another. In practice, the choice of a specific extraction procedure is usually influenced by the intended application of the antibody, as well as by the experience of the laboratory concerned.

A particularly efficient method consists of two successive precipitations in PEG, by using 3.5% PEG to remove fatty substances, and then 12% PEG to precipitate the IgY.

An improvement of this method incorporates an emulsification step, adding one volume of chloroform to one volume of egg yolk, rather than using the 3.5% PEG precipitation step (18, 19). It is generally assumed that about 100 mg of IgY can be recovered per egg yolk. There are commercial IgY purification kits available such as Promega Inc ( Madison Wis. USA) EGGstract IgY purification system (Cat #: G1531). from PIERCE Inc. (ROCKFORD, IL, USA). EGGCELLENT chicken IgY Purification Kit ( Cat #:44918).

Another example is disclosed in Svendsen et al., *Laboratory Animal Science*, 1995, 45(1):89–93, the content of which is incorporated by reference. According to Svendsen, eggs are collected daily. The yolk is separated from the white by a domestic egg separator and is washed thoroughly with water to avoid contamination with egg white proteins. The yolk membrane is punctured and the yolk is collected. The yolk is diluted several times with distilled water before storage at $-20°$ C. until further purification of the immunoglobulins. To remove yolk lipids, the frozen diluted egg yolk is thawed at room temperature and is centrifuged and filtered to remove the precipitated lipid fraction. This yolk solution is concentrated to the original volume of the yolk by placing the solution in a dialysis tube and removing the water with solid polyethylene glycol 20000.

For ammonium sulfate precipitation, the precipitation is carried out by adding solid AmS to the yolk solution under stirring. To find the optimal precipitation condition, the AmS concentration can be increased stepwise to 50% (e.g., 0 to 10%, 10 to 20%, 20 to 25%, 25 to 30%, 30 to 40%, 40 to 50%). After an incubation period at room temperature, the solution is centrifuged. The pellet is dissolved in phosphate-buffered saline (PBS) containing sodium azide ($NaN_3$) to avoid microbial growth, and the supernatant is used for the next precipitation step.

For polyethylene glycol precipitation, the precipitation is carried out by stirring solid polyethylene glycol 6000 (PEG) into the yolk solution. To find the optimal precipitation condition, the polyethylene glycol concentration can be increased stepwise to 12% (e.g., 0 to 2%, 2 to 4%, 4 to 6%, 6 to 8%, 8 to 10%, 10 to 12%). After an incubation period at room temperature, the solution is centrifuged. The pellet is dissolved in PBS containing $NaN_3$. The supernatant is collected and used for the next precipitation step.

For caprylic acid precipitation, the yolk solution is diluted with acetate buffer. Caprylic acid (CA) is stirred into the solution to a final concentration of 0.02, 0.05, 0.1, 0.5, or 1%. After an incubation period at room temperature, the solution is centrifuged. The pellet is dissolved in PBS containing $NaN_3$.

In yet another specific embodiment, a chicken is vaccinated and the antibodies are recovered from antibody-producing B cells of the chicken, preferably from spleen B cells.

Although the presently claimed processes can be used to generate antibodies to any protein or peptide antigens, the presently claimed processes can preferably be used to generate antibodies to secreted protein or peptide antigens.

Figure 3A:
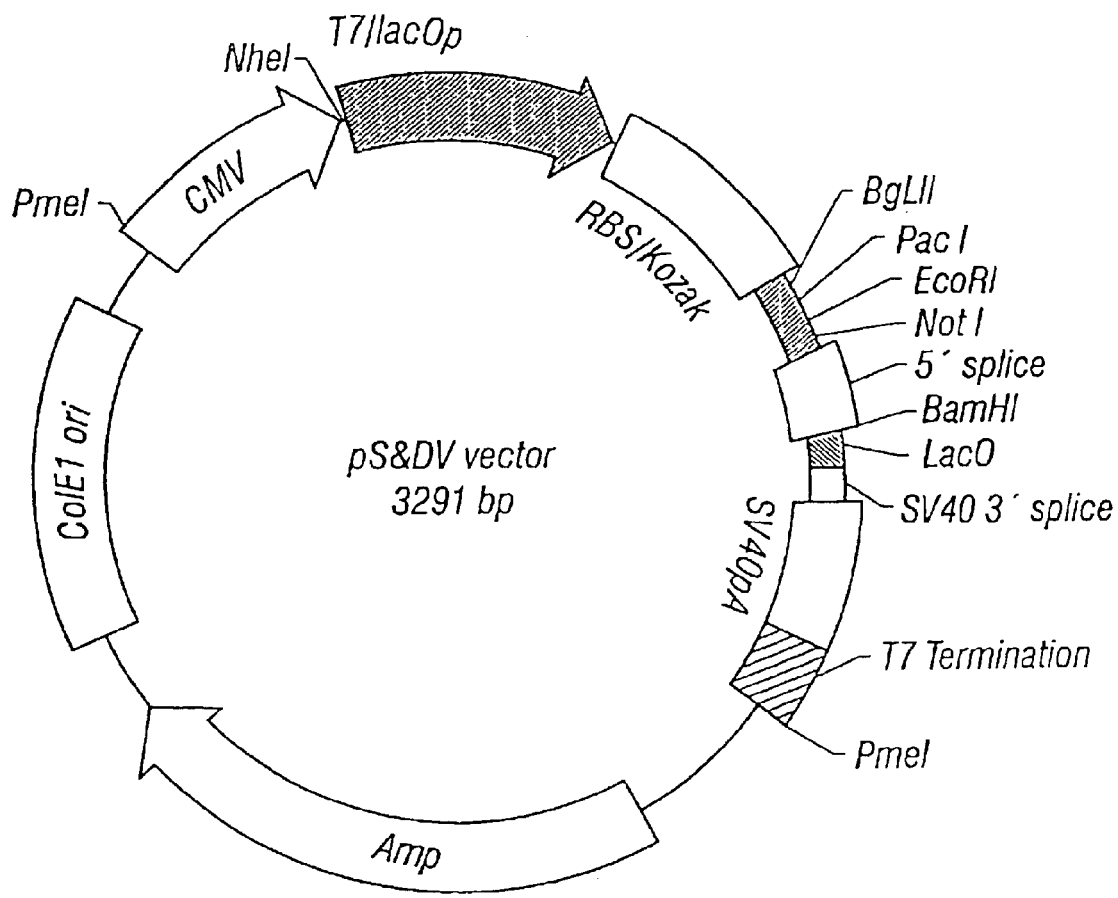
FIG. 3A depicts restriction map of pS&DV.
Figure 3B:
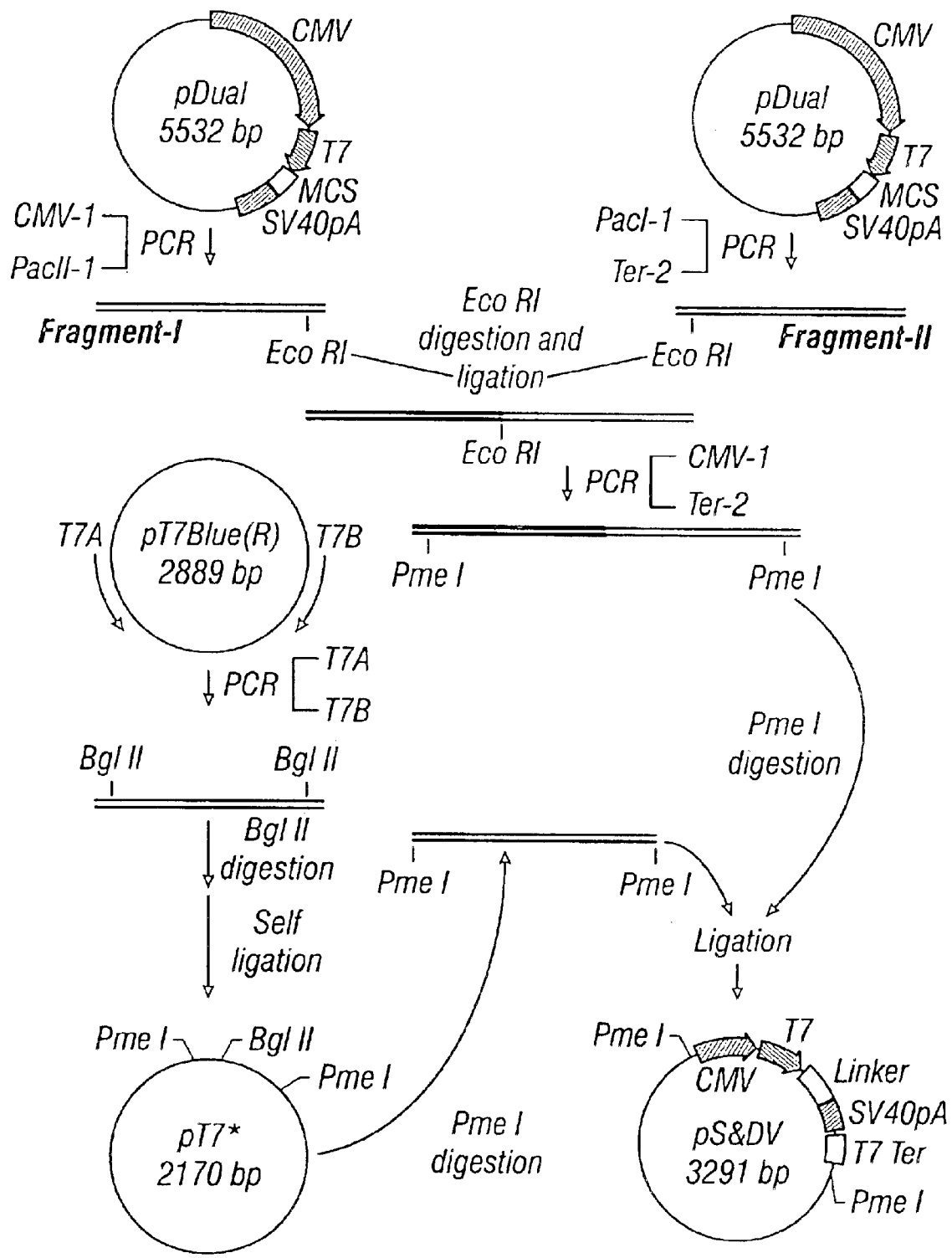
FIG. 3B depicts the construction pS&DV.
Figure 3C:
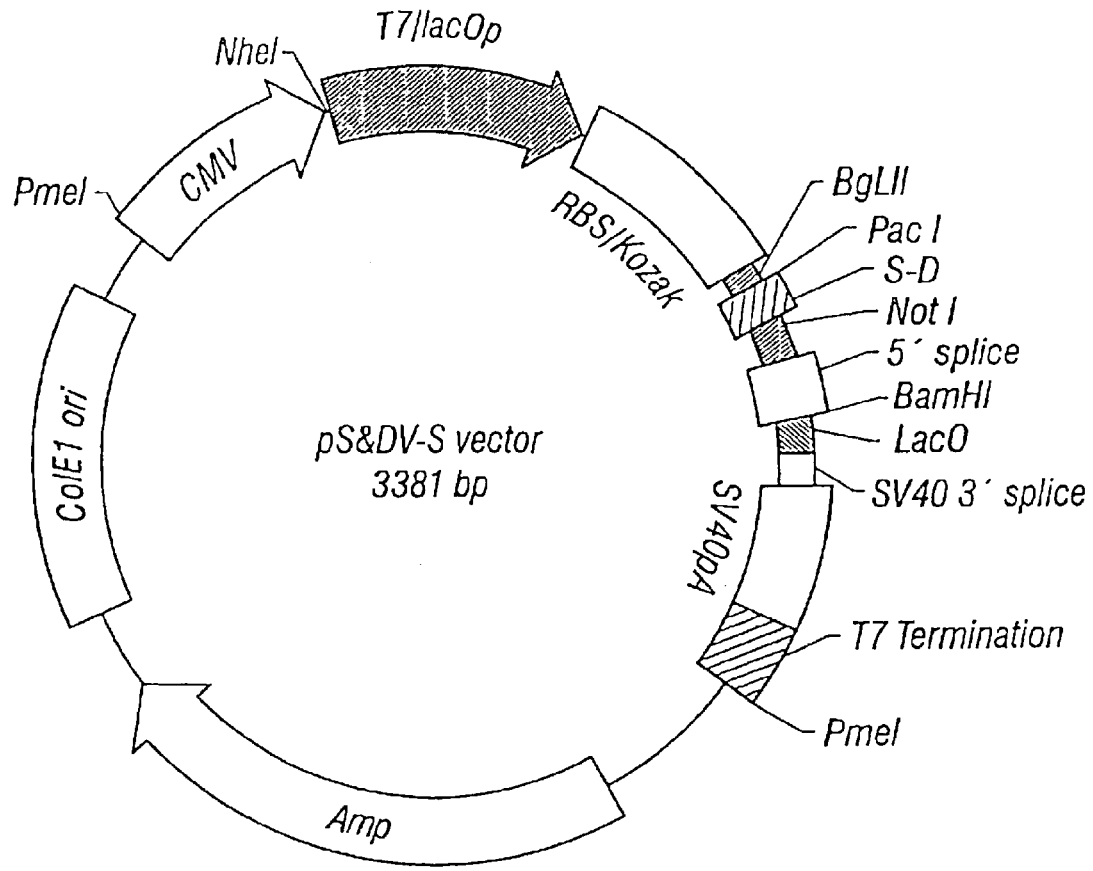
FIG. 3C depicts restriction map of pS&DV-S.
Figure 3D:
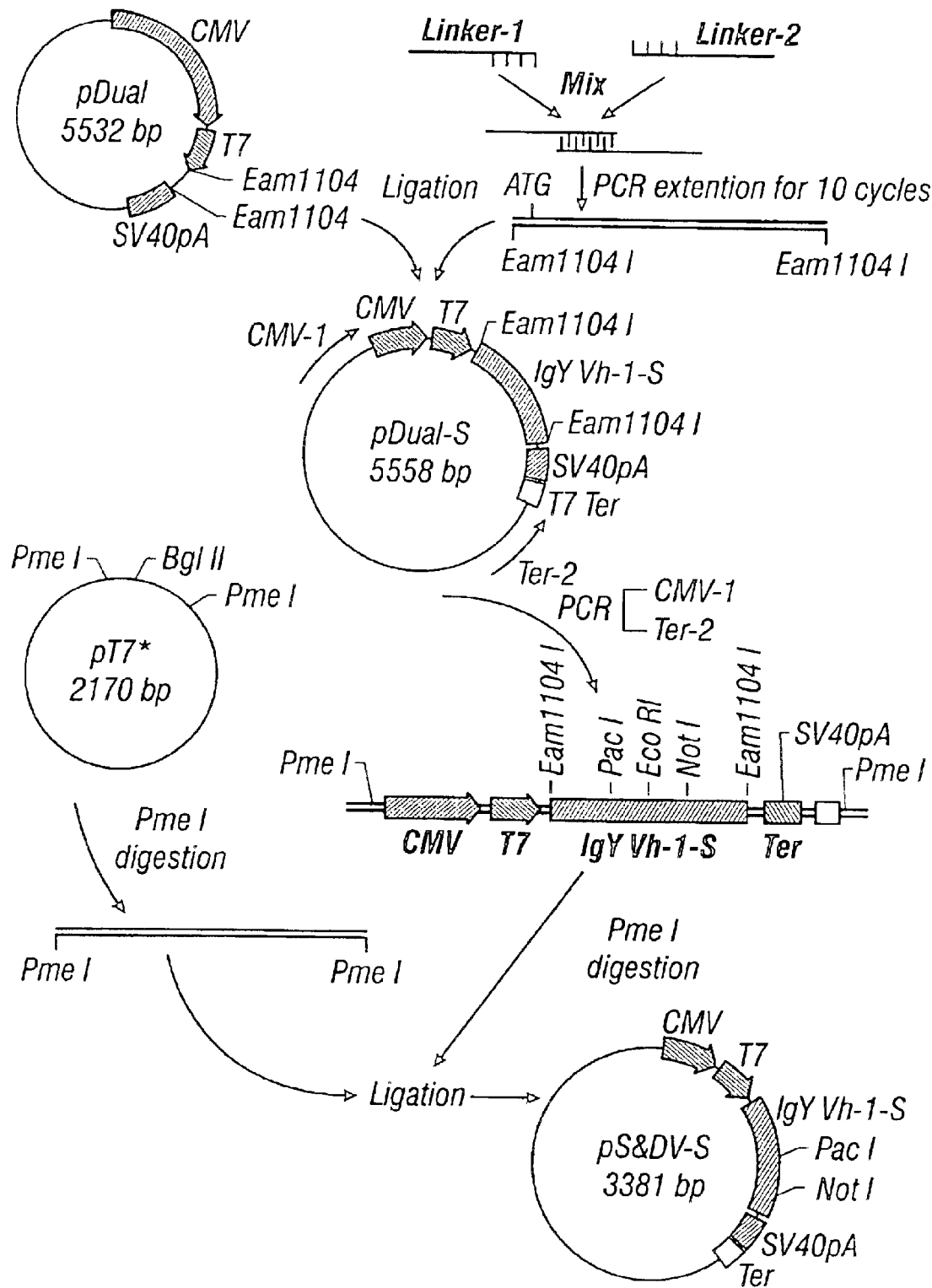
FIG. 3D depicts the construction pS&DV-S.
Figure 4:
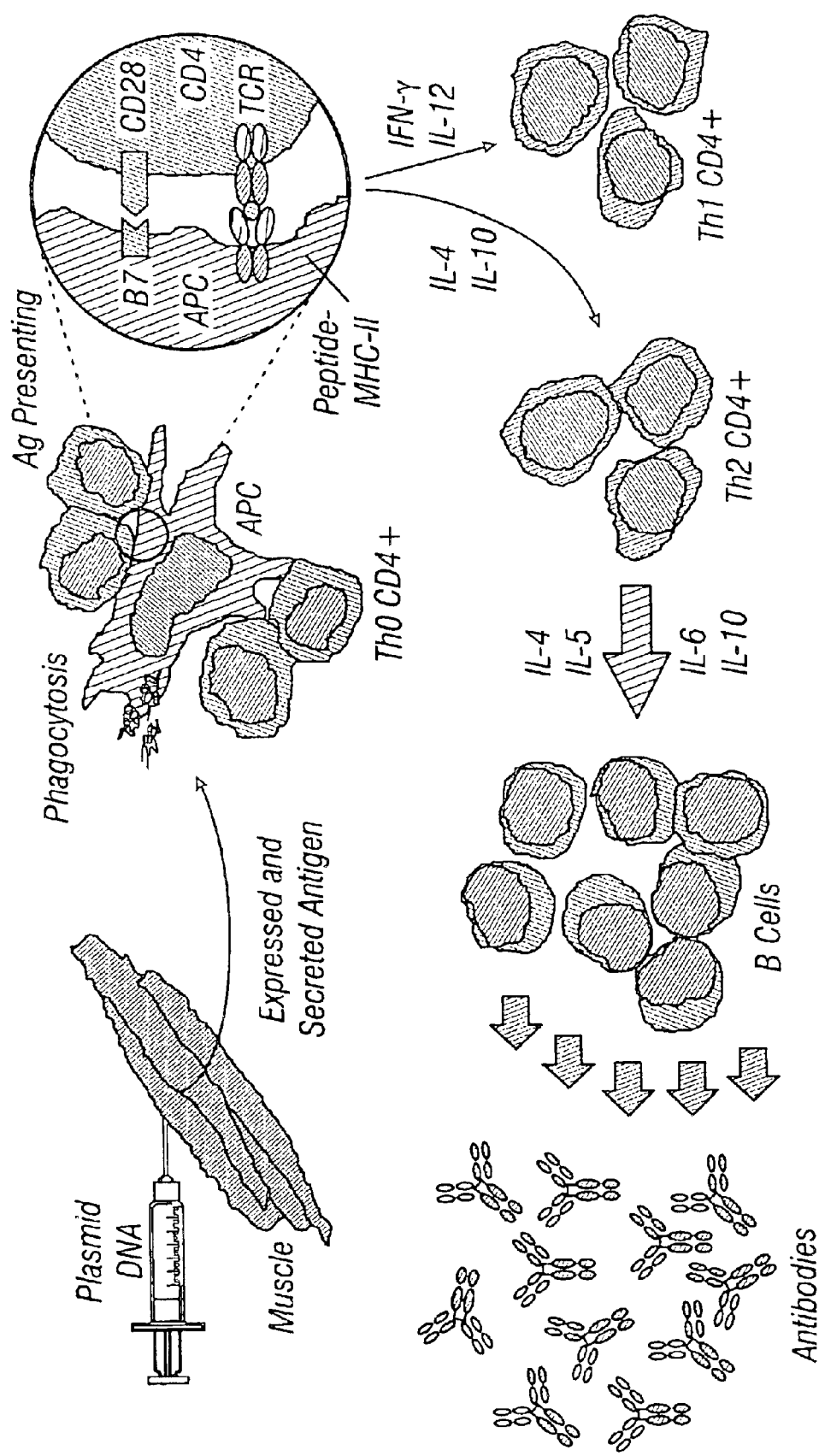
FIG. 4 illustrates potential immune response elicited by DNA vaccination.
Figure 12:
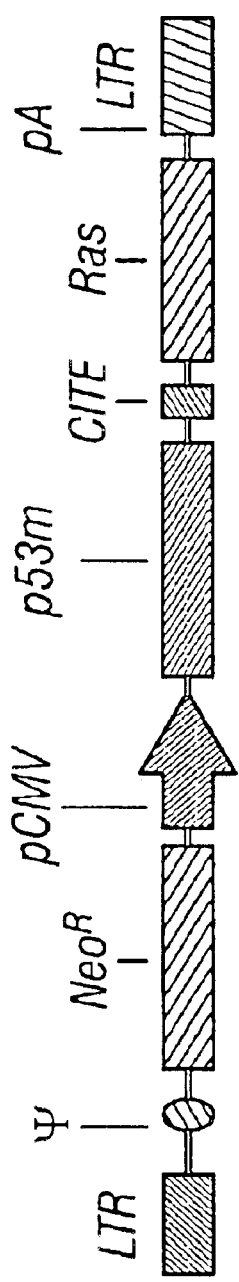
FIG. 12 depicts restriction map of pImmo vector which can be used for immortalizing chicken B cells.
Figure 13:
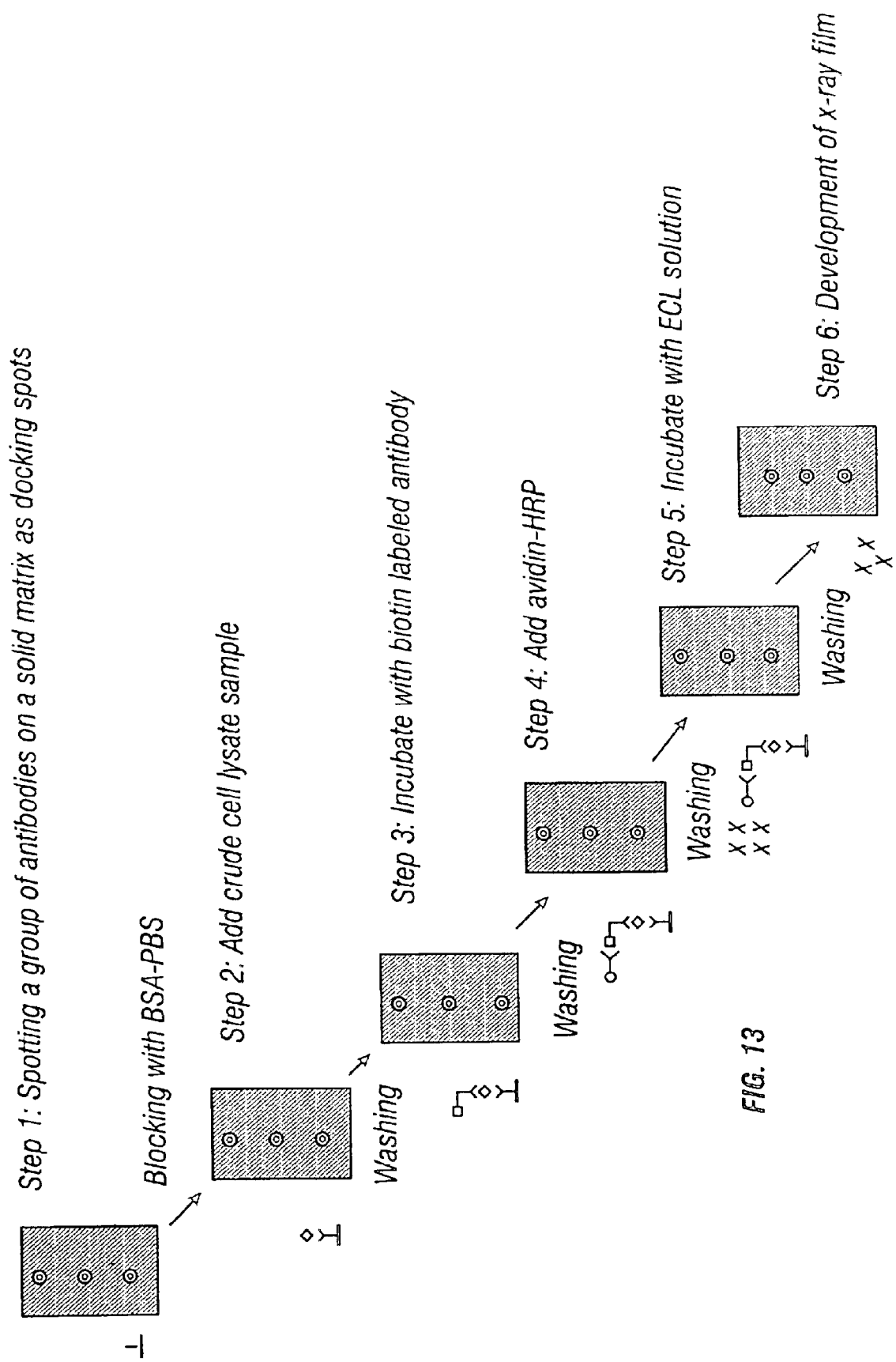
FIG. 13 illustrates a prototype of antibody-chip and its operating procedures.

In yet another specific embodiment, the present invention provides a vector for expressing genes in avian and bacterial cells, which comprises the plasmid depicted in FIGS. 3A & 3C, respectively; and a vector for immortalizing chicken antibody-producing cells, which comprises the plasmid depicted in FIG. 12.

B. Processes for Producing Monoclonal Antibodies in Chicken Using Polynucleotide Vaccination The present invention provides a process for producing a monoclonal antibody to an antigen in a chicken, which comprises: 1) delivering to said chicken a DNA sequence encoding said antigen operatively linked to a promoter, said promoter being capable of directing expression of said antigen in said avian species, or a mRNA sequence encoding said antigen, in a amount sufficient to induce detectable production of said antibodies to said antigen; 2) removing at least a portion of antibody-producing cells from said chicken; 3) immortalizing said removed antibody-producing cells; 4) propagating said immortalized antibody-producing cells; and 5) harvesting the monoclonal antibody produced by said immortalized antibody-producing cells.

Any antibody-producing cells can be removed in step 2) of the above process. In a specific embodiment, the antibody-producing cells are removed from spleen or bursa in step 2).

The chicken spleen B cells can be immortalized by any methods known in the art. In a specific embodiment, the chicken spleen B cells are immortalized by fusing with cells of a chicken B lymphoblastoid cell line. Examples of chicken B lymphoblastoid cell line include, but are not limited to, HU3R27, HU3R27N and R27H4. HU3R27, HU3R27N and R27H4 are disclosed in Nishinaka et al., *J. Immunological Methods*, 1991, 139:217–222, the content of which is incorporated herein by reference.

Methods for immortalizing chicken antibody-producing cells are well known in the art and any methods that are disclosed in *Current Protocols in Immunology*, (Ed. Coligan et al.) John Wiley & sons, Inc., 1997 can be used in the present invention. One such example is disclosed in Nishinaka et al., *Journal of immunological Methods*, 1991, 139:217–222, the content of which is incorporated by reference. According to Nishinaka, chicken B lymphoblastoid cell clones, such as HU3R27, HU3R27N and R27H4, are fused with spleen cells from immunized chickens at a certain parental cell/lymphocyte ratio, e.g., 1:5 at room temperature (RT) with polyethylene glycol 6000 and poly-L-arginine in PBS. The fused cells are gently washed, suspended in IMDM supplemented with FBS and plated in 96-well culture plates at the density of 3×10$^5$ spleen cells per well based on cell counts before fusion. After 24 h incubation at about 38° C., HAT medium is added to each well, and kept for 10–14 days in the same medium with repeated medium change at intervals of 2–3 days. After 10–14 days, culture supernatants from these wells are used for identification of antibody-secreting hybridomas.

Cloning can be performed by a soft agar culture method. Growing hybridoma cells are distributed to 60 mm plates in soft agar medium containing IMDM, Noble agar (Difco), EBS and conditioned medium from a parental cell culture (Id.). The soft agar plates are allowed to cool at room temperature and then incubated at about 38° C. in a $CO_2$ incubator. Visible colonies are individually removed from the soft agar and adapted to growth in liquid medium.

In still another specific embodiment, the chicken spleen B cells are immortalized by oncogene transformation. Preferably, the oncogene used in transformation is mutant chicken p53 oncogene or Ras oncogene. In addition, using V-rel oncogene immortalization of antibody producing avian B cell has also been shown in U.S. Pat. Nos. 5,258,299 and 5,049,502, which patents are incorporated herein by reference in its entirety.

In preferred embodiments, the DNA sequence or the mNA sequence encoding the antigen is not contained and delivered in a viral vector, such as a viral vector derived from an adenovirus. Also preferably, substantially naked DNA sequence or mRNA sequence are used as immunogens.

C. Processes for Determining the Proteomics Profile of a Set of Pre Selected DNA Sequences Isolated from a Bio-Sample In one aspect, the present invention provides a process for assessing the proteomics profile of a set of pre-selected DNA sequences isolated from a bio-sample, which process comprises: 1) cloning each of said DNA sequences into a dual-expression vector that is capable of expressing said DNA sequences in avian cells, non-avian cells or in vitro expression systems; 2) delivering said DNA sequence in said dual-expression vector formed in step 1), or mRNA or protein encoded by said DNA sequence, or a mixture thereof, to an avian species in an amount sufficient to induce detectable production of antibodies to an antigen encoded by said DNA sequence, and recovering said antibodies from said avian species; 3) delivering said DNA sequence, or mRNA encoded by said DNA sequence, or a mixture thereof, which is delivered to said avian species in step 2), to said non-avian cells, and recovering proteins or peptides encoded by said DNA sequence from said non-avian cells, or expressing and recovering proteins or peptides encoded by said DNA sequence in said in vitro expression systems; 4) conducting immunoreactions between said antibodies recovered in step 2) with said proteins or peptides recovered from step 3) to characterize the immunospecificity of said antibodies; and 5) conducting immunoreactions between said antibodies recovered in step 2) with said bio-samples to determine the proteomics profile of said set of pre-selected DNA sequences.

Preferably, the set of pre-selected DNA sequences used in the process is a cDNA library. Also preferably, the bio-sample being analyzed is of human origin. Further preferably, the dual-expression vector is the plasmid depicted in FIG. 3A or FIG. 3C is used.

Any avian species can be used in the present processes. For example, chicken, quail, turkey, duck or goose can be used. Preferably, chicken or quail is used.

Any non-avian cells can be used for producing proteins or peptides encoded the pre-selected DNA sequences. Such proteins or peptides can be used as immunogens in the avian species to generate the desired antibodies and/or used in the characterization the antibodies generated from the above described processes. Animal, plant, fungus and bacterium cells can be used, provided that the promoters and the non-avian cells used are compatible, i.e., the promoters can direct expression in the selected non-avian cells. Preferably, well-established cells, cell lines and strains are used. For example, for mammalian cells, CHO or 293 cells are preferred; for insect cells, Sf9 or High Five cells are preferred; for yeast cells, *S. cerevisiae* cells are preferred; and for bacterium cells, *E. coli* cells are preferred.

In one specific embodiment, the DNA sequence or the mRNA encoded by the DNA sequence is used as immunogens delivered to the avian species. The DNA or mRNA sequence can be delivered directly to a tissue of the avian species. Preferably, the DNA or mRNA sequence is delivered directly to muscle, skin or mucous membrane. The DNA or mRNA sequence can be delivered by injection, by gene gun technology or by lipid mediated delivery technology. Alternatively, the DNA or mRNA sequence can be delivered to a cell of the avian species and said cell containing the DNA or mRNA sequence is delivered to a suitable tissue of the avian species. For example, the DNA or mRNA sequence can be delivered to blood cells or spleen B cells. The DNA or mRNA sequence can be delivered to avian cells via $Ca_3(PO_4)_2$-DNA transfection, DEAE dextran-DNA transfection, electroporation, transfection using "LIPOFECTIN"™ reagent, gene gun technology or viral gene delivery system. In a specific embodiment, the DNA sequence or the mRNA sequence encoding the antigen is not contained and delivered in a viral vector, such has a viral vector derived from an adenovirus. For example, substantially naked DNA or mRNA sequence can be used as immunogen.

In another specific embodiment, the protein encoded by the DNA sequence is used an immunogen and delivered to the avian species to generate antibodies. Any known methods for generating antibodies using protein or peptide immunogens can be used. Preferably, fusion proteins containing the protein or peptide immunogens, such as GST, His-tag, intein and CBD based fusion proteins can be used. Fusion proteins with thermally-responsive elements can also be used.

The antibodies generated in the avian species can be recovered by any methods known in the art. For example, the antibodies are recovered from egg yolk of the avian species such as chicken or quail. Preferably, the antibodies are purified from the egg yolk by ammonium sulfate precipitation, by polyethylene glycol 6000 precipitation or by caprylic acid precipitation. The antibodies can also be recovered from the antibody-producing B cells of the avian species such as chicken.

The antibodies generated in the avian species can be characterized by the immunoreactions between the antibodies and their protein and peptide antigens. Such immunoreactions include, but are not limited to, immunoblotting, immunoprecipitation or in situ immunostaining. The immunoreactions can be conducted to determine the existence, quantity, subcellular location or tissue expression specificity of proteins or peptides encoded by the set of pre-selected DNA sequences in evaluating proteomics profile of the set of pre-selected DNA sequences in the bio-sample. The present processes can be used to assess proteomics profile of any biosamples. For example, The present processes can be used to assess proteomics profile of a physiologically normal or abnormal biosample. The biosamples can be derived from animals including humans, plants, fungi, bacteria and viruses. The biosamples can be derived from cells when such cells are in a particular stage of a biological cycle, e.g., a particular phase of cell cycle. For biosamples derived from higher organisms, the biosamples can be derived from particular tissues or organs, or from particular developmental stage, e.g., fetal cells. In a specific embodiment, the cDNA library encodes secreted proteins or peptides in the bio-sample.

The DNA sequence can further comprise a sequence that directs secretion of the encoded antigen in the avian species. One example of the secretion-directing sequence is a leader sequence. Preferably, the leader sequence used is an endogenous leader sequence of the avian species. Exemplary leader sequences include the leader sequence of chicken IgY, chicken SPARC, chicken serum albumin, or chicken tissue-type plasminogen activator (tPA) and the leader sequence of IL-1, CD4 and MHC.

A process for identifying physiologically distinguishable markers associated with a physiologically abnormal bio-sample is also provided, which process comprises: 1) assessing proteomics profile of said physiologically abnormal bio-sample through the above described process; 2) assessing proteomics profile of a comparable physiologically normal bio-sample through the above described process; and 3) comparing the proteomics profile obtained in step 1) with the proteomics profile obtained in step 2) to identify physiologically distinguishable markers associated with a physiologically abnormal bio-sample.

The present invention further encompasses multi-functional gene expression vectors (pMFGEV) that are designed for rapid cloning and/or transferring target gene fragment between different vectors for functional study or can be used in different host cells such as mammalian, bacterial and inset cells. To be used in the present methods for generating antibodies in avian species, the pMFGEV vectors must contain sequences that are capable of directing gene expression in the desired avian cells and non-avian cells or in vitro expression systems. In some cases, the pMFGEV vector can have triple promoters which can express the same target gene by transformation or transfection into mammalian, bacterial and inset cells. For example, chicken β-actin promoter can be used for avian cell expression, p10 promoter can be used for inset cell expression and T 7 promoter can be used for bacterial expression. Vectors contain such triple promoters are known in the art and are commercially available, e.g., pTriEx-1 from Novagen Inc (Madison, Wis., USA). The pMFGEV vectors can also include sequences for facilitating site-specific homologous recombination, such as baculoviral recombinant element or Ad5 ITRs, and/or sequences for facilitating viral packagings, such as retroviral LTRs. Such pMFGEV vectors can be used to facilitate homologous recombination among different vectors and to generate packaged viral particles, e.g., baculoviral or adenoviral particles, for high-efficiency gene transferring.

FIG. 16 illustrates an exemplary pMFGEV vector that can be used in the processes or methods described herein. The exemplary pMFGEV vector carries its own ColE ori fragment for replication in bacterial cells and EBV OirP DNA fragment for maintaining episomal DNA replication after the vector is transfected into mammalian cells. One unique feature of this vector is that it carries the Site-Specific Recombinant Element (SSRE) just downstream of promoter region. The inclusion of SSRE can dramatically simplify gene cloning procedure for inserting a target gene into this vector. Any known SSRE element can be used including the SSRE fragment derived from well characterized systems such as Int or FLP site-specific recombination pathways (See Landy, *Current Opinion in Genetics & Development,* 3:699–707 (1993)). WO 99/21977 discloses vectors containing SSRE element, which can transfer a target gene in the defined orientation using modified lambda Int site-specific DNA recombinant mechanism. When cDNA library is constructed by flanking the modified lambda Int site-specific fragment and DNA sequenced, selected target DNA fragment can be transferred directly from cDNA library vector into pMFGEV vector by mixing the two vectors with suitable reconmbinases such as Gateway BP clonase Mix or Gateway LR clonase mix Cat # 11789-013 or 11791-019 and the enzymes made by Life Technologies Inc. MD. USA.

A vector for immortalizing chicken antibody-producing cells is further provided, which vector comprises the plasmid depicted in FIG. 12.

In a specific embodiment, the present invention provides a method for selecting and constructing a set of DNA sequences to generate antibodies against proteins or peptides encoded by such DNA sequences, which method comprises: (1) selecting specific tissue sample of interest; (2) extracting mRNA from the selected sample; (3) performing cDNA synthesis, preferably using modified RNA normalization procedure; (4) fractionating the synthesized cDNA, preferably by gel electrophoresis; (5) constructing a cDNA library in the vector that can express the cDNA in both avian cells and bacterial cells, such as the pS&DV depicted in FIG. 3A and the pS&DV-S depicted in FIG. 3C; (6) establishing the fractionated master cDNA library; (7) conducting quality assurance analysis of the master cDNA library; (8) purifying the cloned cDNA; (9) determining the sequence of the cloned cDNA; and (10) conducting bioimformatic analysis of the DNA sequence data to select the set of the DNA sequences for further DNA vaccination. Other criteria and procedures for selecting and constructing an interested set DNA sequences are known in the art and such other procedures are also encompassed in the present invention.

The tissue sample can be obtained from either fresh or frozen sources. The tissue sample can be obtained from human, animal, plant or microbe. Selection of specific tissue will be determined in each specific study. For example, if one desires to obtain human liver specific gene, one could use human adult liver or fetal liver tissue as the resource for mRNA extraction. In a preferred embodiment, the tissue is used as fresh as possible.

The technology for preparation of mRNA is well known in the art. For example, the procedures described in Ausubel et al., *Current Protocols In Molecular Biology*, New York, John Wiley and Sons, 1995; Dracopoli et al., *Current Protocols in Human Genetics*, New York: John Wiley and Sons, 1995; and Sambrook et al., *Molecular Cloning,* 2nd Edition, Plainview, N.Y. Cold Spring Harbor Press, 1989 can be used. Alternatively, commercially available mRNA extraction kits, such as the kit from Life Science BRL (Gaithersburg, Md.) and Promega Inc. (Madison, Wis.), can be used. In a preferred procedure for extracting specific message RNA, the tissue sample can be rapidly frozen in liquid nitrogen, grounded and resuspended in RNA extraction buffers such as 4M guanidine solution. Alternatively, mRNA can be extracted directly from the tissue using lysis buffer, and the extracted mRNA can be further purified on an ion exchange column, such a the column from Qiagen (Chatsworth, Calif.).

The following illustrates procedures for obtaining a cDNA library, which contains low level housekeeping genes, using a modified RNA normalization procedure. Large-scale single-pass sequencing of cDNA clones randomly picked from libraries has proven to be a powerful approach to discover genes (Adams et al., *Science*, 1991, 252:1651–1656; Okubo et al., *Nature Genet.*, 1992, 2:173–179). However, ordinary cDNA libraries may contain a high frequency of undesirable "junky" clones that may not only drastically impair the overall efficiency of the approach, but also seriously compromise the integrity of the data that are generated. Among such junky clones are (a) clones that consist exclusively of poly(A) tails; (b) clones that contain very short cDNA inserts; (c) clones that contain nothing but the 3' half of the NotI-oligo(dT)18 primer used for synthesis of first strand cDNA ligated to the adopter; and (d) chimerical clones. To overcome this problem, the classical procedure for normalization and subtraction of RNA for cDNA synthesis can be used (Bonaldo et al., *Genome Research*, 1996, 6:791–806; Neto et al., *Gene*, 1997, 186:135–142). The disadvantage for this procedure is the multiple steps in the manipulation of mRNA resulting in generating the short RNA in the final cDNA products. However, there are alternative procedures that can be utilized. Because a large fraction of all human gene has been identified already, redundant genes which have been characterized from different tissue now can be avoided simply by using biotin-labeled specific redundant gene oligo mixed with oligo dT primer for cDNA synthesis. After finishing the reverse-transcription reaction, the redundant gene cDNA can be removed from the cDNA mixture using avidin-magnetic beads. This procedure can generate cDNA with very low background of housekeeping gene cDNA (Diatchenko et al., *Proc. Natl. Acad. Sci.*, 1996, 93:6025–6030). Another procedure can also be used to enhance the reverse-transcription reaction of mRNA into cDNA (Gastel & Sutter, *BioTechniques*, 1996, 20:870–875).

The following illustrates procedures for fractionating cDNA by gel electrophoresis. The burden of large-scale DNA sequencing is the repeated sequencing of the same clones multiple times. Using non-amplified cDNA library can help to improve the DNA sequence and checking first-strand cDNA synthesis efficiency, which can also be the index for determining the quality of reverse-transcription reaction (Bodescot & Brison, *BioTechniques*, 1997, 22(6):1119–1125). In a preferred procedure, the total cDNA products can be fractionated by gel electrophoresis, such as 0.8% to 1% agarose gel. Then the desired size of cDNAs can be pooled and extracted before ligating into the cloning vectors, such as the vectors from Qiagen (Chatsworth, Calif.). The collected length of cDNAs can vary such as every 0.5 kb as the region for the one pooled sample. Those pooled cDNAs can then be inserted into vector in the different ligation tubes designated for different transformation experiments. In the mixed cDNA library, the full-length cDNA often resides in a complex background of small cDNA mixture. This fractionation procedure for cDNA preparation can generate a sub-population of cDNA library. The designated length of cDNA clones will also help to identify the full-length clone from the subpopulation of cDNA once the 3'EST sequence are known and the size of gene transcript is obtained from the standard RNA Northern Blot experiments (Chenchik et al., *Bio/Techniques*, 1996, 21:526–534). This procedure is applicable to the construction a variety of cDNA libraries from different tissue samples.

The following illustrates procedures for constructing cDNA library using a dual-expression vector, such as the pS&DV and pS&DV-S depicted in FIGS. 3A and 3C, respectively. The purpose for directly cloning cDNA insert into a dual expression vector is to enable conducting DNA vaccination in an avian species and to expressing encoded protein or peptide antigen in bacteria with the same DNA. This dual functional vector carries those fragments for avian cell gene expression such as endogenous avian promoters, or viral promoters such CMV promoter, SV40 intron and SV40 polyadenylation site. The vector also carries T7 RNA polymerase promoter expression system in which the cloned gene will express in *E. coli* strain that carries T7 RNA polymerase such as BL21 (DE3) (Studier et al., *Methods in Enzymol.*, 1990, 185:60–89). Due to the codon preference between human and *E. coli*, some human cDNAs or genes may be expressed at low level in commonly used *E. coli* host cells. By adding three new modified human gene codons commonly used in tRNA gene into *E. coli* strain, this newly developed *E. coli* strain (BL21 CodonPlus-RIL), which is suitable for the human cDNA or gene expression, is commercially available, e.g., from Strategene Inc (Cat #: 230245). The cDNA fragments can be directionally inserted into the vector by digesting the cDNA at both ends with different restriction enzymes, such as PacI for 5' and NotI for 3' end. Cloning the cDNA with correct orientation will ensure the expression of the gene. Considering that most of cDNA fragments may lack 5' region or translation initiation code (ATG) in its fragment, the artificial ATG has been created in the vector to enhance the protein expression level in the bacterial by adjusting the distance of Shine-Dalgarno/Kozak consensus sequence between the ATG. There are multiple cloning sites located just downstream of ATG. And three sets of different open read frames (ORF) have been constructed in the vector. In case the cDNA in the vector is not in the desired or correct ORF, it can be easily transferred into the right ORF vector using the restriction enzyme digestion. In addition to all the elements in pS&DV, pS&DV-S contains a chicken IgY leader sequence, which can direct secretion of the proteins or peptides encoded by the cDNA inserts in chicken cells.

The following illustrates procedures for constructing a master cDNA library consisting of subpopulation of fractionated cDNA clones. The vector and cDNA ligation mixture can be efficiently transformed into bacterial cells such as HB101 cells using standard procedure, preferably by electroporation, which are available from different commercial vendors, such as Life Science BRL (Gaithersburg, Md.). After plating the transformed bacterial cells on the culture plate and incubating the cells overnight, the clones can be picked up and then transferred into 320 well plate which contains frozen reserve solution such as 15% glycerol (Ausubel et al., *Current Protocols In Molecular Biology*, New York, John Wiley and Sons, 1995, and Sambrook et al., *Molecular Cloning*, 2nd Edition, Plainview, N.Y. Cold Spring Harbor Press). As each fractionated cDNA preparation is pooled as sub-population library, the separated clones for total library should preferably be at least 10 times more than potential human gene numbers. Preliminary data from published data base indicate that there may be approximately 100,000 functional genes in human genome. So for each tissue-specific cDNA library, about 1 million clones have to be picked up for further DNA sequencing analysis. The automatic clone pick-up systems are available from different commercial vendors such as Stanford University, DNA sequence Center, CA.

The following illustrates procedures for conducting quality assurance analysis of the master cDNA library. Such quality assurance analysis before large-scale DNA sequencing will ensure the desired outcome in a cost efficient fashion. There are several ways in which a portion of cDNA library can be analyzed and then the data be used for determining the quality of the total cDNA library. According to one procedure, about 1,000 clones can be randomly picked up from the library, DNA sequencing can be performed using a specific primer for cDNA 5' sequence. Analyses of such limited sequencing data will give useful information such as the gene distribution pattern, the length of inserted gene and percentage of vector self-ligation. Alternatively, about 2,000 clones can be cultured on a plate(s) and be replicaed to nitrocellulose membrane and be screened by DNA hybridization using housekeeping gene sequence as the probe. For example, if the cDNA library is derived from liver tissue, β-actin and/or albumin nucleotide sequences can be used as the probe. The probes can be labeled by any techniques known in the art. In a preferred procedure, the probe is labeled using the random primer method (Feinberg & Vogelstein, *Analyt. Biochem.*, 1983, 132:6–13; Dracopoli et al., *Current Protocols in Human Genetics*, New York, John Wiley and Sons, 1995). Preferably, $^{32}$P-dNTP is incorporated into a random primer labeling reaction using a kit such as the DECprime II DNA labeling kit (Ambion, Austin, Tex.). Other isotopes such as $^{35}$S or $^{33}$P can also be used for labeling reaction. Alternatively, nonisotopic labeling agents can be used (Kricka, ed., *Nonisotopic Probing, Blotting, and Sequencing*, 2nd Ed. San Diego, Calif., Academic Press, 1995). The hybridization results can be used to review the background contamination of housekeeping genes in the normalized cDNA library. Since most of the housekeeping genes occur at about the same rate in cDNA library generally, the hybridization rate for housekeeping genes can be used to determine the quality of the cDNA library. The quality of the cDNA library can also be determined by PCR-based procedures. (Pacchioni et al., *BioTechniques*, 1996, 21:644–649). In a preferred procedure, PCR amplifications are carried using the housekeeping genes, such as β-actin gene, as the 3' DNA specific oligo and the T7 promoter oligo as the 5' primer in the randomly picked cDNA library clones. Subsequent detection for presence or absence of PCR products (+/−scores) is carried out either by gel electrophoresis or by internal oligonucleotide hybridization. The PCR amplification results will not only reveal the percentage of the housekeeping gene's presence in the cDNA library, but can also be used to determine the average length of the cDNA insert. The PCR amplification reaction of the random clones of the cDNA library can be conducted using commercially available reagents or kits, such as the ones produced by Origene Technologies, Inc. (Rockville. Md.).

The cloned plasmid DNA can be purified by any methods known in the art. Preferably, the automatic plasmid purification equipment such as the Quiagen Inc automation system 9600 (Valencia, Calif.) can be used to provide highly purified DNA template for subsequent DNA sequencing analysis. Alternatively, cDNA Clones can be used for PCR amplification and nest-PCR again to provide DNA sequencing template. Since the sequence is known, the two pare of primers for PCR can be easily standardized for all of the clones in the library.

DNA sequences can be determined by any methods known in the art. Preferably, each randomly selected clone is purified from a cDNA library, a DNA sequencing template is prepared. This template is sequenced by the dideoxy method, preferably using an automated DNA sequencer, such as an A. L. F. (Pharmacia Biotech, Piscataway, N.J.) or an ABI/373 or ABI/377 (Applied Biosystems, Foster City, Calif.). In addition to this "shotgun" phase, in which an initial reading is taken from each clone using a universal primer, a "walking" phase takes additional reading from selected clones by use of custom primers. Complete protocols for these and related sequencing methods are described in Ausubel et al., *Current Protocols In Molecular Biology*, New York, John Wiley and Sons, 1995; and in Sambrook et al., *Molecular Cloning*, 2nd Edition, Plainview, N.Y. Cold Spring Harbor Press. An efficient design produces small (preferably 18 bp–22 bp) oligonucleotides which can be used as "walking" primer for DNA sequence. The oligonucleotide sequences are generally designed to preferentially detect sequences that are related to the ends of genes in the previous DNA sequence database. This selective bias can be achieved either by manually reading of sequence or by examination of the sequences to be compared. Once designed, these oligonucleotides can be ordered from a DNA synthesis service such as the Research Genetics, (Huntsville, Ala.). Alternatively, the oligonucleotides can be synthesized on a DNA synthesizer, e.g., on the Applied Biosystems (Foster City, Calif.).

The DNA sequencing reaction products can be separated by electrophoresis, preferably on polyacrylamide gels using fluorescence detection. Other DNA size separation technologies, such as ultrathin gel slabs (Kostichka et al., *Bio/Technology*, 1992, 10:78–81), capillary arrays (Mathies & Huang, *Nature*, 1992, 359:167–169), and mass spectrometry (Wu et al., *Rapid Commun. Mass Spectrom.*, 1993, 7:142–146), can also be used. DNA sequencing analysis without using gel electrophoresis has also been done by hybridization methodologies (Drmanac et al., *Science*, 1993, 260:1649–1652; Southern et al., *Genomics*, 1991, 13:1008–10017). Another approach is the base addition sequencing strategy (BASS), which uses synchronized DNA polymer construction to determine the sequence of unknown DNA templates (U.S. Pat. No. 5,302,509; WO 93/21340; and WO 91/06678).

The sequences of the selected clones by "walking" procedure can be assembled into the complete cDNA sequence of the inserted DNA by matching overlaps. Computer programs are available for these tasks (e.g., Rodger Staden programs, Cambridge, UK; DNAStar, Madison, Wis.). Following sequence assembly, similarity and homology searches can be conducted in relevant sequence databases (e.g., GenBank, Bethesda, Md.; EMBL, Cambridge, UK; Phil Green's GENEFINDER, Seattle, Wash.) to identify genes and repetitive elements, to infer function, and to determine the sequence's relation to other parts of the genome and cell (Gonzalez & Sylvester, *Genome Research*, 1997, 7:65–70).

The above described procedures have been successfully applied to sequencing the genomes of several bacteria (Human Genome Sciences, Gaithersburg, Md.) such as *E. coli* (Plunkerr et al., *Nucl. Acids Res.*, 1993, 21:3391–3398), and higher organisms, such as yeast (Oliver et al., *Nature*, 1992, 357:38–46), human (Martin-Gallardo et al., *Nature Genet.*, 1992, 1:34–39), mouse (Wilson et al., *Genomics*, 1992, 13:1198–1208.) and *C. elegans* (Wilson et al., *Nature*, 1994, 368:32–38; Sulston et al., *Nature*, 1992, 356:37–41). The automated sequencing of even large genome regions from mapped cosmid (or other) clones is now routine in several centers (Sanger Center, Cambridge, UK; Washington University, St. Louis, Mo.), with very low error at an average cost of $0.38–0.50 or less per base. Specific strategies and protocols for these efforts have been described in Griffin and Griffin, ed. DNA sequencing: *Laboratory Protocols*., New Jersey, 1992).

The following illustrates procedures for computer-based bioimformatic analyses of the cDNA sequence data. In a preferred procedure, the sequences of the selected clones by universal primer from 5' of inserted DNA can be firstly analyzed using specific computer program. For example, similarity and homology searches can be conducted (GenBank, Bethesda, Md.; EMBL, Cambridge, UK; Phil Green's GENEFINDER, Seattle, Wash.) to identify functionally known genes and un-identified cDNA fragments. The junction DNA sequence between the vector and inserted DNA and potential ORFs can be analyzed, which will help to infer gene function and to determine the sequence's relation to other parts of the genome and cell (Altchul et al., *Nature Genetics,* 1994, 6:119–129). For some newly identified sequences, after "walking" procedure, those new sequences can be assembled into a complete cDNA sequence of the inserted DNA by matching overlaps. Computer programs are available for these tasks (e.g., Rodger Staden programs, Cambridge, UK; DNAStar, Madison, Wis.). Following sequence assembly, the full-length cDNA coded putative protein can be further analyzed such as for functional domain searching. The analysis data can be categorized into computer database. Other experiments, such as looking for the DNA transcription control elements after function of the cDNA is mapped, can also be conducted (Fickett & Hatzigeorgious, *Genome Research,* 1997, 7:861–878).

Once the DNA sequences are selected, the processes described in §§ A and B. can be used to generate desired antibodies, whether polyclonal or monoclonal ones, against the proteins or peptides encoded by such selected DNA sequences.

In a specific embodiment, the DNA sequences used in the DNA vaccination are also delivered into competent bacteria cells to produce the encoded proteins or peptides, which can be used in characterizing the antibodies generated by the DNA vaccination. Preferably, the bacteria cells are competent *E. coli* cells. Also, preferably, the dual-expression vector depicted in FIG. 3A or 3C is used in delivering the DNA sequence into bacteria cells. When the DNA sequences contained in the vector depicted in FIG. 3A or 3C are transformed into bacterial cells, such as BL21(DE3) cells, which carry the RNA 7 polymerase, the proteins encoded by the delivered DNA sequences can be expressed at high level in the presence of an inducer, e.g., IPTG. DNA sequences can be delivered into bacterial cells by any methods known in the art (e.g., Ausubel et al., *Current Protocols In Molecular Biology*, New York, John Wiley and Sons, 1995; and in Sambrook et al., *Molecular Cloning,* 2nd Edition, Plainview, N.Y. Cold Spring Harbor Press). Preferably, commercially available systems for DNA transformation, such as the one from Life Science BRL (Geitesburg. Md.), can be used.

Bacterially expressed proteins or peptides can be recovered by any methods known in the art (e.g., Ausubel et al., *Current Protocols In Molecular Biology*, New York, John Wiley and Sons, 1995; and in Sambrook et al., *Molecular Cloning,* 2nd Edition, Plainview, N.Y. Cold Spring Harbor Press). For example, transformed bacterial clones can be picked up and grown in LB culture medium. Before harvesting the bacterial cells, an inducer such as IPTG can be added to induce the protein expression. Bacterial cells can be harvested by centrifugation, resuspended directly in SDS-PAGE lysis buffer and analyzed by SDS-PAGE using commercially available system, such as the one from Bio-RAD Inc. (Hercules, Calif.).

The immunoreactions between the antibodies generated by the DNA vaccination and the bacterially expressed proteins or peptides can be analyzed by any methods known in the art (e.g., Ausubel et al., *Current Protocols In Molecular Biology*, New York, John Wiley and Sons, 1995; and in Sambrook et al., *Molecular Cloning,* 2nd Edition, Plainview, N.Y. Cold Spring Harbor Press). Preferably, such immunoreactions are analyzed by immunoblotting. For example, after the SDS-PAGE separation, the proteins and peptides to be analyzed can be transferred onto a suitable membrane, e.g., PVDF membrane, according to the procedures described in Schielen et al., *Journal of Immunological Methods,* 1995, 188:33–41. The immunoblotting reaction can be analyzed by any methods known in the art. Preferably, the immunoblotting reactions are detected by commercially available system, such as the Chemiluminescence detecting system from BIO-RAD (Hercule, Calif.).

The positive results generated from immunoreaction between the antibodies and the bacterially expressed proteins or peptides only confirm that proteins or peptides are encoded by the DNA sequences isolated from bio-samples. After the antibodies are characterized by the immunoreactions between and the bacterially expressed proteins or peptides as described above, further immunoreactions between the antibodies and the bio-sample, from which the DNA sequences are isolated, can be conducted to determine the proteomics profile of the selected DNA sequences.

If there is uncertain about the reading frame, and no unique ORF could be determined for lack of sequence homology or similarity with known sequences, the DNA fragment can be inserted into three ORFs and Western Blot assay using three different antibodies can be performed.

Any known methods can be used to analyze the immunoreactions between the antibodies and the bio-sample. Preferably, immunoblotting, immunoprecipitation and in situ immunostaining are used. In addition, the antibody-based methods can be used in conjunction with other techniques, such as two-dimensional electrophoresis (2-DE), ultra-sensitive mass spectrometry (MS), and other high-throughout functional screening assays (Persidis, *Nature Biotechnology,* 1998, 16:393–394), in the proteomics studies. The examples of such 2-DE and MS analyses include, but are not limited to, isoelectric focusing followed by mass-based separation (ISO-DALT), non-equilibrium based electrophoresis (NEPHGE), and immobilized first-dimension pH gradients (IPG-DALT) (Humphery-Smith. et al. Electrophoresis, 1997 18:1217□1242).

One technology for analyzing the immunoreactions between the antibodies and the bio-sample is tissue immunostaining, which technology is well known in the art (Feitelson & Zern, *Clinics In Laboratory Medicine*, W. B. Saunders Corn., 1996). Preferably, cryosected tissue samples are used to perform the immunostaining assay because the tissue sample fixed with this method can preserve the cellular antigen structure. The data from this assay may well represent the cellular protein expression pattern in the tested tissue. Alternative, paraffin fixed tissue sample can be used for antibody immunostaining because this type of tissue fixation preserves the tissue for long time and also can be easily collected from different medical research resources. There are several techniques which can be used to improve the immunostaining sensitivity when using paraffin fixed tissue samples (Lantis et al., *Surgical Endoscopy.,* 1998, 12(2):170–176).

The antibodies generated by the present invention and the information obtained from analyzing the immunoreactions between such antibodies and the bio-sample can used in number of ways. One such use is the generation of an antibody index and the incorporation of such antibody index into the known nucleotide sequence databases.

Recent advance in large-scale genomic sequencing requires more powerful tools for analyzing and interpreting the available DNA sequences. Homology or similarity search programs such as BLAST are very effective and reliable computational tools. New powerBLAST has been developed to enhance the function for this type of computer analysis program (Zhang & Madden, *Genome Research*, 1997, 7:649–656). In this new powerBLAST program, the search results can be exported to the interactive browser Chromoscope, or formatted as ASCII files, or as HTML pages with links to GenBank, MEDLINE, and other components of Entrez for browsing via the World Wide Web. Both the text and graphical views display the result as multiple alignments of cDNA sequences. Annotated features on the matching sequence are superimposed on the alignment, and this greatly facilitates identification of functional domains in the analyzed sequence. The antibody index generated by the present invention can be automatically linked to each of corresponding cDNA sequence, the Western blot data and tissue immunostaining data can be cross-referenced in the database. The subcellular image generated by the immunostaining with the cDNA derived antibody can be stored, and western blot analysis data can be traced in the database for estimating the size of specific cDNA encoded-protein.

The antibodies generated by the present invention can also be used in the functional analysis of the proteins or peptides encoded by new cDNA sequences. The information generated from cDNA derived antibodies can be categorized into group of functional index (Poustka et al., *Cold Spring Harbor Symp. Quant. Biol.*, 1986, 51:131–139). Through the antibody-based analysis, several types of information can be obtained for a target gene. First, whether the cloned cDNA fragment actually encodes the protein. Secondly, through the tissue immunostaining procedure, one can learn what is correct ORF for this gene. Third, where the gene encoded protein is expressed, tissue distribution pattern and subcellular localization can be determined. The expression level of a specific gene can be determined using very-well documented protein such GAPDH or β-actin as internal control. Based on those leading information for a specific gene, one can design multiple-gene functional assays to further elucidate the cellular function of the gene and understand the relationship of the gene with a specific disease, if the gene is linked to a disease or a disorder.

The DNA sequence provides information about the long-term inherited DNA stored in the nucleus and about the physical linkage of the genes in a genomic context. However, it is also useful to know how these genes are expressed and their cellular localization. Toward this end, as described above, cDNA libraries have been constructed to assess gene expression in particular tissues, and methods such as direct selection have been developed to map these cDNAs relative to a genome (Lovett et al., *Proc. Natl. Acad. Sci.*, 1991, 88:9628–9632). Other methods such as exon trapping are similarly used to measure gene expression and map exons (Buckler et al., *Proc. Natl. Acad. Sci.*, 1991, 88:4005–4009). For functional analysis of a gene, many very well developed techniques and system can be used (Christoffersen, *Nature Biotechnology*, 1997, 15:484–484; Nemotoy, *Japanese Journal of Clinical Medicine*, 1998, 56(1):224–232; Bussey, *Yeast*, 1997, 13(16): 1501–1503). The present invention can be used to study the proteomics of such selected DNA sequences.

Mutagenesis is a powerful tool to study a gene's function. The selected gene can be mutated and cloned into the specific vector for generating transgenic animal, such mice, and the phenotype of the transgenic animal can be used in elucidating the target gene's function in vivo (Stewart, *Molecular Medicine Today*, 1997, 3(3):93; Hickset al., *Nature Genetics*, 1997, 164:338–344). Alternatively, the activity of the specific cDNA encoded protein can be inhibited by a variety of technologies, such as modified oligo antisense inhibition (Milner & Southen, *Nature Biotechnology*, 1997, 15:537–541), target sequence-specific ribozyme inhibition (Duan et al., *Gene Therapy*, 1997, 4:533–543) or single chain antibody (sFv) based intracellular immunization approach (Duan et al., *Proc. Natl. Acad. Sci.*, 1994, 91:5075–5079). The present invention can be used to study the proteomics of the selected cDNA sequences of such knock-out organisms.

In a specific embodiment, the present invention provides a process for determining the proteomics profile of a set of pre-selected DNA sequences isolated from a physiologically normal bio-sample. In another specific embodiment, the present invention provides a process for determining the proteomics profile of a set of pre-selected DNA sequences isolated from a physiologically abnormal bio-sample. The abnormality of such bio-sample can be permanent or temporary, and can be caused by genetic changes or otherwise. Preferably, the physiologically abnormal bio-sample is obtained from a subject who/that has or is known in the high risk of having any diseases or disorders.

D. Immunization of Avian Species

Delivery of Nucleic Acid Immunogen by Viral Gene Delivery Systems

For generating antibodies using the processes described in the above Section C, the DNA sequence or the mRNA encoded by the DNA sequence can be used as immunogens and delivered to the avian species. Any known methods for generating antibodies using nucleic acid immunogens can be used. For example, the processes described in the above Sections A and B can be used. Alternatively, the nucleic acid immunogen can be delivered to avian species by recombinant viral gene delivery systems.

Retroviruses, owe to their high infectivity, special structure and the capacity to be integrated readily in the form of a provirus in the genome of the host cells, have been widely used for gene delivery. Since cDNA fragment or target gene can be easily constructed into retroviral based vector for gene delivery, the avian cell infectable retroviral systems such as avian crythroblastosis retrovirus (AEV) and Spleen Necrosis Virus (SNV) can be used in the present processes for to deliver nucleic acid immunogens to the avian species.

The genome of a retrovirus in its replication-defective form is composed of an RNA molecule possessing, in the direction of the transcription (5' to 3') an identical short sequence at each end, known as R. This is followed, in order, by a single sequence known as U5, a tRNA binding site (TBS), and a non-coding sequence ("leader" sequence). The RNA molecule continues with a region coding for three genes, the translation products of which are essential for the replication of the virus, and which are gag (virion structural proteins), pol (reverse polymerase) and env (envelope). The genome terminates, in order, with a non-coding sequence, a purine-rich sequence (PU), a single sequence known as U3, and finally the R sequence. The repeat end sequences (R) or single sequences (U5 and U3) peculiar to retroviruses appear to be rather well conserved in this group of viruses and contain the signals involved in the control of the expression of the viral genome.

When some of the viral gene necessary for its replication is replaced by an inserted nucleic acid fragment, these viruses are rendered replication-defective. To replicate, these viruses require the presence of, in the same host cell, a functional helper virus. Helper viruses are capable of helping replication of the replication-defective viruses with foreign nucleic acid fragment, but cannot self-replicate because the helper viruses contain only the functional gag, pol and env genes without necessary cis-acting signals for its own replication.

The cycle of infection by a retrovirus begins with the adsorption of the virions on the surface of the host cells, followed by penetration into the cytoplasm. In the cytoplasm of the host cells, the single-stranded viral RNA (a) is transcribed by the reverse polymerase present in the virion, to a linear copy of double-stranded DNA (b). The DNA copy resulting from this reverse transcription is slightly longer than the viral RNA molecule which acts as a template for it. This difference is the result of the addition of an U3 sequence at the 5' end and an U5 sequence at the 3' end.

The combination, in order, of the U3-R-U5 sequences constitutes a repeat sequence at both ends of the DNA molecule, known as LTR (Long Terminal Repeat). The copies of viral DNA containing one or two LTR sequences are conveyed to the nucleus where they are converted to molecules of circular shape. Some circular molecules only retain a single LTR. These molecules are then integrated in the host cell genome. The viral DNA is integrated in the host cellular DNA in such a manner that it is enclosed by an LTR at each end, and then bears the name of proviral DNA or provirus. We shall henceforward designate as "left LTR" of a provirus the LTR situated upstream of the gag gene, and as "right LTR" the LTR situated downstream of the env gene.

The provirus acts as template for the transcription of viral RNA molecules. The transcription is initiated at the R sequence of the left LTR and stops beyond the polyadenylation signal carried by the U3 or R sequence of the right LTR. The RNA molecules obtained after transcription of the provirus are a reflection of the mRNA of the eucaryotic cells, "capped" by a terminal 7 mG residue at the 5' end and provided with a polyadenylated sequence at their terminal 3' end.

Delivery via AEV Vector

The use of AEV retrovirus as a vector for delivery of a foreign gene (hereinafter vector AEV) can use different forms as a result of wide selectable vector available now. The description below refers more especially to AEV virus for its gene delivery into avian cell such as chicken, but the method generally relates to other retroviruses such as SNV which will described in the following section. When the vector AEV is employed under conditions which enable its replication and the formation of virions to take place, that is to say with a helper virus, the infection of cell culture in vitro or directly viral particle injection in vivo may be carried out with considerable efficiency, taking into account the multiplication of the infectious virions.

The following description illustrates insertion of a human gene or cDNA fragment into the AEV vector. After digestion with restriction enzymes, such as EcoRI and NotI, specifically selected gene or random selected human cDNA fragments can be inserted into an AEV vector such as pAEV2LTRdelta (U.S. Pat. No. 4,957,865). All the recombinant plasmids can be characterized by restriction mapping or directly DNA sequencing. To produce the transmissible viruses, the recombinant plasmid pAEV2LTRdelta can be transfected in the presence of DNA of the helper virus (pRAV2) into secondary cultures of chick embryo fibroblasts. Cells are maintained in liquid medium and subcultured at regular intervals. Cells are maintained in culture at 37° C. and with 5% of $CO_2$. The cells are subcultured regularly every 3 or 4 days. The culture medium is composed of DMEM (Gibco) supplemented with 10% of foetal calf serum, 2 mM glutamine, 2.2 mg/ml of sodium bicarbonate, 100.mu.g/ml of streptomycin and 100 iu/ml of penicillin.

The stocks of recombinant virus can be titrated for their drug selection according to the technique of counting of colonies. For this purpose, 1 ml of diluted viral suspension is inoculated on cultures of fresh fibroblasts. The cultures are then selected with drug such as G418. The titer of the virus is given by the number of colonies of transformation per dish multiplied by the dilution of the suspension of inoculated virus. The titer is expressed in FFU (focus forming unit) per ml. By centrifugation of viral stock, the virus can be pelleted and re-suspended in serum free cell culture medium. This viral re-suspension preparation (1 ml) can be directly used for the animal injection in the range of 106 ml.

Delivery via SNV vector

Spleen Necrosis Virus (SNV) can also be designed for the purpose of avian cell gene transduction to immunize the chicken. The use of a spleen necrosis virus (SNV)-based retroviral vector has been demonstrated (Pathak et al., (1990) "Broad Spectrum of in vivo Forward Mutations, Hypermutations and Mutational Hotspots in a Retroviral Shuttle Vector after a Single Replication Cycle. Substitutions, Frameshifts and Hypermutations", Proc. Natl. Acad. Sci. USA 87, 6019–6023). The SNV based vector for the gene delivery application is also summarized by Dounburg Ralph in the WO 00/09730 and Pathak and Vinay K in U.S. Pat. No. 5,714,353. After SNV based vector is packaged in SNV permissive D17 dog cells, the recombinant SNV viral particle, which carries a human gene, can be used for the transduction of avian cell efficiently. Such SNV-retroviral shuttle vectors, designated DHH—N-2neo and JJ-A2neo, were deposited the American Type Culture Collection (ATCC), 13201 Parklawn Drive, Rockville, Md., 20852, and has been accorded ATCC Accession Number 97861 and 75780, respectively.

Delivery via Adenovirus Vector

Adenovirus is a large and diverse family of viruses. Adenoviruses have been isolated from many living species, including man and other mammals, as well as a variety of birds, particularly chicken. One group of virus, Aviadenoviradae, which is defined by its avian host range, can infect avian cell efficiently.

Adenovirus vectors are capable of high level expression of carried exogenous proteins, because transcription from the major late promoter of adenovirus is very efficient and high level translation is accompanied by host protein synthesis shut-off in the late stage of viral infection, thus facilitating protein isolation. For example, human adenoviruses can replicate efficiently to very high titers ($10^9$–$10^{10}$ pfu/ml) in human cells, as well as in other mammalian cells; and adenoviruses can produce their late proteins at a level that reaches 30 to 40% of total cellular proteins. Adenovirus vectors can also be propagated in suspension cultures thereby demonstrating a clear potential for large-scale production.

Gene delivery using Aviadenoviradae based vector into avian species, e.g., chicken, in vivo has been demonstrated in the WO 94/24268. Briefly, FAV CF20 virus was selected and constructed into commonly used vector form to carry CMV arly (CMVIE) promoter and SV40 polyadenylation signal. As TK gene or other drug selection genes such as zeocin resistant gene can be constructed and expressed as selection marker gene, this vector can be sued for expressing target cDNA or gene fragments in avian cells.

Construction and infection of recombinant adenoviral vectors into host cells are known in the art. For example, the procedures disclosed in U.S. Pat. No. 5,518,913 can be used. The viral vector disclosed in U.S. Pat. No. 5,518,913 includes an expression cassette comprising sequentially a transcription promoter, a high efficiency leader, at least one splicing signal, an enhancer-like sequence, a cloning site and a plurality of polyadenylation sites. According to U.S. Pat. No. 5,518,913, recombinant protein production, in cells infected with the recombinant adenovirus, can approach levels as high as 15–20% of total cellular proteins and can be used as animal immunization antigen.

The following description illustrates the use FAV CF20 vector in the present processes and methods. The avian based packaging cells can be generated using avian cells which are transfected with FAV CF20 viral E1a gene and can be manipulated in the same way as 293A (adherent) cells, which are derived from human kidney fibroblast transformed with Ad5 DNA and express the E1A and E1B proteins constitutively, are manipulated. The avian cells can be obtained from the ATCC and cultured in Dulbecco's modified Eagle's medium (DMEM; Gibco Laboratories), supplemented with 10% fetal bovine serum (FBS), glutamine and antibiotics. FAV CF20 can be used as the parent virus in all the viral constructs, and recombinant Ad are propagated by infecting monolayer AD packaging cells. Avian help virus can be created the same way as AdRed-1, a helper-free Ad recombinant expressing the HSV-2 ribonucleotide large subunit R1, is created (Huang et al., 1988, Virology 163:462–470). Large-scale production of Ad stocks is done by infecting exponentially growing packaging cells ($0.5 \times 10^6$ cells/mL) at a MOI 10–50 PFU/cell and harvesting the infected cells at 72 hours post-infection. The cell pellet is then resuspended in fresh Joklik's modified medium at a cell density of $1 \times 10^8$ cells/ml and virions are released by three to six cycles of freezing and thawing. Adenovirus titers are determined by plaque assays on packaging cells. Cell counting is performed using a hemacytometer, and viability is determined by trypan blue dye exclusion.

All recombinant DNA molecules can be constructed by standard cloning and site-directed mutagenesis procedures and propagated in competent *E. coli* cells, e.g., DH5 cells. The transfer vector based on FAV CF20 can be derived from FAV M11 (WO 94/24268) by sequentially subcloning human cDNA fragments into the vector with compatible NotI ends.

As a general overview, the coding region of the desired human cDNA gene can be first cloned in transfer vectors at the unique NotI cloning site, downstream of the strong CMVIE promoter. The resulting recombinant plasmid is then rescued into the genome of the adenovirus vector by in vivo homologous recombination between overlapping sequences on the linearized plasmid and the large right-end fragment of the FAV CF20 genome, upon cotransfection of avian packaging cells. This cell line constitutively expresses the avian Ad E1 gene product, which is essential for the helper-free propagation of FAV CF20 derived recombinants. Digestion of the help viral DNA with unique single cut prior to transfection allows for obtention of recombinant adenovirus at a frequency of 5–20%. The virions are purified through 2 consecutive CsCl gradients. A step gradient is performed by pouring 8 ml of CsCl 1.4 (53 gr+87 ml of 10 mM Tris pH 7.9) into SW 27 cellulose nitrate tubes, and then very gently on top pour 56 ml of CsCl 1.2 (26.8 gr+92 ml of 10 mM Tris pH 7.9). The aqueous phase containing the virions is then loaded on top of the discontinuous gradient (up to 22 ml/tube). The tubes are then centrifuged at 23K for 90 minutes at 0° C. The virus band is then collected by side puncture of the tubes. The band is diluted ½ in 50 mM Tris pH 7.5, 1 mM EDTA. A continuous gradient is then performed by using a gradient maker, to pour a continuous CsCl gradient in SW27 cellulose nitrate tubes using 12 ml of CsCl 1.4 and 14 ml of CsCl 1.2. The diluted virus suspension (8–10 ml) is then loaded very slowly on top of the gradient. The tubes are then centrifuged at 23K for 16–20 hours at 0° C. The virus band is then collected by side puncture, and dialyzed against 100 volumes of 10 mM Tris pH 7.9, 1 mM EDTA (3 changes), and finally against 100 mM Tris pH 8.5 1 mM EDTA.

The production of human cDNA derived protein can be done by infecting suspension cultures with the appropriate recombinant viruses. Ad infections are performed by mixing exponentially growing avian cells ($0.5 \times 10^6$ cells/mL) with a viral inoculum corresponding to a MOI of 25–50 PFU/cell and harvesting the infected cells usually at 48 hours post-infection. Twenty four hours post-infection, the medium is replaced. Again, the infected cells are harvested 48 hours post-infection, washed twice with ice-cold PBS, pelleted, resuspended in ice-cold buffer A (50 mM Hepes pH7.6, 2 mM DTT) and frozen at −80° C.

The time course of recombinant protein production by avian AD vector infected cells can be analyzed by preparing cell extracts from infected cells at various time points post-infection and subjecting them to SDS-PAGE. Cell extracts are prepared from infected cells at various time post-infection either directly on petri dishes or from aliquots of suspension cultures containing between 1 and $2 \times 10^6$ cells/ml. Briefly, cells are washed twice with PBS, lyzed in 100 ml of extraction buffer (80 mM tris pH6.8, 2% SDS, 10% glycerol), and frozen at −20° C. For gel electrophoresis, samples are thawed, passed several times through a syringe needle or sonicated to shear the DNA, and boiled 5 minutes in standard sample buffer. Protein concentration is determined in the cell extract using a calorimetric assay with BSA as standard. SDS-PAGE and Western blotting can be performed using procedures known in the art. Quantification of recombinant protein in cell extracts is done by densitometry scanning of Coomassie blue-stained gels or immunoblots with immunized chicken IgY antibody.

Delivery of Protein or Peptide Immunogen

For generating antibodies using the processes described in the above Section C, proteins or peptides encoded by the DNA sequence can be used as immunogens and delivered to the avian species. Any known methods for generating antibodies using protein or peptide immunogens can be used. The proteins or peptides can be chemically synthesized according to the DNA sequence encoding them, can be produced recombinantly, or can be produced by a combination of chemical synthesis and recombinant production. Preferably, the protein or peptide immunogens are produced recombinantly.

In one example, a gene or DNA fragment can be cloned into bacterial expression vectors such as PBR322, pUC18, etc. The recombinant proteins can be expressed in bacterial strain such as HB101, DH5α. The recombinant proteins can be purified by conventional protein or peptide purification methods such as HPLC, HPLC, SDS-PAGE coupled with protein elusion from gel slice. The purified protein can then be used in immunizing the avian species.

Preferably, fusion proteins containing the protein or peptide immunogens, such as GST, His-tag, intein and CBD based fusion proteins can be used. Fusion proteins with thermally-responsive elements can also be used.

GST Fusion Expression Vector Construction and Protein Purification: Plasmid Construction:

Using methods known in the art, a target gene or cDNA fragment can be generated by the polymerase chain from specifically constructed cDNA library and cloned into the GST-fusion expression vector such as pGEX-2T (Amersharn-Phamacia Biotec, Uppsala, Sweden; GenBank Accession number U 13850). This plasmid contains a thrombin cleavage recognition sequence (Leu-Val-Pro-Arg-Gly-Ser (Inserted gene) between a sequence encoding a glutathione-S-transferase tag and the cloning site into which the cDNA sequence is inserted. The resulting plasmid, encoding the target cDNA as a fusion protein with a GST tag, can be transformed into bacterial cells after DNA sequence is confirmed.

Bacterial Growth:

The recombinant GST expression plasmid can be transformed into commonly used bacterial strains such as HB101 or BL21 (DE3). Transformed cells are grown on LB agar plates overnight with ampicillin selection, e.g., ampicillin present in the plates at 100 ug/ml.

All growth can be carried out at 37° C. A single colony from a plate of transformed *E. coli* is used to inoculate 2 ml of LB or Typ medium (16 g bactotrytone, 16 g bacto yeast extract, 5 g sodium chloride, 2.5 g potassium dihydrogen phosphate per liter) with ampicillin present at 100 ug/ml which is established for 3 hours with aeration. The colony can be inoculated into 250 ml of LB medium made with 10 g bacto-tryptone, 5 g yeast extract and 5 g sodium chloride and supplemented with ampicillin at 100 ug/ml and left to stand overnight. The next day, 25 ml aliquots of this culture is inoculated into 1 liter flask.

The 1 liter culture is frown with aeration to mid-log-phase growth (an optical density (Abs600) of 0.6–0.8 AU), where upon expression from the plasmid is induced with 0.4 mM isopropyl-b-D thioglactopyranoside (IPTG). Cells are harvested 4 hours later by centrifugation at 3,000 rpm in a Beckman J-6B swinging bucket centrifuge. The supernatant is discarded and the cell pellet is retained.

Cell Lysis and Clarification

The cell pellet, either immediately or after storage at −80° C. is re-suspended in 100 ml cold phosphate buffer saline (PBS). The bacteria can be lysed either by sonication or chemical lysis buffer such as PIERCE Inc B-PER lysis buffer. After sonication, 5 ml of 20% Triton X 100 (Sigma Inc) is added to give a final concentration of 1% and leave this mixing at 4° C. for 30 minutes, preferably with gentle agitation. The entire preparation is centrifuged at 12,000×g for 30 minutes at 4° C. Supernatant is retained and pellet is discarded.

Recombinant GST-Fusion Protein Purification

Fusion protein can be purified using commercially available kit such as PIERCE Inc GST Orientation Kit (Cat # 78201), or can be prepared using the following procedure:

Purification Bead Preparation

Glutathion sepharose 4B beads (Pharmacia) are prepared by taking 1.33 ml of commercial available 75% slurry and spinning it at 500×g in a 15 ml Falcon tube for 5 minutes. The supernatant is removed and 10 ml of cold PBS is added before mixing. The mixture is centrifuged at 500×g in a Falcon tube for 5 minutes. The supernatant is removed and the pellet is re-suspended with 1 ml of cold PBS to give a 50 slurry.

Affinity Purification

Affinity purification of the target recombinant GST fusion protein can be carried out by the following methods:

1: Add 2 ml of the 50% slurry to the cell supernatant;
2: Gently agitate the mixture at 4° C. for the 30 minutes;
3: Centrifuge the mixture of the beads and cell supernatant at 500×g for 5 minutes and remove and discard the supernatant;
4: Add 20 ml of PBS and re-suspend the beads. Centrifuge at 500×g in a 15 ml Falcon tube for 5 minutes, remove supernatant. Repeat this step for two more times; and
5: Elute protein with free glutathione solution and the eluted fusion protein can be directly used for chicken immunization, or the GST portion can be cleaved from the fusion protein before the protein is used in animal immunization.

Thrombin Cleavage of Protein:

To separate the GST tag from the recombinant target protein, the following protocol was followed:

Make thrombin (Sigma chemicals) stock solution up at 1,000 cleavage unit per ml in PBS. Add 20 ul of the thrombin stock solution to 1 ml of PBS and add this to the recombinant bound beads. Incubate for 12 hours at 4° C. with agitation. Spin at 500×g for 5 minutes and remove the supernatant. The recombinant in the supernatant can be further separated on the SDS-polyacrylamide gel. The eluted recombinant protein from SDS-PAGE gel or the directly sliced gel containing the recombinant protein can be used for the animal immunization.

Intein-Based Fusion Protein Expression and Purification System

Intein-mediated purification with an affinity chitin-binding tag is a novel protein purification system which utilizes the inducible self-cleavage activity of a protein splicing element, i.e., intein, to separate the target protein from the affinity tag (Chong, S., Montello, G. E., Zhang, A., Cantor, E. J, Liao, W., Xu, M-Q, Benner, J (1998) *Utilizing the C-terminal cleavage activity of a protein splicing element to purify recombinant proteins in a single chromatographic step. Nucl. Acids Res.* 26, 5109–5115.). It distinguishes itself from other purification systems by its ability to purify, in a single chromatographic step, a native recombinant protein without the use of a protease. A target protein is fused to a tag containing the intein and the chitin binding domain, which allows affinity purification of the fusion precursor on a chitin column. In the presence of thiols such as DTT, b-mercaptoethanol or cysteine, the intein undergoes specific self-cleavage which releases the target protein from the chitin-bound intein tag, resulting in a single-column purification of the target protein.

The commercially available system such as the IMPACT-CN system (New England Biolabs) contains expression vectors pTYB vectors, which allow fusion of the cleavable intein tag to either the C-terminus or N-terminus of the target protein. This flexibility in fusion protein construction maximizes the probability of successful expression and purification of a target protein. To allow the cloning of the same amplified target gene in either fusion construction, the same or compatible restriction sites are designed in the multiple cloning region of pTYB2 and pTYB 12 vectors. pTYB1 and pTYB11 vectors, on the other hand, allow the cloning of a target gene immediately adjacent to the intein cleavage site. This results in the purification of a native target protein without any vector-derived extra residues after the cleavage.

The pTYB vectors use a T7 promoter and the lac I gene to provide stringent control of the fusion gene expression.

Binding of the lac repressor to the lac operator sequence immediately downstream of the T7 promoter suppresses basal expression of the fusion gene in the absence of IPTG induction. The four tandem copies of the E. coli transcription terminator (rmB T1) placed upstream of the promoter minimize background transcription. The vectors also contain the origin of DNA replication from bacteriophage M13, which allows the production of single-stranded DNA by helper phage, e.g., M13KO7 helper phage (NEB #NO315) superinfection of cells bearing the plasmid. pTYB vectors carry the Ampr gene marker (the bla gene), which conveys ampicillin resistance to the host strain.

An affinity matrix is used for the isolation of the fusion precursor containing the target protein. Twenty ml of chitin beads (~50–100 μm in size) are supplied as a 38 ml slurry in 20% ethanol. The binding capacity, which has been tested using the control vector pMYB5, is 2 mg of eluted MBP protein per ml of chitin beads.

CBD-Based Fusion Protein Expression and Purification System

Cellulose is an attractive matrix for affinity purification and immobilization mainly because of its combination of excellent physical properties and low price. Cellulose is commercially available in many different forms, such as cotton wool, filters, beads, powders, fibers, hydrogel, membranes, and sheets of defined porosity. To exploit the characteristics of this matrix, investigators have used a protein domain that naturally binds to cellulose: the cellulose binding domain (CBD).

CBDs provide a specific means for linking enzymes or other proteins on cellulose:

(1) Many CBD fusion proteins have been produced, among them are CBD-Protein-A for the purification of IgG;

(2) CBD-Streptavidin for different applications uses biotinylated molecules;

(3) CBD-Alkaline phosphatase can be used; and (4). The high affinity of specific CBDs for cellulose, and low desorption rate, enables essentially irreversible, non-covalent immobilization.

Cellulose binding domains are found in nature as discrete domains in proteins, such as in cellulases (Gilkes, N. R., Warren, R. A. J, Miller, R. C., and Kilburn, D. G. (1988) *J. Biol. Chem.* 263, 10401–10407; Gilkes N. R., Henrissat, B., Kilburn, D. G., Miller, R. C., and Warren, R. A. J. (1991) *Microbiol. Rev.* 55, 303–315.), as well as in proteins that have no hydrolytic activity (Shoseyov, O. and Doi, R. H. (1990) *Proc. Nat. Acad. Sci. USA.* 87, 2192–2195. Shoseyov, O., Takagi, M, Goldstein, M. A., and Doi, R. H. (1992) Proc. Nat. Acad. Sci. USA. 89, 3483–3487. Goldstein, M. A., Takagi, M, Hashida, S., Shoseyov, O., Doi, R. H, and Segel, I. H. (1993) *J. Bacteriol.* 175, 5762–5768.). In cellulases, it is thought that CBDs concentrate the catalytic domains on the surface of the insoluble cellulose substrate. In proteins with no hydrolytic activity, the CBD is part of a scaffoldin subunit that organizes the catalytic subunits into a cohesive multi-enzyme complex known as a cellulosome (Bayer, E., Morag, E., and Lamed, V. R. (1994) *Trends Biotechnol.* 12, 379–386.). The cellulosome is responsible for efficient degradation of cellulosic substrates.

Cellulose is an unbranched homopolymer of β(1–4) linked glucose subunits. Crystalline cellulose presents a surface array of parallel, closely-packed cellulose chains to a CBD. Amorphous cellulose presents antiparallel or disordered chains to a CBD. The binding sites of families I, II, and III CBDs are adapted to binding to a surface, and the family IV CBD to single molecules. Not surprisingly, only family IV binds to soluble cellulose derivatives and also to cello-oligosaccharides.

CBDs differ in both their binding and elution properties with different cellulose matrices. All of the CBDs that bind to crystalline cellulose and chitin (a homopolymer of β[1–4] linked n-acetyl-glucosamine) have very similar affinities with binding constants in the micromolar range. The family I CBDs bind reversibly, whereas the family II and III CBDs seem to bind irreversibly. Even with protracted washing, CBD fusion proteins derived from families II and III do not desorb from cellulose. The "irreversible" nature of this binding is not entirely understood; however, it may be related to the characteristics of the CBD-cellulose interactions and the properties of the cellulose itself. Cellulose presents an array of multiple overlapping binding sites to CBDs. Also, binding is believed to be mediated by multiple reversible interactions between glucose molecules in the cellulose and amino acids in the CBD. Therefore, desorption would likely require the simultaneous breakage of multiple interactions without the reestablishment of those interactions on neighboring, overlapping binding sites. Although fusion of heterologous protein to a CBD has little effect on the affinity of the CBD for cellulose, it can affect desorption of the CBD from cellulose.

In practice, the CBD gene is linked to the gene of the protein of interest. The resulting fusion protein binds strongly to cellulose and ideally retains the biological activity of the fusion partner. Binding is stable over a wide range of conditions (pH 2–10, high and low salt concentrations). The fusion protein can be eluted from cellulose with distilled water in some cases (Ong, E., Gilkes, N. R., Warren, R. A. J, Miller, R. C., Jr., and Kilburn, D. G. (1989) *Bio/Technol.* 7, 604–607. Tomme, P., Gilkes, N. R., Miller, R. C., Jr., and Warren, R. A. J. (1994) *Protein Engineering* 7, 117–123.) with elevated pH, a high concentration of guanidinium HCl or urea; or with ethylene glycol, a common reagent used in hydrophobic chromatography of proteins. A chemical or protease cleavage site can be engineered between the CBD and the fusion partner enabling recovery of the target protein without the CBD.

Expression systems using CBDs derived from families II and III have been developed, such as pET and pBAC™ vectors which use three CBD domains by Novagen, Inc. and is called CBD Tag™ sequences. By simply insert the target gene or cDNA library DNA fragment into those CBD-fusion expression vector, the fusion protein can be purified and used for the chicken immunization.

Temperature-Based Protein Solubility Purification Technique

Thermally-responsive proteins or polypeptides can also be used in immunizing avian species. Elastin-like polypeptides (ELPS) are oligomeric repeats of the pentapeptide Val-Pro-Gly-Xaa-Gly that undergo a reversible inverse temperature transition. They are highly soluble in water below the inverse transition temperature (Tt) but undergo a sharp (2–3° C.) phase transition when the temperature is raised above Tt, leading to desolvation and aggregation of the polypeptide. As experimental data recently published by Dan E. Meyer, the target protein can be fused to ELP domain such as ELP 30 or ELP 60 to purify the recombinant protein (Dan E. Meyer & Ashutosh Chilkoti, *Purification of recombinant protein by fusion with thermally-responsive polypeptides. Nature Biotechnology.* Vol17, pp: 1112–1115, 1999). Advantages of this method, termed" inverse transition cycling" include technical simplicity, low cost ease of the scale-up, and capacity for the multiplexing. As gene or gene fragment is inserted into ELP domain based vector, the target protein can be easily purified by temperature-dependent centrifugation, and the purified protein can be used in the avian immunization directly.

Adjuvant

The type and quality of the adjuvant used are of critical importance in determining the immune response, which should, ideally, be the induction of high serum and egg yolk antibody titers. The use of an adjuvant, especially FCA, can lead to a local tissue reaction at the injection site (Wanke, R., Schmidt, P., Erhard, M. H., Sprick-Sanjose Messing, A., Stangassinger, M., Schmahl, W. & Hermanns, W. (1996). *Freundsches komplettes Adjuvans beim Huhn: effiziente Immunostimulation bei gravierender lokaler inflammatorischer Reaktion. Journal of Veterinary Medicine* 43. 243–253.). In general, the expected antibody response can be generated by using an oil emulsion-type of adjuvant, such as Freund's incomplete adjuvant (FIA). No differences have been seen in the IgY response when FIA has been used for the primary immunization instead of FCA. Other types of adjuvant can also be used, such as Specol (Boersma, W. J. A., Bogaerts, W. J. C., Bianchi, A. I. J. & Claassen. E. (1992). *Adjuvant properties of stable water-in-oil emulsions: evaluation of the experience with Specol. Research in Immunology* 143: 503–512; product no. 792500, ID-DLO, Lelystad, The Netherlands) and the lipopeptide, Pam3-Cys-Ser-(Lys)4. The adjuvants AlPO4, Al(OH)$_3$ and saponin have been found to induce only very low antibody responses. Thus, it is important to first test the efficacy and quality of emulsion-type adjuvants according to standardized procedures (Herbert, W. J. (1967) *Methods for the preparation of water-in-oil and multiple emulsions for use as antigen adjuvants, and notes on their use in imminization procedures. In Handbook of Experimental Immunology* (ed. D. M. Weir), pp. 1207–1214. Oxford: Blackwell).

Antigen Dose

Initially, various concentrations of the antigen should be combined with the adjuvant, since the immune response is influenced by the type of antigen.

Vaccination Volume

It is usual to vaccinate chickens that are at least 7 weeks of age, preferably at two injection sites, with volumes of about 0.5–1 ml. The total volume injected will affect the tissue reaction induced.

Route of Injection

For practical and economic reasons, chickens kept under field conditions are vaccinated intramuscularly (i.m.) in the breast muscle. In the laboratory, chickens can also be vaccinated subcutaneously (s.c.) in the neck. With very young animals, it may be preferable to inject i.m. in the breast muscle, because s.c. injections are more difficult to perform and can therefore cause more distress. Intramuscular injection in the leg should be avoided, since this could lead to lameness.

Vaccination Frequency

The total number of vaccinations required will depend upon the type and dose of the antigen, as well as on the particular adjuvant employed. In any case, at least two immunizations should be given. If the antibody titers begin to decrease, booster immunizations can be given during the laying period.

Vaccination Interval

A primary vaccination and a booster should be given before the laying period, with an interval between these of about at least 6 weeks for emulsion-type adjuvants and about 4 weeks for lipopeptide adjuvants. Yolk antibody titers should be checked 14 days after the last immunization; if the antibody titers are low, revaccination should be considered.

Time for which Chickens can be Used

In principle, chickens can be used for the whole laying period, depending on the antibody titers induced. It is desirable to start with a group of chickens, and to select high responding animals which can then be kept for a longer period of time.

The following is an exemplary immunization protocol:

Adjuvant and volume: Equal volume, most of time about 0.4 ml, of Freund's complete adjuvant, mixed with 100–200 ug antigen in 0.4 ml PBS buffer;

Injection site: For young laboratory chickens, Intramuscular (field studies) and for older laboratory chickens, subcutaneous, both with an injection volume <1 ml;

Injection frequency: 2–3 times with boosters during laying period;

Vaccination interval: 4 weeks; and

Use of chickens: entire laying period (about 1 year).

E. Antibody Arrays and uses Thereof

In another aspect, the present invention provides an array of antibodies attached on a solid surface.

Any antibodies, whether polyclonal, monoclonal, single chain, Fc fragment, Fab fragment, F(ab)$_2$ fragment, or a mixture thereof, can be used to produce the antibody arrays. Preferably, the array comprises antibodies that specifically bind substantially to proteins or peptides encoded by a set of pre-selected DNA sequences isolated from a biosample. The set of pre-selected DNA sequences can be a cDNA library, such as a cDNA library isolated from animal, plant, fungus and bacterium cells. Preferably, the cDNA library is isolated from human cells. The cDNA library can be a specialized cDNA library, such as a tissue or organ specific cDNA library, a developmentally-regulated cDNA library, or a cDNA library is isolated from physiologically normal or physiologically abnormal cells. Also preferably, the antibodies used in the array are produced by the processes described in the above Sections A and B.

As used herein, the word "array" shall be taken to mean any ordered arrangement of a plurality of specified integers, including both liner and non-linear arrangements of a plurality of antibodies or antibody variants or derivatives. The array can be arranged on a grid, such as in microtitre wells, on a membrane support or silicon chip, or on a grid comprising a plurality of polymeric pins.

The array can be produced on any suitable solid surface, including silicon, plastic, glass, polymer, such as cellulose, polyacrylamide, nylon, polystyrene, polyvinyl chloride or polypropylene, ceramic, photoresist or rubber surface. Preferably, the silicon surface is a silicon dioxide or a silicon nitride surface. Also preferably, the array is made in a chip format. The solid surfaces may be in the form of tubes, beads, discs, silicon chips, microplates, polyvinylidene difluoride (PVDF) membrane, nitrocellulose membrane, nylon membrane, other pourous membrane, non-porous membrane, e.g., plastic, polymer, perspex, silicon, amongst others, a plurality of polymeric pins, or a plurality of microtitre wells, or any other surface suitable for immobilizing proteins and/or conducting an immunoassay.

The antibodies can be attached to the solid surface by any methods known in the art (see generally, WO 99/39210, WO 99/40434). For example, the antibodies can be attached directly or through linker(s) to the surface. The antibodies can be attached to the surface through non-specific, specific, covalent, non-covalent, cleavable or non-cleavable linkage(s). The cleavable linkage can be cleavable upon physical, chemical or enzymatic treatment. The arrays can be arranged in any desired shapes such as linear, circular, etc.

In one example, antibody array can be printed on a solid surface using pins (passive pins, quill pins, and the like) or spotting with individual drops of solution (WO 99/40434). Passive pins draw up enough sample to dispense a single spot. Quill pins draw up enough liquid to dispense multiple spots. Bubble printers use a loop to capture a small volume which is dispensed by pushing a rod through the loop. Microdispensing uses a syringe mechanism to deliver multiple spots of a fixed volume. In addition, solid supports, can be arrayed using piezoelectric (ink jet) technology, which actively transfers samples to a solid support. In addition, the methods disclosed in WO 95/35505 can also be used. The method and apparatus described in WO 95/35505 can create an array of up to six hundred spots per square centimeter on a glass slide using a volume of 0.01 to 100 nl per spot. Suitable concentrations of antibody range from about 1 ng/$\mu$l to about 1 $\mu$g/$\mu$l. Further, other methods of creating arrays, including photolithographic printing (Pease, et al., PNAS 91(11):5022–5026, 1994) and in Situ synthesis can be used.

Methods for covalent attachment of antibodies to a solid support are known in the art. Examples of such methods are found in Bhatia, et al., *Anal. Biochem.* 178(2):408413, 1989; Ahluwalia, et al., *Biosens. Bioelectron.* 7(3):207–214, 1992; Jonsson, et al., *Biochem. J.* 227(2):373–378, 1985; and Freij-Larsson, et al., *Biomaterials* 17(22):2199–2207, 1996, all of which are incorporated by reference herein in their entirety.

Methods of reducing non-specific binding to a solid surface are well known in the art and include washing the arrayed solid surface with bovine serum albumin (BSA), reconstituted non-fat milk, salmon sperm DNA, porcine heparin, and the like (see Ausubel, et al., *Short Protocols in Molecular Biolog,* 3rd ed. 1995).

A method for assessing proteomics profile of a biosample is also provided herein, which method comprises: 1) dividing a plurality of antibodies into an unlabelled portion and a labeled portion; 2) attaching the unlabelled antibodies on a solid surface to form an array of unlabelled antibodies on said solid surface; 3) contacting said array of unlabelled antibodies formed in step 2) with a biosample to retain antigens contained in said biosample that specifically bind to said unlabelled antibodies; and 4) detecting said retained antigens by contacting said retained antigens with said labeled antibodies, thereby proteomics profile of said biosample is assessed. Preferably, the plurality of antibodies used in the above methods are produced and characterized against a plurality of antigens encoded by a set of pre-selected DNA sequences isolated from a bio-sample via a process comprising the steps: 1) cloning each of said DNA sequences into a dual-expression vector that is capable of expressing said DNA sequences in avian cells, non-avian cells or in vitro expression systems; 2) delivering said DNA sequence in said dual-expression vector formed in step 1), or mRNA or protein encoded by said DNA sequence, or a mixture thereof, to an avian species in an amount sufficient to induce detectable production of antibodies to an antigen encoded by said DNA sequence, and recovering said antibodies from said avian species; 3) delivering said DNA sequence, or mRNA encoded by said DNA sequence, or a mixture thereof, which is delivered to said avian species in step 2), to said non-avian cells, and recovering proteins or peptides encoded by said DNA sequence from said non-avian cells, or expressing and recovering proteins or peptides encoded by said DNA sequence in said in vitro expression systems; and 4) conducting immunoreactions between said antibodies recovered in step 2) with said proteins or peptides recovered from step 3) to characterize the immunospecificity of said antibodies.

A method for identifying physiologically distinguishable markers associated with a physiologically abnormal bio-sample is further provided herein, which method comprises: 1) assessing proteomics profile of said physiologically abnormal bio-sample through the above-described method; 2) assessing proteomics profile of a comparable physiologically normal bio-sample through the above-described method; and 3) comparing the proteomics profile obtained in step 1) with the proteomics profile obtained in step 2) to identify physiologically distinguishable markers associated with a physiologically abnormal bio-sample. Preferably, the physiologically abnormal bio-sample is isolated from an organism, preferably mammals or humans with a disease or disorder, and the method is used in prognosis, diagnosis, or monitoring treatment of such diseases or disorders. The exemplary the diseases or disorders that can be monitored by the present methods include cancers, immune system diseases or disorders, metabolism diseases or disorders, muscle and bone diseases or disorders, nervous system diseases or disorders, signal diseases or disorders, or transporter diseases or disorders.

A method for identifying a substance that modulates proteomics profile of a bio-sample is further provided, which method comprises: 1) assessing proteomics profile of a bio-sample through the above-described method in the presence of a test substance; 2) assessing proteomics profile of said bio-sample through the above-described method in the absence of said test substance; and 3) comparing the proteomics profile obtained in step 1) with the proteomics profile obtained in step 2), whereby the proteomics profile obtained in step 1) is different from the proteomics profile obtained in step 2) identifies the test substance as a modulator of said proteomics profile of said bio-sample. Although the method can be used in screening a single test substance at a time, the method is preferably used in a high-throughput format, i.e., a plurality of test substances are tested simultaneously.

As used herein, "test substance" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on the promoter to be analyzed is determined by the disclosed and/or claimed methods herein. Any substances can be screened using the present screening methods for finding drug candidates for modulating proteomics profile of a biosample. In a preferred embodiment, a combinatorial library is used in the screening assays. Methods for synthesizing combinatorial libraries and characteristics of such combinatorial libraries are known in the art (See generally, *Combinatorial Libraries: Synthesis, Screening and Application Potential* (Cortese Ed.) Walter de Gruyter, Inc., 1995; Tietze and Lieb, *Curr. Opin. Chem. Biol,* 2(3):363–71 (1998); Lam, *Anticancer Drug Des.,* 12(3):145–67 (1997); Blaney and Martin, *Curr. Opin. Chem. Biol.,* 1(1):54–9 (1997); and Schultz and Schultz, *Biotechnol. Prog.,* 12(6):729–43 (1996)).

The above described processes, methods and antibody arrays can be used for identifying physiologically distinguishable markers associated with a physiologically abnormal bio-sample, or for identifying substances that modulate proteomics profile of a biosample.

F. Integrated Databases and Methods of Producing and Using Thereof

The present invention further encompasses integrated databases for identification of genes and proteins (IDIGAP).

The basic concept of IDIGAP is a development of the AMIGAP technology. The key point is the establishment of an integrated-database system that includes, but is not limited to, genomic, cDNA, expression vector, recombinant protein, and antibody databases, which integrated-database system forms an bioimformatic network for identification of genes and proteins. In one aspect, the method for producing such an integrated-database system uses immunization of chicken or other avian species with nucleic acid or recombinant proteins as immunogens to generate avian antibodies, e.g., IgYs, with a broad recognition spectrum in a high-throughput format.

Figure 14:
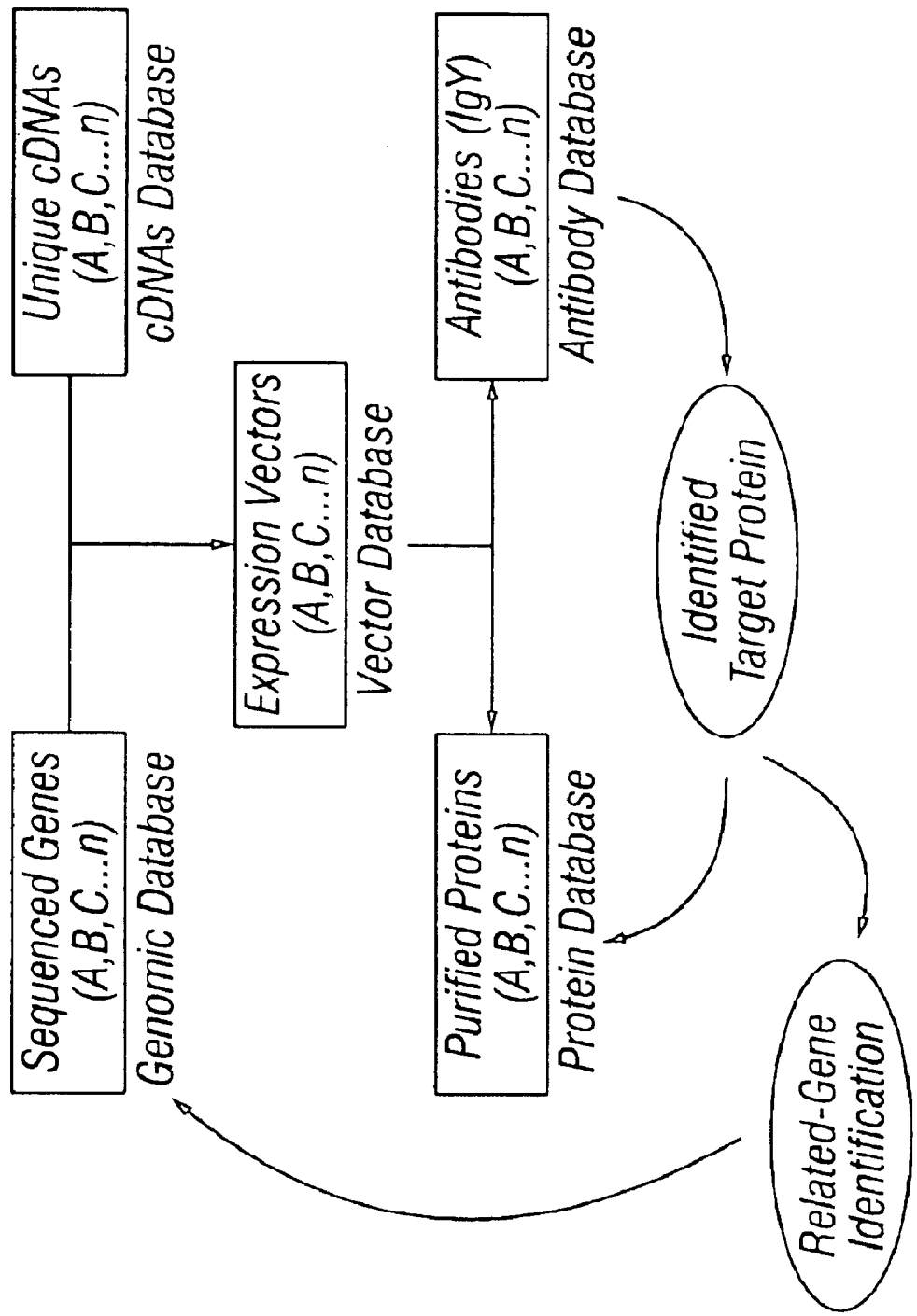
FIG. 14 illustrates the concept of the Integrated Databases for Identification of Genes and Proteins (IDIGAP). Shown in the figure are five databases, i.e., genomic, cDNA, expression vector, recombinant protein, and antibody databases, with their relationship and linkage structure. The network formed by the databases has the items corresponding to each other in each individual database so that the network can be used for determination of quantitative or qualitative changes of a given protein in tissues or cells. The protein identified is considered as a target protein which can be used for further identification of its location, function, or relation to certain biological or physiological, or pathological status. The identity of the target protein can be used to pick out the corresponding gene that has the same identification label in the genomic database.
Figure 15:
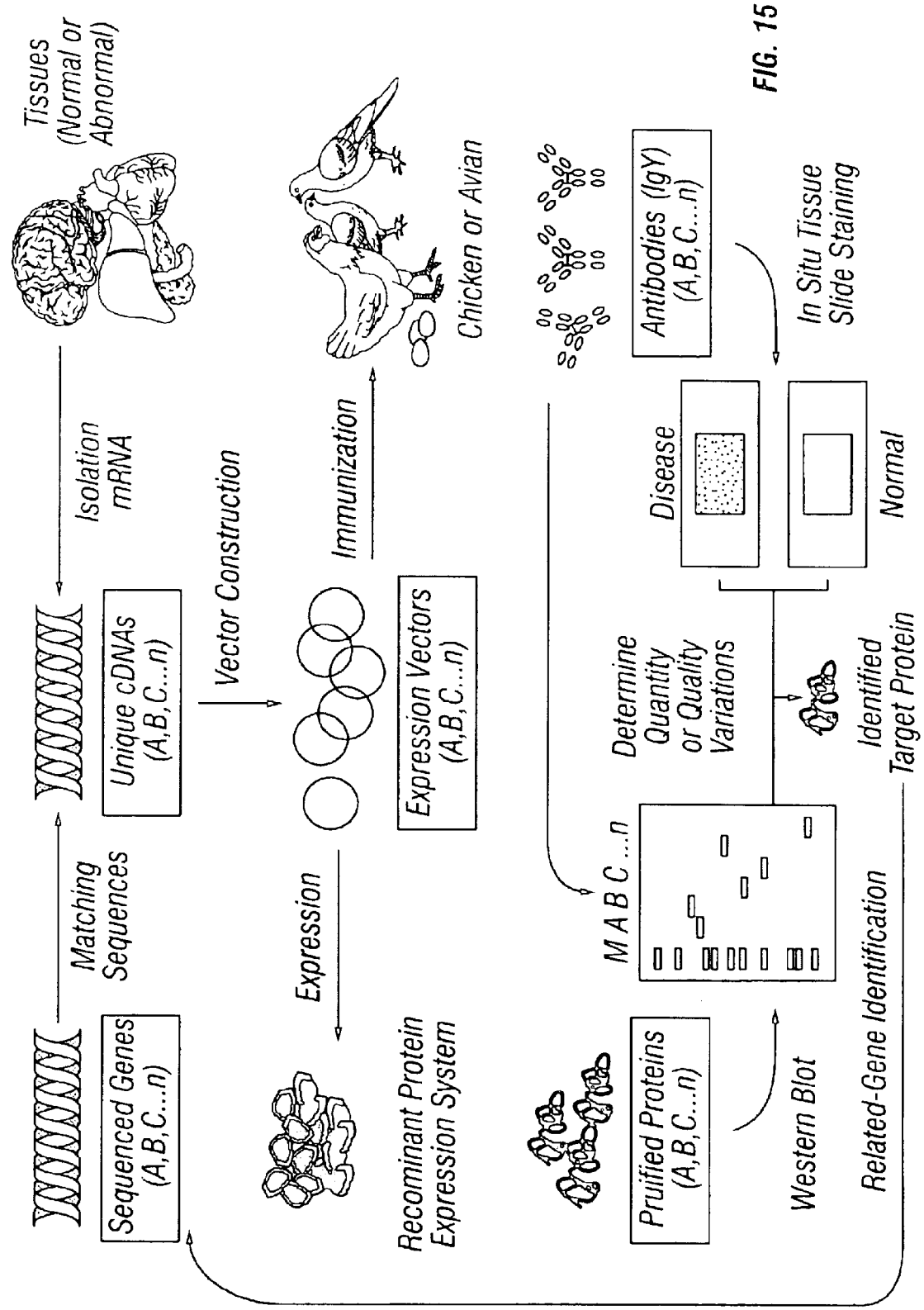
FIG. 15 illustrates exemplary use of the IDIGAP. Shown in the figure is the process and specific steps for application of the IDIGAP technology. Specifically, a process utilizing IDIGAP for identifying a disease-related protein and gene is depicted.
Figure 16:
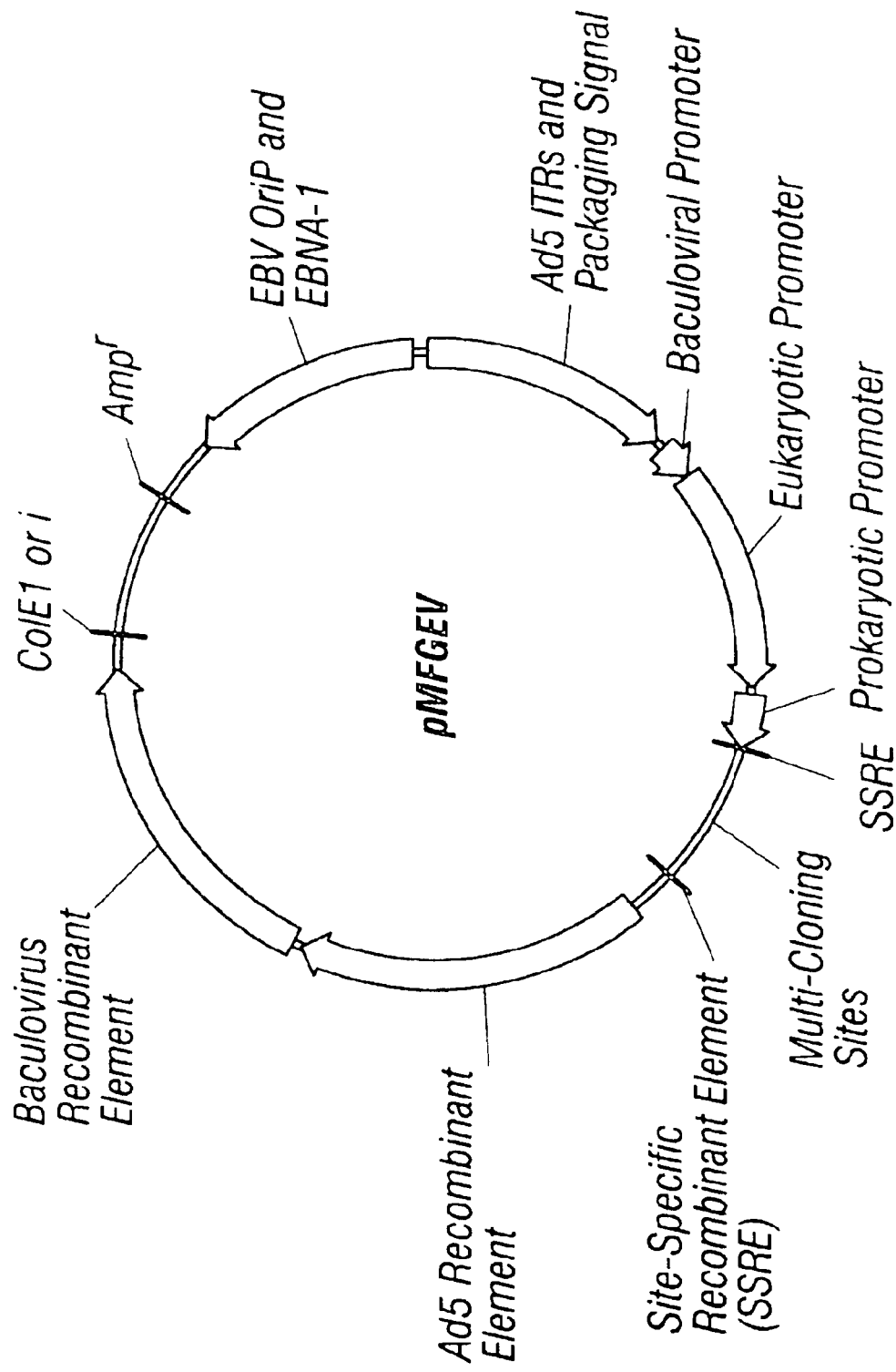
FIG. 16 illustrates an exemplary multi-functional gene expression vector (pMFGEV).

FIG. 14 summarizes the inter-relationship of the five databases and its usage in identification of the target protein and related gene. FIG. 15 illustrates a specific process of application of IDIGAP for identifying a disease-related protein and gene. In the illustrated process, mRNAs can be isolated from one or more tissues of interest that are normal or abnormal. cDNA libraries can be made from the mRNA to form cDNA databases. The cDNA can be sequenced and numbered with identities, e.g., A, B, C, . . . n. The sequence information of each cDNA can be used for constructing genomic databases with the numbering of each gene or sequence corresponding to the cDNA database. The cDNA can also be cloned in a dual-expression vector system to form a vector database, again with the corresponding numbering. The vectors can be, on one hand, used for generating recombinant proteins through expression system such as bacterial, yeast, baculovirus system, and on the other hand, used for immunization of chicken or other avian species. These two processes can generate purified recombinant proteins and avian antibodies, e.g., IgYs, that can form two separate databases with the corresponding numbering as the vector database. At this point, an inter-related databases network is established. By using the antibodies to screen tissue slides, disease related proteins can be identified. The related genes can then be identified through the database network.

In one specific embodiment, the present invention encompasses an integrated database for identification of genes and proteins, which integrated database comprises a genomic sequence subdatabase, a cDNA sequence subdatabase, a dual expression vector subdatabase which provides information for a plurality of vectors that are capable of directing expression in an avian species and in a non-avian species or an in vitro expression system, a protein sequence subdatabase, an antibody subdatabase and means for linking information in one subdatabase to information in other subdatabases, wherein said genomic DNA sequences, cDNA sequences, dual expression vectors, proteins or peptides and avian antibodies correspond to each other according to the central dogma and antigen-antibody binding specificity. Preferably, the dual expression vector directs expression in an avian species and in a non-avian species such as a bacterium, a yeast, an insect, or a mammal. Also preferably, the antibody subdatabase provides information for a plurality of IgY antibodies produced in the avian species.

Any known genomic sequence database including the genomic DNA or genomic RNA sequence database, cDNA sequence database, dual expression vector database which provides information for a plurality of vectors that are capable of directing expression in an avian species and in a non-avian species or an in vitro expression system, protein sequence database and antibody database can be used in the integrated database. For example, the publicly accessible genomic sequence database, cDNA sequence database and protein sequence database, including the ones listed at http:\\www.ncbi.nlm.nih.gov, can be used. In addition, the genomic sequence subdatabase, the cDNA sequence subdatabase, the dual expression vector subdatabase which provides information for a plurality of vectors that are capable of directing expression in an avian species and in a non-avian species or an in vitro expression system, the protein sequence subdatabase, and the antibody subdatabase can be constructed by any methods known in the art or any methods described in this Application. For example, the dual expression vector subdatabase which provides information for a plurality of vectors that are capable of directing expression in an avian species and in a non-avian species or an in vitro expression system and the protein sequence subdatabase can be constructed based on bioimformatic information identified by using the methods described in the above Sections C and D.

Once the requisite bioimformatic information are obtained, such information can be delivered or imported into known database format such as Excel, *Lotus*, Access, DB2, SQL Sever and Oracle, etc. The imported information can then be characterized or manipulated within each database using routine procedures or softwares, many of which are built-in elements of the databases. Means can also be provided for linking, e.g., importing, exporting, indexing or synchronizing, information among different databases. For example, SQL Net or Net 8 software can be used for such purposes. In addition, many databases have internal structures or languages for enabling or facilitating such cross-database exchanges.

In another specific embodiment, the present invention further encompasses a method for generating an integrated library for identification of genes and proteins, which method comprises: 1) selecting and marking a plurality of DNA sequences from a genomic library; 2) selecting and marking a plurality of cDNA sequences from a cDNA library that correspond to said selected and marked plurality of genomic DNA sequences; 3) cloning said plurality of selected and marked cDNA sequences into a dual expression vector that is capable of directing expression of said plurality of selected and marked cDNA sequences in an avian species and in a non-avian species or an in vitro expression system; 4) producing a plurality of proteins or peptides encoded by said plurality of selected and marked cDNA sequences by delivering and expressing said dual vector containing said plurality of selected and marked cDNA sequences into said non-avian species or said in vitro expression system; and 5) generating antibodies from an avian species using said dual vector formed in step 3) via nucleic acid vaccination or using proteins or peptides formed in step 4) via protein or peptide vaccination, thereby forming an integrated library comprising a plurality of genomic DNA sequences, a plurality of cDNA sequences, a plurality of dual expression vectors containing said plurality of cDNA sequences, a plurality of proteins or peptides encoded by said genomic DNA or cDNA sequences, and a plurality of avian antibodies that specifically bind to proteins or peptides encoded by said genomic DNA or cDNA sequences, and wherein said genomic DNA sequences, cDNA sequences, dual expression vectors, proteins or peptides and avian antibodies correspond to each other according to the central dogma, i.e., the correlation between the nucleic acid sequence and the protein sequence, and antigen-antibody binding specificity. Preferably, the method further comprises a step of conducting immunoreactions between said antibodies generated in step 5) with said proteins or peptides generated in step 4) to characterize the immuno-specificity of said antibodies. Also preferably, the method further comprises a step of conducting immunoreactions between said characterized antibodies with a biosamples from which genomic library is isolated to determine the proteomics profile of the selected and marked plurality of genomic DNA sequences. Although a set of genomic DNA sequences is selected first and then corresponding cDNA sequences are selected in the above method, the cDNA sequences can be selected and marked first and such cDNA can be used for subsequent selection and marking of corresponding genomic DNA sequences.

In still another specific embodiment, the present invention further encompasses a method for generating an integrated database for identification of genes and proteins, which method comprises: 1) delivering bioimformatic information of the plurality of genomic DNA sequences, the plurality of cDNA sequences, the plurality of dual expression vectors, the plurality of proteins or peptides, and the plurality of avian antibodies obtained using the above-described methods into the corresponding genomic DNA, cDNA, dual expression vector, protein or peptide, and the avian antibody subdatabases; and 2) providing means for connecting the bioimformatic information from one subdatabase to any or all of the other subdatabases. Preferably, the method further comprises a step of delivering bioimformatic information of the immunospecificity of the avian antibodies obtained using the methods described in the above Section C into the integrated database. Also preferably, the method further comprises a step of delivering bioimformatic information of the proteomics profile of the selected and marked plurality of genomic DNA sequences, which can be obtained according to the methods described in the above Section C, into the integrated database.

This invention will be more completely described by means of the following examples, which are to be considered illustrative and not imitative.

G. EXAMPLES

Construction of Dual Functional Expression Vectors

For constructing pS&DV vector, pDual vector, purchased from STRATAGENE Inc. (La Jolla, Calif.), was used as template vector for amplification of both CMV/T7 promoter expression cassette. In 100 ul PCR reaction tube, 10 ng pDual plasmid DNA was heated to 95° C. for 5 minutes and then mixed with 10 pM of both CMV-1 (5'CACCCTGAATTGACTCTCTTTC3') (SEQ ID NO:1) and PacII-1 (5'ATATGAATTCTTAATTAAGATCTCCAT GGTGGCCTCTCCTTC3') (SEQ ID NO:2) oligos using standard PCR reaction (Promega PCR Kit). PCR reaction was performed as follow: 40 cycles at 95° C. for 1.45 minutes, 55° C. for 1.30 minutes, 72° C. for 2 minutes. Finally, the PCR product was further incubated at 72° C. for 10 minutes. The Products was named as Fragment I (0.75 kb). In the second tube, 10 ng pDual plasmid DNA was amplified by PCR using the above-described condition with oligo PacI (5'CGCGGAATTCGCGGCCGCTACCAGGT AAGTGTACC3') (SEQ ID NO:3) and oligo ter-2 (5'CGAGTAGTTTAAACAAAAAACCCCTCAAGTCCC G3') (SEQ ID NO:4). The Product was named as Fragment-II (0.6 kb). Both Fragments I and II (1 ug of each) were digested with EcoRI and then gel purified in 1% agarose. After the two fragments were ligated using T4 DNA ligase in 50 ul volume overnight at 16° C., 5 ul of ligation mixture were transferred into a new PCR tube and mixed with oligo CMV-1 and Ter-2 for PCR amplification using the same condition as described above. After the 1.36 kb PCR product was digested with PmeI, this 1.36 kb fragment was inserted into PmeI digested cloning vector pT7*. The final vector was named pS&DV.

For preparing the cloning vector pT7*, the purified pT7Blu(R) plasmid, purchased from Novagen Inc., was used as DNA template for PCR amplification. With 10 ng pT7Blu (R) plasmid, in 100 ul PCR reaction mixture, two oligos T7A and T7B were added into reaction and PCR was performed using the same condition as described above. (T7A: 5'AGATCTGTTTAAACCAGGTGGCACTMCGG3' (SEQ ID NO:5) and T7B: 5'AGATCTGTTTAAACAGCT-GTTTCCTGTGTGA3' (SEQ ID NO:6)). The 2.1 kb PCR product was then digested with BgLII and gel-purified for self-ligation. The resulting vector was named pT7* which carries two unique PmeI sites.

For constructing pS&DV-S vector which carries chicken IgY Vhl signal domain (MSPLVSSLLLLAALPGLMAA) (SEQ ID NO:7), two oligos were synthesized as follows: Linker-1:(5'AACCCTCTTCCATGAGCCCACTCGTCT CCTCCCTCCTGCTCCTGGCCGCCCT GCCAGGGCTGATGGCGGCC3') (SEQ ID NO:8), Linker-2: (5'CAGATCCTCTTCGAAGCTAGCGGCCGCGAA TTCTTAATTAAGGCCGCCATC AGCCCTGGCAG3') (SEQ ID NO:9). One ug of each of Linker-1 and Linker-2 oligo was mixed in 50 ul PCR reaction condition without Taq DNA polymerase, heated to 94° C. for 5 minutes, and then was slowly cooled to room temperature. After adding 2.5 units of Taq DNA polymerase, the PCR reaction was performed using the same condition as above but was only run for 10 cycles. The 105 bp PCR product was digested with Eaml 104-I and inserted into pDual vector's Eaml 140-1 site. The resulting vector was named pDual-S. Using pDual-S as the DNA template, the 1.5 kb DNA fragment which carries the gene expression cassette was generated by further PCR amplification with the CMV-1 and Ter-2 oligos. After PmeI digestion, the 1.5 kb DNA fragment was inserted into pT7* vector's PmeI site to generate the dual function vector pS&DV-S vector.

In Vivo Immune Response Mechanism Illustration Elicited by DNA Vaccination

The direct intracellular inoculation of DNA expression cassettes leads to the in vivo transfection of host cells. Expression of the plasmid-encoded protein may elicit an immune response. Secreted immunogens are ingested by phagocytosis and presented as peptide-MHC II complex by professional antigen-presenting cells. These cells can provide the primary activation signal, costimulatory ligands, and cytokines necessary to stimulate naive T cells. Stimulation of Th0 T cell with IL-4 leads to the development of Th2 CD4 helper T cell, which will secrete cytokine to promoter B cell development, including IL-4, II-5, II-6, and IL-10. Stimulation of Th0 cells with the proinflammatory cytokine IL-12 and IFN-γ leads to development of the Th1 CD4+ helper T cell. These cells secrete cytokines that will promoter the development of CD8+ cytotoxic T lymphocytes (Koprowski et al DNA vaccination/genetic vaccination. 1998. Springer-verlag Berlin heidelberg.).

ELISA Titering of the Chicken Immunized by Particle-Mediated DNA Delivery Experiments As illustrated in FIG. 5, three antigen cDNAs which is driven by CMV or SV40 promoter, respectively, were used for vaccinating chickens. Chicken strain used in this experiment, the Hy-line SC strain, was obtained from Hy-Line Inc. (Dallas Center, Iowa).

For each transfection, 1 ug of vector DNA coated on 0.5 mg of gold microparticles was loaded onto a Kapton macroprojectile as previously described (Williams, et al., *Proc. Natl. Acad. Sci.*, 1991, 88:2726–2730). The DNA was delivered into the target site (chicken back skin) using a handheld, helium-driven ballistic gene gun with equivalent of 200 ng plasmid (Sanford, et al., *Technique,* 1991, 3:3–16). The pressure in the gun was adjusted to 1200 psi. After DNA injection, at different post-injection day, the eggs from the immunized chickens were collected and stored at 4° C. and IgY was purified using the protocol described in § 6.8. In this experiment, repeated DNA injection with same amount of plasmid DNA was performed to observe the host immunoresponse for antigen.

To purify each of the corresponding antigen, i.e., HbxAg, HBV-pol and CD34 from *E. coli* for assaying the specificity and binding affinity of antibodies derived from the immunized chickens, HbxAg gene was cloned into pET3a (Wu et al, *Cell,* 1990, 63:687–695). The RNase H domain of the HBV polymerase protein was PCR amplified using Pol-1 and Pol-2 oligo, and inserted into pET28a NdeI-HindIII site. As described in the following section, human CD34 cDNA was obtained and inserted into PET 28a vector. All of the pET vectors were purchased from Novagen Inc. Each of the constructs was confirmed by DNA sequencing. Recombinant protein expression was assayed according to the Novagen Kit instruction (see also Studier et al., *Methods Enzymol.,* 1990, 185:60–89). Briefly, the constructed plasmids were transformed into BL21(DE3) competent cells, clones were transferred into 3 ml LB medium which contains carbenicillin (Sigma Inc. cat # C1389) or kanamycin, and cultured at 37° C. overnight. On second day, the culture was transferred into 500 ml LB medium with selection and shaking at 37° C. until $OD_{600}$ reached 0.45. Then 0.2 mM IPTG was added into the bacterial culture and the bacteria cells were cultured for two more hours. Cells were cooled on ice for 5 min and then harvested by centrifugation at 5000×g for 5 min at 4° C. The cell pellet was washed once with cold PBS buffer. The cells were resuspended in 50 ml Tris-buffer (50 mM Tris-HCl, 2 mM EDTA, pH 8.0) and disrupted by sonication. The sonicated samples were separated into soluble or insoluble (pellets) fractions by centrifugation at 5000×g for 5 min at 4° C. After the pellet were resuspended in 45 ml Tris-buffer containing 100 ug/ml lysozyme and 5 ml 1% triton X-100, 10 ul of both soluble and insoluble samples were loaded on 12.5% SDS-PAGE (BioRad mini-gel system) with untransformed bacteria samples as control. The gel staining showed that all three bacterially expressed proteins i.e., HbxAg, HBV-pol and CD34, were mainly found in the insoluble fraction.

Urea was added slowly to the 50 ml insoluble fraction to a final concentration of 8 M with stirring at 4° C. After the pellet was completely dissolved, the sample was further centrifuged at 5000×g for 5 min at 4° C. to remove the pellet and supernatant was loaded on a 3 ml His-Bind Resin column for purification of the recombinant proteins using the protocol suggested in the Novagen Inc.'s kit. After the washing steps, the purified protein was eluted from the column with 10 ml 1×strip buffer, which contains 6 M urea. The purified protein sample was transferred into a dialysis tube and was dialyzed against PBS overnight at 4° C. in 4 Liter volume. Finally, the protein sample in the dialysis tube was further concentrated into 1 ml volume by Amicon spin concentration column (Amicon Inc, MW cut of: 10,000 dalton). After checking protein concentration, 3 ul of purified protein were separated on 12.5% SDS-PAGE. The purity of the recombinant protein, measured by the density of protein bands using molecular densitometry (Molecular Dynamic Inc), is more than 93%.

Five ug of the purified bacterially produced antigen protein, in 200 ul PBS buffer, were coated on ELISA plate well at 4° C. overnight. After coated wells were washed once with BPS, 200 ul 5% BSA solution was added for further coating to block non-specific binding in the assay. Chicken IgY (1 mg/ml) purified by the PEG method after the DNA immunization (see § 6.8) was serially diluted, added into each coated well and incubated at 37° C. for 2 hours. After 5-time washing with PBS buffer, the HRP-labeled goat anti-chicken antibody (Sigma Inc., 1:10000 dilution) was added into the well and incubated for 1 hour. After 5-time washing with PBS, the substrate buffer was added and incubated for 15 min with ELISA reading every five minutes.

Figure 5A:
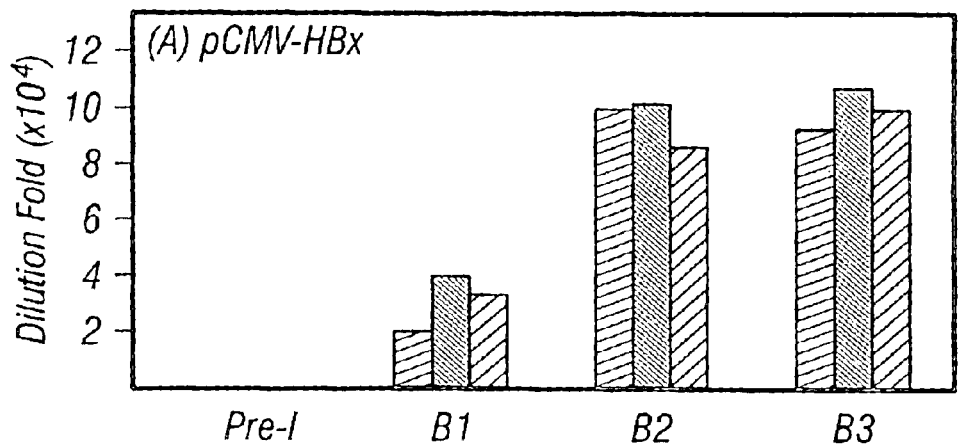
FIG. 5 depicts ELISA titering of antibody produced in chicken by DNA vaccination with three antigens encoded by pCMV-HBx, pCI-HBV-pol and pZeoSV2-hCD34.
Figure 5B:
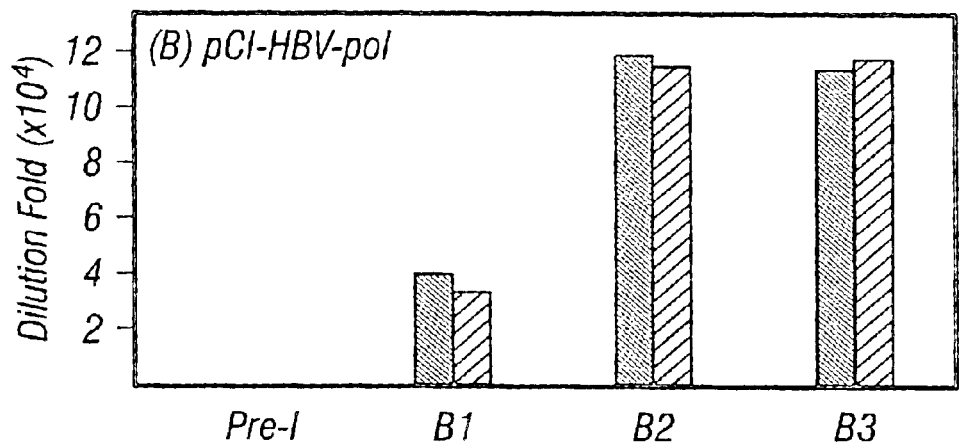
Figure 5C:
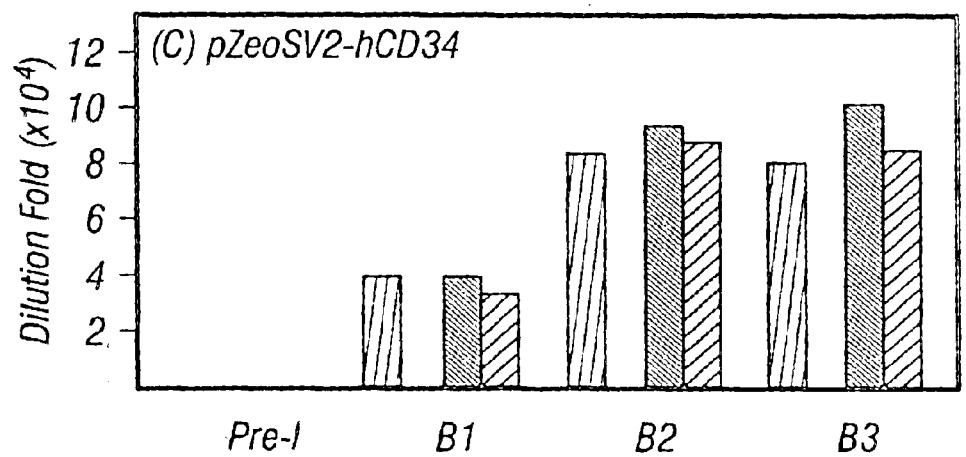
Figure 6:
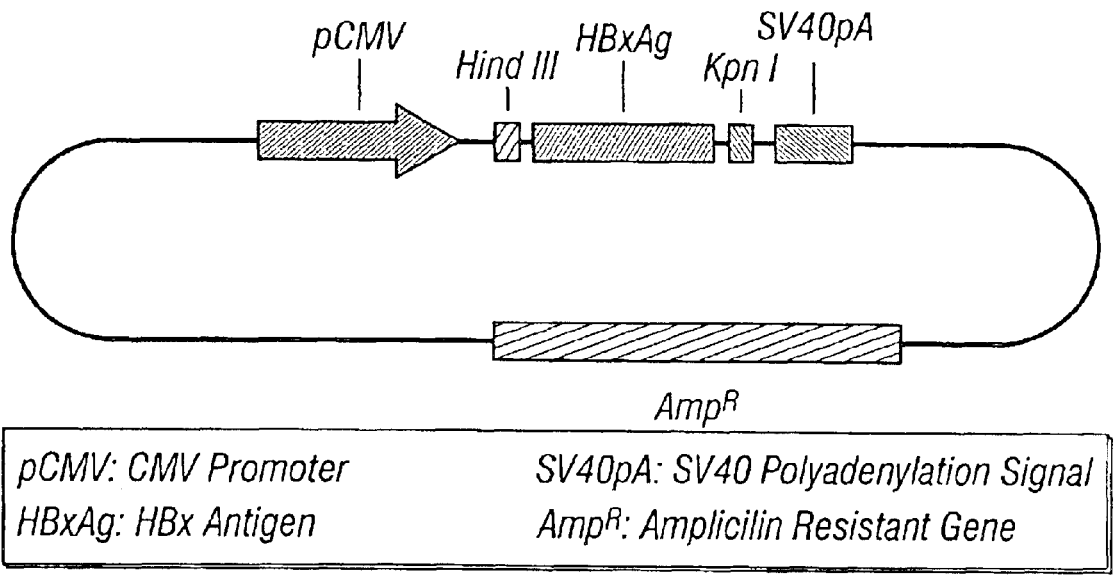
FIG. 6 depicts a restriction map of HbxAg antigen specific expression vector pCMV-HBx.
Figure 7:
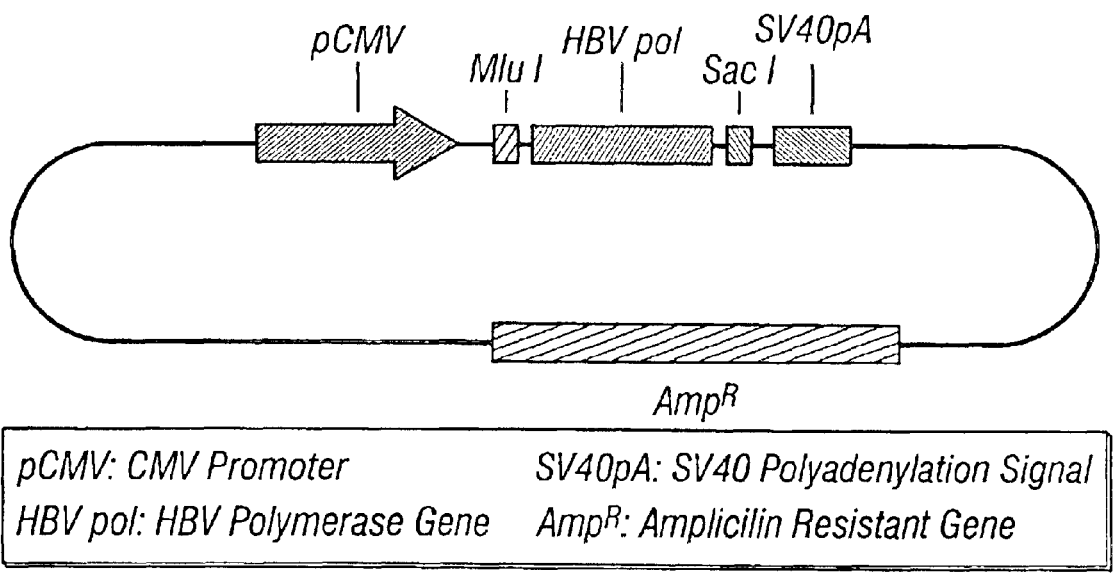
FIG. 7 depicts a restriction map of Hepatitis B virus Polymorantz antigen specific expression vector pCI-HBV-pol.
Figure 8:
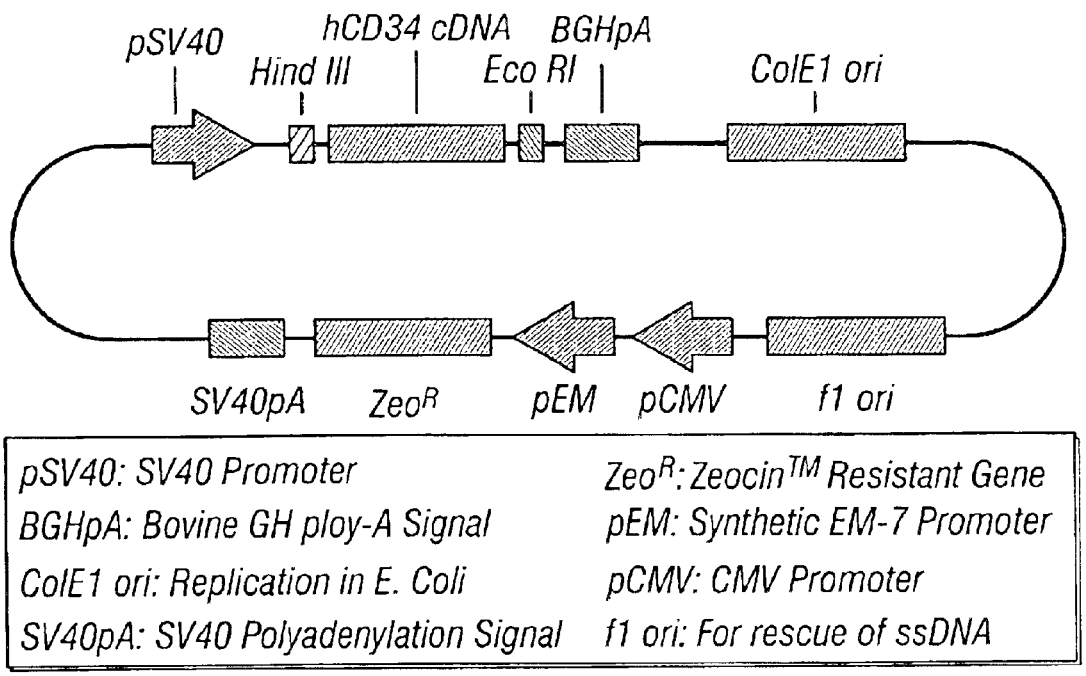
FIG. 8 depicts a restriction map of human CD34 antigen specific expression vector pZeoSV2-hCD34.

In FIG. 5, each of different bars represents different chickens. In FIG. 5A, chicken was immunized with pCMV-HBx vector; in FIG. 5B, chicken was immunized with pCMV-HBV-pol vector; and in FIG. 5C, chicken was immunized with pZeoSV2-hCD34. Assay time point is as the following: Preimmune (Pre); or 12 days after boost 1 (B1), Boost 2 (B2) and boost 3 (B3). Analysis of the multiple DNA vaccination host immuno-reaction data shows that 12 days after single DNA injection, chicken specific antibody production already reached the detectable level.

Construction of the PCMV-HBx Expression Vector

Construction of the hepatitis B X gene expression vector was performed as the following. Ten ng of pTKHH2 DNA (HBV full-length viral genome dimer plasmid) was mixed with MF18 (MF18:5'GGAAGCTTGCCGCCATGGCTG CTAGGCTGTGC3') (SEQ ID NO:10) and MF19 (MF19: 5'GTGGAGACGGATTAGTACCATGGCC3') (SEQ ID NO:11) oligo in 100 ul PCR reaction tube. HBV polymerase gene was PCR amplified in the following condition: at 95° C. for 1.30 minutes, at 55° C. 1.30 minutes and at 72° C. for 2 minutes; for a total of 40 cycles. Finally, the PCR product was incubated at 72° C. for 10 minutes. The 488 bp PCR product was gel purified and then digested with HindIII and KpnI. The digested HBx fragment was inserted into mammalian expression vector pTTW-I vector (Condreay et al., *J. Virology,* 1990, 64:3249–3258), which was digested with same enzymes to generate the pCMV-HBx plasmid.

The expression of the HBx protein was tested by transfecting the pCMV-HBx into human hepatocellular carcinoma cell line HepG2 cells 1×10⁶ HepG2 cells were seeded in 10 cm culture dish in 10 ml DMEM medium which was supplemented with 10% fetal calf serum at 37° C. in $CO_2$ incubator overnight. Four hours before the transfection, 10 ml fresh pre-warmed DMEM medium supplemented with 10% fetal calf serum was replaced. Five ug purified pCMV-HBx plasmid were mixed in calcium precipitation mixture according the manufacturer's protocol (Promega Inc.'s calcium transfection kit). After the mixture precipitated at room temperature for 30 minutes, the mixture was slowly dropped into HepG2 cells and cultured for 12 hours. Next day, 10 ml pre-warmed fresh medium was replaced and the cells were cultured for one more day.

Transfected cells were washed with 10 ml cold PBS buffer and cells were collected using rubber policeman in 1.5 ml PBS. After centrifugation, the cell pellet was resuspended in 100 ul $H_2O$, and 20 ul cell sample was mixed with same volume SDS-PAGE loading buffer and boiled for 3 minutes. The boiled sample was subjected to the max-speed Eppendorf centrifugation for 2 minutes and 5 ul of the supernatant were loaded on 12.5% gel for SDS-PAGE separation. The extracted cellular protein was demonstrated to be positive for HBxAg expression using Western Blot assay with specific rabbit anti-HBx antibody (1:800 dilution) (Wu et al., *Cell,* 1990, 63:687–695).

Construction of Hepatitis B Polymerase Antigen Specific Expression Vector

Construction of the hepatitis B polymerase (HBV pol) gene expression vector was performed as following. In 100 ul PCR reaction as described in § 6.4, pTKHH2 plasmid DNA template was mixed with oligos MF26 (5'AAGAGCTCGCCACCATGGCCCTATCCTATCAAC3') (SEQ ID NO:12) and HBVpol-2 (5'TCACCTTAAGGTG TTGGAAGGTGGTTTGA3') (SEQ ID NO: 13). The 868 bp HBV pol 5' end DNA fragment was gel purified and digested with SalI and EcoRI, then inserted into vector pGEM3Z (Promega Inc.) which was digested with the same enzymes to generate the plasmid pGEM3Zpol-5'. From pTKHH2 Vector, another 1638 bp 3'end of HBV polymerase DNA fragment was PCR amplified using pTKHH2 plasmid mixed with the following oligos, Pol-3(5'GGCCATGCAGTGGAA TTCCACTGCCTTCC3') (SEQ ID NO:14) and Pol-4 (5'AACCAAGCTTCACGGTGGTCTGGATGCAAC3') (SEQ ID NO: 15). The PCR product was digested with EcoRI and HindIII. The digested fragment was inserted into pGEM3Zpol-5'EcoRI-HindIII site to generate the 2874 bp full-length HBV polymerase gene. The resulting plasmid was named p3Zpol. The HBV polymerase gene was digested with SacI first and then filled in with Klenow reaction (Sambrook et al., *Molecular Cloning*, Second Edition, Plainview, N.Y. Cold Spring Harbor Press, 1989) to form a blunt end. After digestion with SalI again, the full-length polymerase gene was then inserted into pCI vector (Promega Inc.), which was digested with MulI, Blunted and then digested with SalI, to generate the pCI-HBV-pol expression vector.

The expression of HBV polymerase protein was also tested by transfecting the pCI-HBV-pol into human hepatoma cell line HepG2 as described in § 6.4. The extracted cellular protein was demonstrated to be positive using Western Blot assay with specific rabbit anti-HBV polymerase peptide antibody (Feitelson et al., *Clinics In Laboratory Medicine*, 1996, W. B. Saunders Com).

Construction of the pZeoSV2-hCD34 Expression Vector

In order to obtain human CD34 full-length cDNA for DNA vaccination, CD34 positive cell line KG-1a was used for RNA extraction (Simmons et al., J. Immunol, 1992, 148:267–271). Total RNA was purified from $1 \times 10^6$ cultured KG-1a cells by the technique described in Puissant et al., *BioTechniques*, 1990, 8:148–149 with minor modification. Briefly, $2 \times 10^6$ cultured KG-1a cells were suspended in 5 ml buffer (4 M guanidine thiocyanate, 25 mM sodium citrate, 0.5% sarkosyl, 0.1 M 2-mercaptoethanol, pH 7.0). The following reagents were added, punctuated by vortexing of the tube: 2 M sodium Acetate pH 4.0 (0.5 ml), Phenol (5 ml), and chloroform (1 ml). Following incubation on ice for 15 min, the tubes were centrifuged at 10,000 g (7,000 rpm) for 10 min. Isopropanol (5 ml) was added to the upper phase and incubated on ice for 10 min, followed by centrifugation as describe above. The RNA pellet was dissolved in 1 ml 4 M LiCL and transferred to a microcentrifuge tube. The original tube was rinsed with 0.5 ml LiCl and the pellet was vortexed for 5 min in the combined liquid. RNA was pelleted by centrifugation (10 min), resuspended in 1 ml 4M LiCl and pelleted again. The pellet was thoroughly resuspended in TE/0.5% SDS and extracted with an equal volume of chloroform/isoamyl alcohol (24:1). The aqueous phase was extracted a second time before precipitation of RNA by adding 2 M sodium acetate (0.1 ml) and isopropanol (600 ul). RNA was pelleted and resuspended in water.

One ug of the purified total RNA was used for reverse transcription (RT) reaction with oligo $dT_{18}$ primer, following the manufacturer's protocol (BRL Life Science Inc., RT kit). Full-length human CD34 cDNA was PCR amplified using oligo hCD34-1 (5'GAAGGATGCTGGTCCGCA GGGG3') (SEQ ID NO: 16) and hCD34-2 (5'CACCTAGCCGAGTCACAATTCG3') (SEQ ID NO:17) primers. The PCR reaction was performed at the following condition: at 95° C. for 1.30 minutes, at 53° C. for 1.30 minutes, at 72° C. for 2 minutes; and for a total of 40 cycles. Finally, the PCR product was incubated at 72° C. for 10 minutes. The 1.2 kb PCR product was directly inserted into the HincII digested pUC18 vector (Phamacia Inc). The resulting plasmid pUC18-hCD34 was confirmed to contain the full-length hCD34 sequence by DNA sequencing analysis using ABI 373 DNA sequencer and M13 primers.

After digestion of the pUCI 8-hCD34 with HindIII and EcoRI, the 1.2 Kb hCD34 fragment was gel purified and inserted into mammalian expression vector pZeoSV2+ (Invitrogen Inc.), via the HindIII and EcoRI sites to generate the vector pZeoSV2-hCD34. The expression of the pZeoSV2-hCD34 was confirmed by transfecting it into HeLa cells and immunostaining with mouse anti-human CD34 monoclonal antibody (Pharmingen Inc., CA).

Enzyme-Linked Immunoassay of Chicken Antibody to Hbxag

Figure 9:
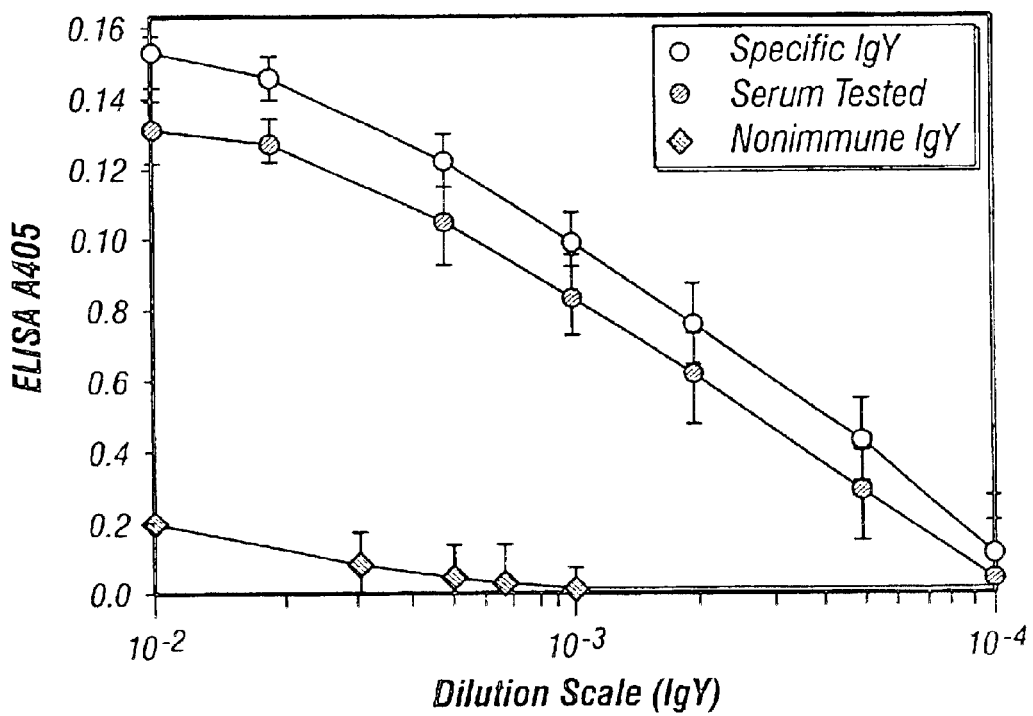
FIG. 9 depicts binding affinity of IgY produced by DNA vaccination with HBxAg.

In this experiment, purified *E. coli* derived HBxAg antigen was used for assaying chicken anti-HBx antibody which was generated from the DNA vaccination as described in § 6.3. Five ug of the purified HbxAg antigen in 200 ul PBS buffer were coated on ELISA plate well (Nalge Nunc Internation., Rockester, N.Y.) overnight. After washing with PBS buffer, 200 ul of 5% BSA were added for further coating the well to block non-specific binding in the assay. Chicken antibody was serially diluted in PBS buffer containing 0.1% bovine serum albumin and incubated in microtiter plate coated with HbxAg antigen for two hours. After 5-time washing with PBS buffer, the HRP-labeled goat-anti-chicken antibody (Sigma Inc., 1:1.0000 dilution) was added into the well and 4' incubated for 1 hour. After another 5-time washing with PBS, the substrate buffer was added and incubated for 15 min with ELISA reading every five minutes. Values are the mean of duplicate samples. FIG. 9 shows that DNA vaccination generated chicken antibody that has very high binding affinity to the HBxAg antigen.

Purification of Chicken Igy from DNA Immunized Chicken Egg Yolk

Laying hens from Hyline Inc. (Dallas Center, Iowa) were kept on regular light cycles. From day 20 after the chickens were immunized with single injection of pCMV-HBx vector as described § 6.3, eggs were collected until the tenth egg was collected. IgY was extracted according to the method described in Polson et al., Immunol. Commun., 1980, 9:475–493. Briefly, yolks were separated from the whites and broken by dropping through a funnel into a graduated cylinder. An equal volume of a buffer (0.01 M phosphate, 0.1 M NaCl, and 0.01% $NaN_3$, pH 7.5) was added and stirred. Pulverized PEG 6000 (Sigma Inc.) was added to a concentration of 3.5% and stirred until it all dissolved. The protein precipitate formed was pelleted by centrifugation at 13,000 g for 10 min. The supernatant was decanted and filtered through cheesecloth and PEG 6000 was added to bring the final concentration to 12%. The mixture was stirred thoroughly and centrifuged again at 13,000 g for 10 min. The pellet was redissolved to the original yolk volume in 0.01 M phosphate-0.1 M NaCl (pH 7.5) and PEG 6000 was added to 12% for a second precipitation. The supernatant was decanted and the pellet was centrifuged twice to extrude the PEG 6000. This final IgY pellet was dissolved in 50 mM Tris-0.1 mM EDTA-25% glycerol-0.02% $NaN_3$ (pH 7.9).

Figure 10:
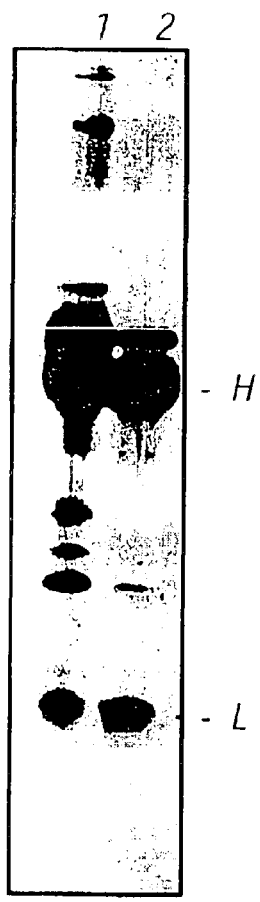
FIG. 10 depicts SDS-PAGE analysis of IgY purified from egg yolks.

For further purification, IgY was purified on DEAE-cellulose by adsorption at 0.015 M KPO4 (pH 8.0) and eluted with a 0.015–0.3 M $KP_{O4}$ (pH 8.0) gradient. Four ug purified samples were separated on 4–20% polyacrylamide gradient gel (BIO-RAD commercial mini-gel) and visualized with silver staining (Sambrook et al., *Molecular Cloning*, Second Edition. Plainview, N.Y. Cold Spring Harbor Press, 1989). The purification results are shown in FIG. 10. Lane 1 is IgY purified through PEG precipitation and Lane 2 is IgY purified by DEAE-cellulose. H and L indicates the position of immunoglobulin heavy and light chain, respectively.

Time Course of Anti-Hbx Production in Hens Determined by Immunoblot Analysis

Figure 11:
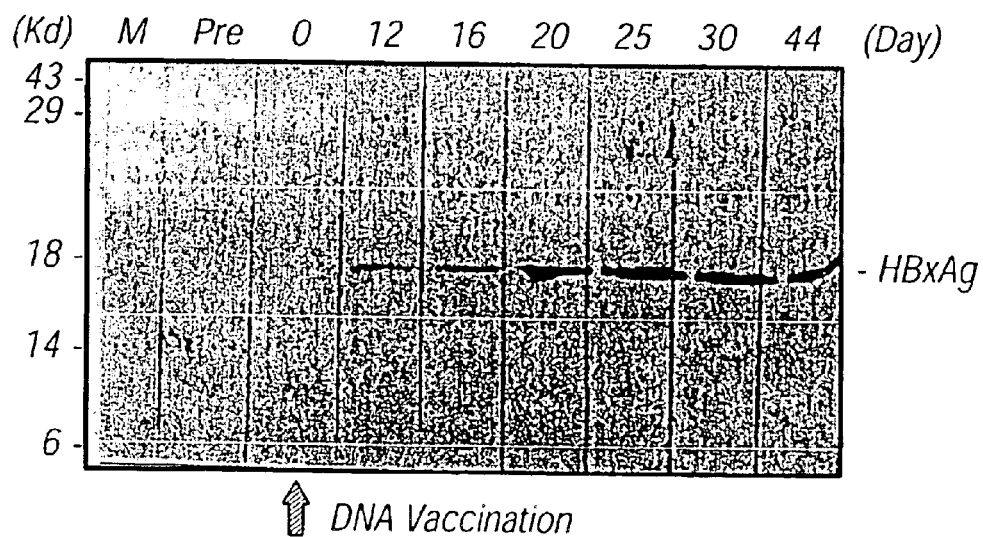
FIG. 11 depicts Western Blot analysis of anti-HBxAg IgY produced by DNA vaccination.

FIG. 10 shows the time course of host immune response to DNA vaccination. The level of anti-HBx antibody was analyzed using purified *E. coli*-derived recombinant HbxAg antigen. Eight ug per well of the purified *E. coli*-derived recombinant HbxAg antigen (as described § 6.3) were separated on a 12.5% SDS-polyacrylamide gel and the separated proteins were transferred onto a PVDA membrane according to the manufacturer's protocol (Bio-Rad mini-gel kit). Yolk antibodies, purified by PEG 6000 precipitation as described in § 6.8, were diluted 1:1200 in Tris-Buffer saline, and 10 ml purified IgY solution were applied to the PVDA membrane and incubated at 37° C. for 2 hours. After 5-time washing with PBS buffer, the membrane was transferred into 20 ml of HRP labeled Goat anti-chicken antibody (1:8000 dilution, Sigma Inc.) solution and incubated at 37° C. for 1 hour. After another 5-time washing with PBS buffer, the immunoblot analysis was performed using Enhanced Chemiluminescence system (PIERCE Inc. ECL kit). FIG. 11 shows that 12 days post DNA vaccination, chicken anti-HBx antibody reached the detectable level.

Map of (pImmo) Used for Immortalizing Chicken B Cells

As human B cells can be immortalized by EBV infection and mouse B cells can be immortalized directly with transfection of oncogenes, such as mutant p53 and Ras oncogenes. Chicken B cells are selected for immortalization with chicken specific oncogene(s) using retroviral vectors transduction system, especially the lantiviral vector system which has the ability to infect the quiescence cells. The ASV (Avian Sarcoma Virus) based vector has been widely used in transforming chicken cells (Kaplitt et al., *Viral Vectors*, Academic Press, 1995). This section describes the construction of an HIV-based vector containing chicken mutant p53 or Ras gene fragment, which can be used for chicken B cell immobilization.

Detailed design for constructing a new lantiviral vector based chicken B cell immortalization vector is described here. HIV-1 based lantiviral vector (Naldini et al., *Science*, 1996, 272:263–268) is used as a starting material for the new vector construction. Chicken mutant p53 oncogene is PCR amplified using following two oligos: Cp53-1 (5'ATGGCGGAGGAGATGGAACCA3') (SEQ ID NO:18) and Cp53-2 (5'TCAGTCCGAGCCTTTTTGCAGCAG 3') (SEQ ID NO:19) (Soussi et al., *Nucleic Acids Research*, 1988, 16:11383). The full-length chicken mutant p53 oncogene is gel purified and inserted into pT7 Bleu(R) vector (Novagen Inc.) to generate the construct pT7-p53. 400 bp Cap-independent translation enhance (CITE) DNA fragment is PCR amplified from pCITE-5b(+) plasmid (Novagen Inc.; Parks et al., *J. Virol.*, 1986, 60:376–384) and inserted into pT7-p53 vector in the downstream of p53 oncogene to produce the pT7-p53-CITE vector. Using two oligos, C-Ras-1(5'ATGACCGAGTACAAGCTG3') (SEQ ID NO:20) and C-Ras-2 (5'TCACGATATCACGCATTTACAG 3') (SEQ ID NO:21), the chicken Ras oncogene is amplified by PCR and the Ras oncogene DNA fragment is inserted into pT7-p53-CITE to generate the dual oncogene expression vector: pT7-p53-CITE-Ras.

By digesting with HindIII-XhoI, LacZ gene DNA fragment in HIV-1 vector is replaced by chicken mutant p53-CITE-Ras oncogene DNA fragments to generate expression vector pHIV-1-Ch-p53-Ras. By linking two oncogenes with the CITE DNA fragment, the oncogenes' expression is driven under a single CMV promoter.

HIV-1 virus host cell specificity problem was overcome by pseudotyping with the G protein of vesicular stomatitis virus (VSV-G). To test this lantiviral vector's transduction efficiency, the experiments to generate the HIV-1 based lantiviral vector transfection stock was performed as the following. Five ug pCMV-VSV-G plasmid, 5 ug HIV-1 help plasmid pCMV*R9 and 10 expression vector pHIV-lacZ were mixed and transfected into $1×10^6$ 293 cells using calcium precipitation procedure (Promega Inc.). In 100 mm cell culture dish, $1×10^6$ 293 cells obtained from ATCC were seeded and cultured at 37° C., in 5% $CO_2$ incubator with 10% FCS supplemented DMEM medium in standard cell culture environments. Four hours before transfection, prewarmed 10% FCS medium was changed. Twelve hours after transfection, the 10 ml fresh pre-warmed medium were changed and 48 hours later, supernatant was collected and mixed with same volume of FCS to store the viral stock sample at 80° C. Alternatively, the viral stock is generated according to the protocol described in Chen et al., *Proc. Natl. Acad. Sci.*, 1996, 93:10057–10062).

The transduction of antiviral vector for chicken cells was tested as the following. $5×10^5$ SL-29 cells (Chicken Embryo fibroblast cells obtained from ATCC) were seeded in 10 ml culture dish with MEM medium supplemented with 5% FCS. Next day, 100 ul serially diluted HIV-1-LacZ viral stock solution were added into SL-29 culture and incubated for 48 hours. All samples were operated in duplicate to control the variation. After washing cells once with PBS buffer, transduced cells were fixed with 0.25% (v/v in PBS) glutaraldehyde solution for 15 minutes, and stained with X-Gal solution (1 mg/ml X-Gal, 2 mM $MgCl_2$, 5 mM $K_4Fe(CN)_6$-$3×H_2O$, 5 mM $K_3Fe(CN)_6$) for 2 hours at 37° C. By counting blue-stained cells, the pseudotyped lantiviral stock title in this experiment was determined to be 1.32×05 ml.

Spleen B cells of DNA vaccinated chickens are immortalized as the following. Chicken spleen cells are collected and purified using Hypaque-Density Ficoll Gradient procedure (Sigma Inc.). After washing three times with PBS buffer, $1×10^5$ mixed B cells are seeded in a six well plate in 1 ml MEM-10% FCS medium and directly mixed with 2 ml viral stock solution overnight. Preferably the viral stock supernatant is treated with 5 mM dNTP and 2 mM spermidine at 37° C. for 2 hours to enhance the viral infectivity (Zhang et al., *J. Virology*, 1995, 69:3929–3932). Four ug/ml polybrene (Sigma Inc) is also added into B cell culture to enhance the viral transduction efficiency during the viral/cell incubation. After B cells are incubated with the viral solution at 37° C. overnight, B cells are diluted into the single well culture (10 cells/well) which contains feeding cells in the 96 well plate (400–500 chicken B cells/well irradiated with 20 Gays). The transformed cells are incubated for two to three weeks, the grown cell supernatant are first tested for the production of IgY antibody (Davis, Ed., *Methods in Molecular Biology*, Monoclonal Antibody Protocols, 1995, Human Press), or screened for specific antigen binding IgY using ELISA as described above.

Determining Housekeeping Gene Occurrence Rate in the Non-Normalized Human Liver Cdna Library In this experiment, the house-keeping gene occurrence rate in the single round DNA sequencing was detected. Two liver specific cDNA libraries were purchased from Invitrogen Inc. (Carlsbad, Calif.), catalog #: A550-39 and Clontech Inc (Palo Alto, Calif.), catalog #: HL400 2A2, respectively. After transferring 1 ul of the library stock to 500 ul LB medium, 10 ul were used to spray the LB plate which contains the selection antibiotic. After incubating the plate at 37° C. overnight, from each of the cDNA library, 300 individual clones were picked up and cultured in 3 ml LB with shaking overnight. Each plasmid was prepared using Quigen Tip20 kit and 1 ug plasmid DNA was sequenced using ABI377 automatic DNA sequencing system with primer suggested by the library manufacturer. The sequencing data were analyzed by blasting sequence data comparison against GenBank database. The data were summarized in Table 1.

TABLE 1

Redundant Transcripts in Human Liver cDNA Library

| Gene Name | Frequency |
| --- | --- |
| NADH-dehydrogenase Chain | 7.2 |
| Albumin | 4.8 |
| Actin | 4.0 |
| ATPase | 4.0 |
| α-Tubulin | 3.2 |
| Cytochrome Oxydase Chain | 2.1 |
| Elongation Factor 1α | 1.0 |
| Myosin Light Chain | 1.0 |
| Aldolase | 0.8 |

The Prototype Structure of Antibody-Chips

After stimulated by a specific antigen, each host B cell generates a specific antibody, which either binds to antigen specific sequential domain or conformational structure domain. A polyclonal antibody binds to a specific antigen through multiple binding sites. The antibody-chip comprising groups of specific antibodies on solid matrix support can be used to capture the free target protein (antigens) in a protein sample solution. After washing steps, the same group of antibody which is conjugated with an enzyme, such as HRP, or a detectable marker such as fluorescence dye (FITC or C3) can be used to further bind those captured antigen because of multiple binding domains of polyclonal antibodies, and to determine binding signal density with substrate of the enzyme such as ECL system or laser emission system (flowcytometer). In contrast, if the above capturing and labeled-binding steps are carried out using a monoclonal antibody, the binding efficiency is very low due to the single binding domain of the monoclonal antibody to the specific antigen. Although this problem could theoretically be overcome by using two monoclonal antibodies for every single antigen, the characterization of each different monoclonal antibody is extremely time consuming and hardly be practical.

Using AMIGAP of the present invention, one can generate multiple antibodies to unknown proteins or functionally undefined proteins. After purification of each IgY antibody, one can divide each of the antibody into two fractions and label one of the fraction with biotin (PIERCE Inc. IL. EZ-Link Biotinylating Reagents). Hundreds or thousands specific unlabeled antibodies are individually and randomly spotted on two identical solid support matrix (e.g., 1 ug of each of antibody per spot on PVDF membrane or marked individual glass bead; and each spot or bead represents one known antibody). The spotted matrix is blocked with 5% BSA-PBS buffer to reduce the non-specific binding background. Specific group of antibodies, such as the antibodies targeting cell-cycle specific regulatory proteins or G-coupled receptor family proteins, can be used. The antibody-chip can be air-dried and stored at 4° C. in the sealed plastic bag for several months. Before performing the experiments, the antibody-chip can be activated by wetting the chip in PBS buffer for 30 minutes.

The system described here can be used in comparing the target protein expression in two samples, such as liver tumor cells vis-a-vis normal liver cells or human lung cancer cells treated with anti-cancer drug vis-a-vis untreated control cells. For preparing the protein sample, two target cell samples or tissues can be lysed by gentle detergents in PBS solution or freeze and thaw method (Sambrook et al., *Molecular Cloning*, Second Edition. Plainview, N.Y. Cold Spring Harbor Press, 1988). Same number of cells can be used for protein expression comparison. Alternatively, cell lysate sample are measured with its protein concentration first and then equal amount of protein sample are loaded onto the antibody-chips. Usually, $1 \times 10^6$ cells per lysate sample or 50□100 ug proteins are used for each assay.

Each of protein samples is added to those identical antibody-chip and incubated at 37° C. for 2 hours with slow shaking. After docking antibody specifically bind to its target antigen, simple washing steps is used to remove the un-captured cellular proteins. Antibody-chips are washed with PBS solution for four times, 15 □30 minutes per washing.

As cellular target proteins are captured by membrane-bound docking antibodies, functioning as sandwich fashion, those captured target proteins are detected by mixture solution of biotin labeled antibodies which corresponds to each of the originally spotted antibodies and incubated 37° C. for 2 hours. The signal density of the captured biotin-labeled antibodies is associated with the level of docking cellular protein level (antigen). Further quantification of captured biotin-labeled antibodies shows the antigen expression level in this assay. After washing 5 times in PBS buffer, the non-captured biotin-labeled antibodies on the antibody-chips are removed. Finally, avidin conjugated HRP (Sigma Inc. 1:8000 dilution in PBS with 2% BSA) is added and incubated for 15 minuets. After washing the antibody-chips with PBS solution for six times and soaking the antibody-chip with ECL substrate solution (PIERCE Inc. IL), the chip is exposed to X-ray film.

The above examples are included for illustrative purposes only and is not intended to limit the scope of the invention. Since modifications will be apparent to those of skill in this art, it is intended that this invention be limited only by the scope of the appended claims.

What is claimed is:

1. A process for assessing a proteomics profile of a set of pre-selected DNA sequences isolated from a bio-sample, which comprises:

1) cloning each of said DNA sequences into a dual-expression vector that is capable of expressing said DNA sequences in chicken cells, non-chicken cells or in vitro expression systems;

2) delivering said DNA sequence in said dual-expression vector formed in step 1), or protein encoded by said DNA sequence, or a mixture thereof, to a chicken in an amount sufficient to induce detectable production of antibodies to an antigen encoded by said DNA sequence, and recovering said antibodies from said chicken;

3) delivering said DNA sequence, which is delivered to said chicken in step 2), to said non-chicken cells, and recovering proteins or peptides encoded by said DNA sequence from said non-chicken cells, or expressing and recovering proteins or peptides encoded by said DNA sequence in said in vitro expression systems;

4) conducting immunoreactions between said antibodies recovered in step 2) with said proteins or peptides recovered from step 3) to characterize the immuno-specificity of said antibodies; and 5) conducting immunoreactions between said antibodies recovered in step 2) with said bio-samples to determine the proteomics profile of said set of pre-selected DNA sequences.

2. The process of claim 1, wherein the set of pre-selected DNA sequences is a cDNA library.

3. The process of claim 2, wherein the cDNA library encodes secreted proteins or peptides in the bio-sample.

4. The process of claim 1, wherein the bio-sample is of human origin.

5. The process of claim 1, wherein the dual-expression vector is a pS&DV vector comprising a ColE1 replication origin, a CMV promoter, a T7/Lac operon, a RBS/Kozak region, a polilinker region, a T7 termination region and an Amp gene.

6. The process of claim 1, wherein the non-chicken cells are animal, plant, or fungus cells.

7. The process of claim 1, wherein the non-chicken cells are bacterium cells.

8. The process of claim 1, wherein the DNA sequence is delivered to the chicken.

9. The process of claim 8, wherein the DNA sequence is delivered directly to a tissue of the chicken.

10. The process of claim 9, wherein the tissue is selected from the group consisting of muscle, skin and mucous membrane.

11. The process of claim 9, wherein the DNA sequence is delivered by injection, by gene gun technology or by lipid mediated delivery technology.

12. The process of claim 8, wherein the DNA sequence is delivered to a cell of the chicken and said cell containing the DNA sequence is delivered to a suitable tissue of the chicken.

13. The process of claim 12, wherein the cell is selected from the group consisting of a blood cell and a spleen B cell.

14. The process of claim 12, wherein the DNA sequence is delivered to the cell by a method selected from the group consisting of $Ca_3(PO_4)_2$-DNA transfection, DEAE dextran-DNA transfection, electroporation, transfection using (1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water, gene gun technology and viral gene delivery system.

15. The process of claim 8, wherein the DNA sequence encoding the antigen is contained and delivered in a viral vector derived from an adenovirus.

16. The process of claim 8, wherein the DNA sequence encoding the antigen is contained and delivered in a viral vector.

17. The process of claim 1, wherein the protein encoded by the DNA sequence is delivered to the chicken.

18. The process of claim 1, wherein the antibodies are recovered from egg yolk of the chicken.

19. The process of claim 18, wherein the antibodies are purified from the egg yolk by ammonium sulfate precipitation, by polyethylene glycol 6000 precipitation or by caprylic acid precipitation.

20. The process of claim 1, wherein the antibodies are recovered from antibody-producing B cells of the chicken.

21. The process of claim 1, wherein the non-chicken cells are E. coli cells.

22. The process of claim 1, wherein the immunoreactions are assayed by immunoblotting, immunoprecipitation or in situ immunostaining.

23. The process of claim 1, wherein in step 5) the immunoreactions are conducted to determine the existence, quantity, subcellular location or tissue expression specificity of proteins or peptides encoded by the set of pre-selected DNA sequences in evaluating the proteomics profile of the set of pre-selected DNA sequences in the bio-sample.

24. The process of claim 1, wherein the pre-selected DNA sequences are isolated from a physiologically normal bio-sample.

25. The process of claim 1, wherein the pre-selected DNA sequences are isolated from a physiologically abnormal bio-sample.

26. The process of claim 1, wherein the DNA sequence further comprises a sequence that directs secretion of the encoded antigen in the chicken.

27. The process of claim 26, wherein the secretion-directing sequence is a leader sequence.

28. The process of claim 27, wherein the leader sequence is an endogenous leader sequence of the chicken.

29. The process of claim 27, wherein the leader sequence is selected from the group consisting the leader sequence of chicken IgY, chicken Secreted Protein, Acidic, Rich in Cysteine (SPARC), chicken serum albumin and chicken tissue-type plasminogen activator (tPA).

30. The process of claim 27, wherein the leader sequence is selected from the group consisting of the leader sequence of IL-1, CD4 and MHC.

31. A process for identifying physiologically distinguishable markers associated with a physiologically abnormal bio-sample, which comprises:

1) assessing a proteomics profile of said physiologically abnormal bio-sample through the process of claim 1;

2) assessing a proteomics profile of a comparable physiologically normal bio-sample through the process of claim 1; and 3) comparing the proteomics profile obtained in step 1) with the proteomics profile obtained in step 2) to identify physiologically distinguishable markers associated with a physiologically abnormal bio-sample.

32. A method for identifying a substance that modulates a proteomics profile of a bio-sample, which method comprises:

1) assessing a proteomics profile of a bio-sample through the process of claim 1 in the presence of a test substance;

2) assessing a proteomics profile of said bio-sample through the process of claim 1 in the absence said test substance; and 3) comparing the proteomics profile obtained in step 1) with the proteomics profile obtained in step 2), whereby the existence of a difference between the proteomics profile obtained in step 1) and the proteomics profile obtained in step 2) identifies the test substance as a modulator of said proteomics profile of said bio-sample.

33. The process of claim 1, wherein a mixture of the DNA sequence and the protein encoded by the DNA sequence is delivered to the chicken.

34. The process of claim 1, wherein the immunoreactions are assayed by an antibody array or an tissue array.

* * * * *

SEQUENCE LISTING

<160> NUMBER OF SEQ ID NOS: 24

<210> SEQ ID NO 1
<211> LENGTH: 22
<212> TYPE: DNA
<213> ORGANISM: Artificial sequence
<220> FEATURE:
<223> OTHER INFORMATION: CMV-1 oligonucleotide

<400> SEQUENCE: 1
caccctgaat tgactctctt tc                                              22

<210> SEQ ID NO 2
<211> LENGTH: 42
<212> TYPE: DNA
<213> ORGANISM: Artificial sequence
<220> FEATURE:
<223> OTHER INFORMATION: Pacll-1 oligonucleotide

<400> SEQUENCE: 2
atatgaattc ttaattaaga tctccatggt ggcctctcct tc                        42

<210> SEQ ID NO 3
<211> LENGTH: 35
<212> TYPE: DNA
<213> ORGANISM: Artificial sequence
<220> FEATURE:
<223> OTHER INFORMATION: Pacl oligonucleotide

<400> SEQUENCE: 3
cgcggaattc gcggccgcta ccaggtaagt gtacc                                35

<210> SEQ ID NO 4
<211> LENGTH: 34
<212> TYPE: DNA
<213> ORGANISM: Artificial sequence
<220> FEATURE:
<223> OTHER INFORMATION: ter-2 oligonucleotide

<400> SEQUENCE: 4
cgagtagttt aaacaaaaaa cccctcaagt cccg                                 34

<210> SEQ ID NO 5
<211> LENGTH: 31
<212> TYPE: DNA
<213> ORGANISM: Artificial sequence
<220> FEATURE:
<223> OTHER INFORMATION: T7A oligonucleotide

<400> SEQUENCE: 5
agatctgttt aaaccaggtg gcacttttcg g                                    31

<210> SEQ ID NO 6
<211> LENGTH: 31
<212> TYPE: DNA
<213> ORGANISM: Artificial sequence
<220> FEATURE:
<223> OTHER INFORMATION: T7B oligonucleotide

<400> SEQUENCE: 6
agatctgttt aaacagctgt ttcctgtgtg a                                    31

<210> SEQ ID NO 7
<211> LENGTH: 20

```
<212> TYPE: PRT
<213> ORGANISM: Artificial Sequence
<220> FEATURE:
<223> OTHER INFORMATION: chicken IgY Vh1 signal domain

<400> SEQUENCE: 7

Met Ser Pro Leu Val Ser Ser Leu Leu Leu Ala Ala Leu Pro Gly
 1               5                  10                  15

Leu Met Ala Ala
            20

<210> SEQ ID NO 8
<211> LENGTH: 71
<212> TYPE: DNA
<213> ORGANISM: Artificial sequence
<220> FEATURE:
<223> OTHER INFORMATION: Linker-1

<400> SEQUENCE: 8
aaccctcttc catgagccca ctcgtctcct ccctcctgct cctggccgcc ctgccagggc    60
tgatggcggc c                                                         71

<210> SEQ ID NO 9
<211> LENGTH: 62
<212> TYPE: DNA
<213> ORGANISM: Artificial sequence
<220> FEATURE:
<223> OTHER INFORMATION: Linker-2

<400> SEQUENCE: 9
cagatcctct tcgaagctag cggccgcgaa ttcttaatta aggccgccat cagccctggc    60
ag                                                                   62

<210> SEQ ID NO 10
<211> LENGTH: 32
<212> TYPE: DNA
<213> ORGANISM: Artificial sequence
<220> FEATURE:
<223> OTHER INFORMATION: MF 18 oligonucleotide

<400> SEQUENCE: 10
ggaagcttgc cgccatggct gctaggctgt gc                                  32

<210> SEQ ID NO 11
<211> LENGTH: 25
<212> TYPE: DNA
<213> ORGANISM: Artificial sequence
<220> FEATURE:
<223> OTHER INFORMATION: MF 19 oligonucleotide

<400> SEQUENCE: 11
gtggagacgg attagtacca tggcc                                          25

<210> SEQ ID NO 12
<211> LENGTH: 33
<212> TYPE: DNA
<213> ORGANISM: Artificial sequence
<220> FEATURE:
<223> OTHER INFORMATION: MF 26 oligonucleotide

<400> SEQUENCE: 12
aagagctcgc caccatggcc ctatcctatc aac                                 33

<210> SEQ ID NO 13
```

```
<211> LENGTH: 29
<212> TYPE: DNA
<213> ORGANISM: Artificial sequence
<220> FEATURE:
<223> OTHER INFORMATION: HBVpol-2 oligonucleotide

<400> SEQUENCE: 13
tcaccttaag gtgttggaag gtggtttga                              29

<210> SEQ ID NO 14
<211> LENGTH: 29
<212> TYPE: DNA
<213> ORGANISM: Artificial sequence
<220> FEATURE:
<223> OTHER INFORMATION: Pol-3 oligonucleotide

<400> SEQUENCE: 14
ggccatgcag tggaattcca ctgccttcc                              29

<210> SEQ ID NO 15
<211> LENGTH: 30
<212> TYPE: DNA
<213> ORGANISM: Artificial sequence
<220> FEATURE:
<223> OTHER INFORMATION: Pol-4 oligonucleotide

<400> SEQUENCE: 15
aaccaagctt cacggtggtc tggatgcaac                             30

<210> SEQ ID NO 16
<211> LENGTH: 22
<212> TYPE: DNA
<213> ORGANISM: Artificial sequence
<220> FEATURE:
<223> OTHER INFORMATION: hCD34-1 primer

<400> SEQUENCE: 16
gaaggatgct ggtccgcagg gg                                     22

<210> SEQ ID NO 17
<211> LENGTH: 22
<212> TYPE: DNA
<213> ORGANISM: Artificial sequence
<220> FEATURE:
<223> OTHER INFORMATION: hCD34-2 primer

<400> SEQUENCE: 17
cacctagccg agtcacaatt cg                                     22

<210> SEQ ID NO 18
<211> LENGTH: 21
<212> TYPE: DNA
<213> ORGANISM: Artificial sequence
<220> FEATURE:
<223> OTHER INFORMATION: Cp 53-1 oligonucleotide

<400> SEQUENCE: 18
atggcggagg agatggaacc a                                      21

<210> SEQ ID NO 19
<211> LENGTH: 24
<212> TYPE: DNA
<213> ORGANISM: Artificial sequence
<220> FEATURE:
<223> OTHER INFORMATION: Cp 53-2 oligonucleotide

<400> SEQUENCE: 19
```

```
tcagtccgag ccttttttgca gcag                                              24
```

<210> SEQ ID NO 20
<211> LENGTH: 18
<212> TYPE: DNA
<213> ORGANISM: Artificial sequence
<220> FEATURE:
<223> OTHER INFORMATION: C-Ras-1 oligonucleotide

<400> SEQUENCE: 20

```
atgaccgagt acaagctg                                                      18
```

<210> SEQ ID NO 21
<211> LENGTH: 22
<212> TYPE: DNA
<213> ORGANISM: Artificial sequence
<220> FEATURE:
<223> OTHER INFORMATION: C-Ras-2 oligonucleotide

<400> SEQUENCE: 21

```
tcacgatatc acgcatttac ag                                                 22
```

<210> SEQ ID NO 22
<211> LENGTH: 44
<212> TYPE: DNA
<213> ORGANISM: Artificial Sequence
<220> FEATURE:
<223> OTHER INFORMATION: polilinker region DNA sequence

<400> SEQUENCE: 22

```
atggagatct taattaagaa ttcgcggccg ctaccaggta agtg                          44
```

<210> SEQ ID NO 23
<211> LENGTH: 95
<212> TYPE: DNA
<213> ORGANISM: Artificial Sequence
<220> FEATURE:
<223> OTHER INFORMATION: polilinker region DNA sequence

<400> SEQUENCE: 23

```
atgagcccac tcgtctcctc cctcctgctc ctggccgccc tgccagggct gatggcggcc         60
ttaattaaga attcgcggcc gctaccaggt aagtg                                   95
```

<210> SEQ ID NO 24
<211> LENGTH: 20
<212> TYPE: PRT
<213> ORGANISM: Artificial Sequence
<220> FEATURE:
<223> OTHER INFORMATION: chicken IgY Vh1 secreted domain

<400> SEQUENCE: 24

```
Met Ser Pro Leu Val Ser Ser Leu Leu Leu Leu Ala Ala Leu Pro Arg
 1               5                  10                  15

Leu Met Ala Ala
            20
```